US005424395A

United States Patent [19]

Bascomb et al.

[11] Patent Number: 5,424,395

[45] Date of Patent: Jun. 13, 1995

[54] ANTIMICROBIAL PEPTIDES ACTIVE AGAINST PLANT PATHOGENS

[75] Inventors: Newell F. Bascomb, Lawrenceville; Claudio Mapelli; Michael D. Swerdloff, both of Princeton; Jon I. Williams, Robbinsville; Nicholas P. Everett, Pennington City, all of N.J.

[73] Assignee: Enichem S.P.A., Italy

[21] Appl. No.: 937,236

[22] Filed: Aug. 28, 1992

Related U.S. Application Data

[63] Continuation of Ser. No. 566,152, Aug. 10, 1990, abandoned.

[51] Int. Cl.[6] ........................ A61K 38/00; C07K 5/00; C07K 7/00; C07K 17/00

[52] U.S. Cl. .................................... 530/326; 530/300

[58] Field of Search ............................ 514/12, 13, 21; 530/300, 326, 325, 324, 317, 827, 842

[56] References Cited

U.S. PATENT DOCUMENTS 4,458,066 7/1984 Caruthers et al. .
4,543,252 9/1985 Lehrer et al. ........................ 514/12
4,810,777 3/1989 Zasloff ................................ 530/326

FOREIGN PATENT DOCUMENTS 8800976 7/1987 WIPO .
8806597 2/1988 WIPO .
0299828 6/1988 WIPO .
8911290 5/1989 WIPO .
9006129 12/1989 WIPO .

OTHER PUBLICATIONS

Dorper et al., "Improvements in the phosphoramidite procedure for the synthesis of oligodeoxyribonucleotides", Nucleic Acids Research, vol. 11, No. 9, 1983.

DeGreve et al., "Nucleotide Sequence and Transcript Map of the *Agrobacterium tumefaciens* Ti Plasmid-Encoded . . . ", Journal of Molecular and Applied Genetics, 499–511, 1983.

Winkler, "Biosynthesis of Histidine", Department of Molecular Biology, Northwestern University Medical School, 395–411.

Klement, "Method of Obtaining Fluid from the Intercellular Spaces . . . ", Phytopathology, vol. 55, 1033–1034.

Berkowitz et al., "Magainins: A New Family of Membrane-Active Host Defense Peptides", Biochemical Pharmacology, vol. 39, No. 4, pp. 625–629, 1990.

Zasloff et al., "Antimicrobial activity of synthetic magainin peptides and several analogues", Proc. Nat. Acad. Sci. USA, vol. 85, pp. 910–913, Feb. 1988.

Urrutia et al., "Spontaneous polymerization of the antibiotic peptide magainin 2", vol. 247, No. 1, 17–21.

Duclohier et al., "Antimicrobial peptide magainin 1 from Xenopus skin forms anion-permeable channels in planar lipid bilayers", Biophys. J., vol. 56, Nov. 1989, 1017–1021.

Rana et al., "Interactions between *Salmonella typhimurium* lipopolysaccharide and the antimicrobial peptide, magainin 2 amide", vol. 261, No. 2, 464–467.

(List continued on next page.)

*Primary Examiner*—Jill Warden
*Assistant Examiner*—A. M. Davenport
*Attorney, Agent, or Firm*—Lerner, David, Littenberg, Krumholz & Mentlik

[57] ABSTRACT

The present invention relates to a number of peptides which have antimicrobial activity and which are useful in retarding plant pathogens. In addition, compounds in accordance with the present invention may have improved resistance to degradation by plant proteases, and/or sufficiently low phytotoxicity to render them likely candidates for use in conjunction with plants. The present invention also relates to oligonucleotides which are capable of expressing the aforementioned peptides. Also provided hereby is a process of retarding the growth of plant pathogens using the compounds of the present invention as well as a screening method and screening reagent useful in determining the proteolytic degradation resistance of a known compound.

27 Claims, No Drawings

OTHER PUBLICATIONS

Cuervo et al., "The Magainins: Sequence Factors Relevant to Increased Antimicrobial Activity and Decreased Hemolytic Activity", Peptide Research, vol. 1, No. 2 (1988), 81–86.

Zasloff, "Magainins, a class of antimicrobial peptides from Xenopus skin: Isolation, characterization of two active . . . ", Proc. Natl. Acad. Sci. USA, vol. 84, pp. 5449–5453, Aug. 1987.

Matsuzaki et al., "Magainin 1–induced leakage of entrapped calcein out of negatively–charged lipid vesicles", Biochimica et Biophysica Acta, 981 (1989) 130–134.

Rana et al., "Outer Membrane Structure in Smooth and Rough Strains of *Salmonella typhimurium* and Their . . . ", Biological and Synthetic Membranes, pp. 77–85, 1989.

Westerhoff et al., "Magainins and the disruption of membrane–linked free–energy transduction", Proc. Natl. Acad. Sci. USA, vol. 86, pp. 6597–6601, Sep. 1989.

Giovannini et al., "Biosynthesis and degradation of peptides derived from *Xenopus laevis* prohormones", Biochem. J. (1987) 243, 113–120.

Gordon–Kamm et al., "Transformation of Maize Cells and Regeneration of Fertile Transgenic Plants", The Plant Cell, vol. 2, 603–618, Jul. 1990.

Tjoeng et al., "Multiple peptide synthesis using a single support (MPS3)", Int. J. Peptide Protein Res. 35, 1990, 141–146.

Horsch, "A Simple and General Method for Transferring Genes Into Plants", Science, vol. 227, pp. 1229–1231, Mar. 1985.

Hellebust et al., "Different Approaches to Stabilize a Recombinant Fusion Protein", Bio/Technology, vol. 7, pp. 165–168, Feb. 1989.

Zon et al., "A Review of High–Performance Liquid Chromatography in Nucleic Acids Research, II. Isolation, Purification, and . . . ", BioChromatography, vol. 1, No. 1, pp. 22–31, (1986).

Thompson, "A Review of High Performance Liquid Chromatography in Nucleic Acids Research, I. Historical Perspectives", BioChromatography, vol. 1, No. 1, pp. 16–20, (1986).

Gupta et al., "Development and Use of Chlorotetracycline Fluorescence as a Measurement Assay of Chloroplast Envelope–Bound $Mg^{2+1}$", Platn Physiol., (1989) 89, 753–761.

Brosius, "Expression Vectors Employing λ–, trp–, lac–, and 1pp–Derived Promoters", Chapter 10, pp. 205–225.

Caruthers, "New Methods for Chemically Synthesizing Deoxyoligonucleotides", Methods of DNA and RNA Sequencing, pp. 1–22.

Williams et al., "Raman Spectroscopy of Synthetic Antimicrobial Frog Peptides Magainin 2a and PGLa", Biochemistry 1990, 29, 4490–4496.

Chen et al., "Synthetic magainin analogues with improved antimicrobial activity", vol. 236, No. 2, 462–466, Aug. 1988.

Juretic et al., "Magainin 2 amide and analogues, Antimicrobial activity, membrane depolarization and susceptibility to proteolysis", vol. 249, No. 2, 219–223, Jun. 1989.

Chen et al., "Magainin analogs: A study of activity as a function of α–helix modification", Structural biology, pp. 122–123.

Cuervo et al., "Synthesis and antimicrobial activity of magainin alanine substitution analogs", Structural biology, pp. 124–126.

Cannon, "Antimicrobial peptides, A family of wound healers", Nature, vol. 328, Aug. 6, 1987, p. 478.

Nozaki, "Solid Phase Synthesis of Magainin 1 under Continuous Flow Conditions 1", Chemistry Letters, pp. 749–752, 1989.

Casteels et al., "Apidaecins: antibacterial peptides from honeybees", the EMBO Journal, vol. 8, No. 8, pp. 2387–2391, 1989.

Jaynes et al., "Increasing Bacterial Disease Resistance in Plants Utilizing Antibacterial Genes from Insects", BioEssays, vol. 6, No. 6, Jun. 1987, pp. 263–270.

Itakura et al., "Synthesis and Use of Synthetic Oligonucleotides", Ann. Rev. Biochem., 1984, 53:323–56.

Goldberg et al., "Cloning and expression of a collagen–analog–encoding synthetic gene in *Escherichia coli*", Gene, 80 (1989) 305–314.

Kuks et al., "*Xenopus laevis* Skin Arg–Xaa–Val–Arg–Gly–endoprotease", The Journal of Biological Chemistry, vol. 264, No. 25, Sep. 5, 1989, pp. 14609–14612.

Chen et al., "An extracellular matrix protein in plants: characterization of a genomic clone for carrot extensin", The EMBO Journal, vol. 4, No. 9, pp. 2145–2151, 1985.

Kini et al., "A common cytolytic region in myotoxins, hemolysins, cardiotoxins and antibacterial peptides", Int. J. Peptide Protein Res. 34, 1989, 277–286.

Bessalle et al.–Novel magainin analogues: Structure–activity relationship, Peptides 1990.

Maloy et al.–Design of broad spectrum antibiotic and host defense peptides based on magainin and related peptides, Peptides 1990.

ANTIMICROBIAL PEPTIDES ACTIVE AGAINST PLANT PATHOGENS

This is a continuation of application Ser. No. 07/566,152, filed Aug. 10, 1990 and now abandoned.

FIELD OF THE INVENTION

The present invention relates to the field of peptides which are useful for combating plant pathogens, and methods of their use against plant pathogens. The present invention also relates to screening methods useful in conjunction therewith.

BACKGROUND OF THE INVENTION

Chemical compounds of various types can inhibit the growth of or kill microbes or other life forms. Mankind has exploited this phenomenon as exemplified by such everyday items as over-the-counter disinfectants and pharmaceutical compounds such as antibiotics. The invention that is the subject of this work deals with modification to and elaboration upon a recently discovered class of antimicrobial compounds. Unlike the common antimicrobial compounds exemplified above, the compounds making up this class are proteins also known as peptides. Proteins are made up of individual building blocks called amino acids. The amino acids are linked together by chemical links called peptide bonds. One end of the string of amino acids that makes up a protein is called the N-terminal end or amino terminal end, and the other end is called the C-terminal or carboxyl terminal end.

A particular peptide can be "built" in two ways. One way is to chemically synthesize the peptide using exclusively human, i.e., non-genetic intervention. Under this methodology the particular amino acid building blocks are selected and connected in the appropriate order using chemical reactions. This chemical synthesis of proteins does not directly involve biological or genetic assistance. The second method employs such assistance by manipulating the genetics of a cell system such that the system makes the desired protein. This latter methodology is commonly referred to as genetic engineering.

The antimicrobial peptides that are the subject of this invention, as will be set forth more fully in detail below, have been modified as taught by this invention so that they are especially useful in agricultural settings. Using the discoveries and teachings of this invention, it has been established that antimicrobial peptides can be used to retard and/or kill plant pathogens that have proved to be a nuisance, or worse destructive, to plants having either agronomic value or horticultural value. Among the practical applications of this invention are the application of these antimicrobial peptides to plants using traditional methods such as sprays, or non-traditional methods such as by genetically modifying or engineering plant cells such as corn or potatoes to express these peptides. For example, genetic material that codes for one of the antimicrobial peptides of this invention could be inserted into corn (maize) that ordinarily does not have genes for these peptides thereby conferring a high degree of plant pathogen resistance to the genetically transformed corn plant. In this connection it is significant that these antimicrobial peptides ordinarily are not found in plant cells. In either event the benefits to society from this invention are anticipated to be quite significant because the antimicrobial compounds set forth herein could significantly reduce, or in some cases eliminate, the need for costly, petroleum-derived pesticide compounds.

The antimicrobial peptides to which we have been referring were first reported in 1987 when two groups of researchers, one headed by Dudley Williams and one headed by Michael Zasloff, successfully characterized and reported a number of peptides derived from natural peptides which are secreted by glands contained within the skin of the African Clawed Frog, *Xenopus laevis*. See, Giovannini, et al., "Biosynthesis and Degradation of Peptides Derived from *Xenopus Laevis* Prohormones" *Biochem. J.* 243, (1987), 113–120; and Zasloff, "Magainins, A Class of Anti-microbial Peptides From *Xenopus* Skin: Isolation, Characterization of Two Active Forms and Partial cDNA Sequence of a Precursor," *Proc. Natl. Acad. Sci. USA* 84, (1987), 5449–5453. Their research was prompted, at least in part, by the observation that this species of frog has remarkable recuperative power and the ability to remain free from infection during wound-healing with little or no postoperative care.

Amongst these peptides, two 23 residue compounds, popularly named magainins, have become the subject of increasing attention. These are Magainin 1 having an amino acid sequence of Gly-Ile-Gly-Lys-Phe-Leu-His-Ser-Ala-Gly-Lys-Phe-Gly-Lys-Ala-Phe-Val-Gly-Glu-Ile-Met-Lys-Ser, and Magainin 2 having replacements of Lys for Gly at position 10 and Asn for Lys at position 22 in the above sequence. Both Magainin 1 and Magainin 2 have been investigated for potential pharmaceutic use because of their broad spectrum antimicrobial activity against human pathogens. This is particularly true of Magainin 2.

In addition, a number of magainin based derivatives having varying degrees of activity have been produced and investigated. See Juretic, et al., "Magainin 2 Amide and Analogues, Antimicrobial Activity, Membrane Depolarization and Susceptibility of Proteolysis, " *Febs Lett.* 249, (1989), 219–223; Chen, et al., "Synthetic Magainin Analogues With Improved Antimicrobial Activity," *Febs Lett.* 236, (1988), 462–466; Chen et al, U.S. patent application Ser. No. 280,363, filed Dec. 6, 1988; Cuervo, et al., "Synthesis and Antimicrobial Activity of Magainin Alanine Substitution Analogs," Proceedings of the Eleventh American Peptide Symposium; Peptides: Chemistry, Structure and Biology (J. E. Rivier, et al.), (1990), pp. 124–126, published by ESCOM-Leiden, Neth.; Cuervo, et al., "The Magainins: Sequence Factors Relevant to Increased Antimicrobial Activity and Decreased Hemolytic Activity," *Peptide Research* 1, (1988), 81–86; World Patent Application No. WO 88/06597; and Japanese Patent Application No. JP-1/299,299. These include the complete single residue omission analogue series of Magainin 1 and 2, select N-terminal omissions of Magainin 2, as well as the complete alanine (Ala) replacement analog series of Magainin 2, and Magainin 2 derivatives which may be useful as an antibiotic and/or an anti-cancer drug and which are substituted at the 5th and 12th positions.

These magainin derivatives raise more questions about the nature, the properties, and characteristics of the structure and activity of magainins and magainin derived peptides than they answer. For example, both Zasloff, et al. and Cuervo, et al. have reported that omission analogs of magainins have reduced activity against animal pathogens. See, Zasloff et al., "Antimicrobial Activity of Synthetic Magainin Peptides and Several Analogs," Proc. Natl. Acad. Sci. USA 85, (1988), 910–913; and Cuervo, et al., "The Magainins: Sequence Factors Relevant to Increased Antimicrobial Activity and Decreased Hemolytic Activity" supra. Both research groups also appear to agree that the N-terminal region (amino acids 1–14) is critical for the activity of the peptide with regard to animal pathogens. However, there is no agreement on the extent to which omissions in this region affect the antimicrobial activity of the resulting peptide. Zasloff's group has established that magainin omission derivatives having only a single omitted amino acid at the amino terminus do not show appreciable decrease in activity. According to Zasloff's research, only when the resulting peptide is 19 residues or shorter (consecutive omissions from the N-terminus) is the decrease in activity significant, and/or total. This is in stark contrast to the findings of Cuervo's group. Cuervo et al. found that single residue omissions in the N-terminal region totally defeated the activity of Magainin 1 and Magainin 2 amide (—$NH_2$).

These two research groups have also produced conflicting information with regard to the relative influence of single amino acid deletions on the carboxyl terminus of Magainin 2. Zasloff and his colleagues have demonstrated that removal of the Ser residue at the carboxyl end of Magainin 2 essentially eliminated activity against human bacterial pathogens, while Cuervo et al. reported only limited reduction in the activity of this single omission derivative of Magainin 2 against some of the same human pathogens. See M. Zasloff, U.S. Pat. No. 4,810,777; and Cuervo et al., "The Magainins: Sequence Factors Relevant To Increased Antimicrobial Activity and Decreased Hemolytic Activity," supra. Surprisingly, the present inventors have discovered that single and double residue omissions in the C-terminal (not N-terminal) region of magainins and magainin derived peptides can have profound effects on activity, especially with regard to efficacy against plant pathogens as opposed to animal pathogens.

The examination of certain substitution derivatives of natural magainins only exacerbates these issues of critical positions. Specifically, the N-terminal region of magainins and/or magainin-derived peptides is supposedly critical for activity. See Cuervo et al., "The Magainins: Sequence Factors Relevant To Increased Antimicrobial Activity and Decreased Hemolytic Activity," supra. In addition, a substitution of Ala in position 19 of the amide form of Magainin 2 yielded a five-fold increase in potency when compared to unsubstituted Magainin 2—$NH_2$. This substitution was superior to all other Ala substitutions in positions 1–14. See, Cuervo et al. "Synthesis And Antimicrobial Activity of Magainin Alanine Substitution Analogs". supra; see, also, Chen et al., "Synthetic Magainin Analogs With Improved Antimicrobial Activity," supra (reporting increased antimicrobial activity of a Magainin 2 having alanine substituted in the 8th, 13th, and 18th positions thereof). Thus, no clear guidance is extant as to the specific modifications which would render such peptides useful in protecting plants from plant pathogens.

Much of the magainin literature has concentrated on the postulated mechanism by which magainin peptides inhibit microbial activity and cause lysis in, for example, protozoa. These papers have also discussed the interrelationship of the alpha-helix structure, size and charge attributed to these peptides and their utility as antimicrobial agents. See, generally, Matsuzaki, et al., "Magainin 1-Induced Leakage of Entrapped Calcein Out Of Negatively-Charged Lipid Vesicles," *Biochimica et Biophysica Acta* 981 (1989), 130–134; Rana, et al., "Outer Membrane Structure in Smooth and Rough Strains of *Salmonella Typhimurium* and Their Susceptibility to the Antimicrobial Peptides, Magainins and Defensins, " *Prog. Clin. Biol Res.* 292, (1989), 77–85; Chen, et al., "Magainin Analogs: A Study of Activity as a Function of Alpha-Helix Modification," Proc. of Eleventh American Peptide Symposium, supra, at pp. 124–126; Westerhoff, et al., "Magainins and the Disruption of Membrane Linked Free-Energy Transduction," *Proc. Natl. Acad. Sci. USA* 86, (1989), 6597–6601; and U.S. Pat. No. 4,810,777. See, also, Cannon, "A Family of Wound Healers," *Nature* 328, (1987), 478; Williams et al., "Raman Spectroscopy of Synthetic Antimicrobial Frog Peptides Magainin 2a and PGLa", *Biochemistry* 29, (1990), 4490–4496; Rana et al. "Interactions between *Salmonella Typhimurium* Lipopolysaccharide and the Antimicrobial Peptide, Magainin 2 Amide", *FEBS Lett.* 261, (1990), 464–467; Berkowitz et al., "Magainins: A New Family of Membrane-Active Host Defense Peptides", *Biochemical Pharmacology* 39, (1990), 625–629; Duclohier, et al., "Antimicrobial Peptide Magainin 1 from *Xenopus* Skin Forms Anion-Permeable Channels in Planar Lipid Bilayers," *Biophys. J.* 56, (1989), 1017–1021. See, also, Urrutia et al., "Spontaneous Polymerization of the Antibiotic Peptide Magainin 2," *FEBS Lett.* 247, (1989), 7–21.

The published works regarding magainins and other classes of antibiotic or antimicrobial peptides (for example, cecropins, defensins, sarcotoxins, melittins, and the like) of which the inventors are aware have generally centered on human pharmaceutical-related health technologies. Exceptions, however, include two applications filed by Jaynes et al., (WO 89/04371 and WO 88/0976) which generally relate to plants which have been genetically enhanced for disease resistance. Jaynes et al. have speculated without supporting data that genetically transformed plants may be produced which contain an expressible heterologeous gene for an antimicrobial peptide. In this way, it is hoped that the plant has enhanced resistance to disease. According to Jaynes et al., however, peptides such as melittins, bombinins, and magainins having less than about 30 residues are not preferred for use in crop protection applications, presumably since the host plant cells may be adversely affected by their incorporation and/or presences.

The preferred peptides in accordance with Jaynes et al. have from about 30 to about 40 amino acids because they are more specific for bacteria and fungi. Jaynes et al. also state that peptides having more than about 40 amino acids may not be sufficiently antimicrobial when used alone to provide a broad spectrum of antimicrobial protection. The approach of Jaynes et al. for protecting plants from plant pathogens appears to center on finding specific, naturally occurring peptides having a level of activity and specificity close to that considered advantageous and then to modify that peptide to optimize its characteristics. See also, Jaynes et al., "Increasing Bacterial Disease Resistance In Plants Utilizing Antibacterial Genes from Insects," BioEssays 6, (1987), 263–270.

Others have published information relating to the incorporation of antimicrobial peptides into plants or, in fact, the use of antimicrobial peptides to protect plants from plant pathogens. See, EPO 0,299,828; P. Casteels et al., "Apidaecins: Antibacterial Peptides From Honeybees," *The EMBO J.* 8, (1989), 2387–2391; F.

Ebrahim-Nesbat et al., "Cutivar-Related Differences in the Distribution of Cell-Wall-Bound Thionins in Compatible and Incompatible Interactions Between Barley and Powdery Mildew," *Planta* 79, (1989), 203–210. However, the published information lacks a discussion regarding the various problems and solutions associated with the incorporation and/or use of such peptides with plants. It is desirable that the antimicrobial peptides of this invention are not only useful in protecting a plant from plant pathogens, but that the peptides in general are at least partially protected against plant proteases and do not significantly harm the very plant cells they are intended to protect.

Proteins produced in nature often comprise a Met amino acid bonded to the amino or N-terminal end. This is not the case with naturally occurring magainins or other naturally occurring antimicrobial peptides. Part of the present invention addresses synthesis of antimicrobial peptides with an N-terminal Met residue. Having synthesized such peptides, this invention also sets forth how such peptides are useful to protect plants from plant pathogens.

Prior to this invention, no one has considered modifying magainin based peptides such that they are both active against plant pathogens and particularly suited for use with and/or for incorporation into plants. Specifically, no one has considered the effect of naturally occurring plant enzymatic activity on antimicrobial peptides, i.e., the effect of plant proteolytic activity on the antimicrobial peptides such as those set forth in this invention; the potential deleterious effect of antimicrobial peptides on the plant cells the peptides are supposed to protect; or how such detrimental interactions can be ameliorated. Similarly, no one has squarely faced the impact of modified magainins on plant cell toxicity, also known as phytotoxity.

The present invention therefore addresses not only the need for antimicrobial peptides active against at least one plant pathogen, but also addresses the need for peptides which are specifically designed to operate in the plant kingdom. As a result of this invention, it has been determined that Magainin 1 derivatives are generally lower in phytotoxicity. Consequently, this invention shows that these derivatives are especially useful in agricultural and agronomic settings in which the peptides could be used on the plants, e.g., as a spray, or could be incorporated into a plant, e.g., genetically engineering a plant cell so that the plant cell itself produces the peptide. Further, it has been unexpectedly found that certain bonds between the amino acid constituents of magainins are sensitive to proteolytic degradation by at least one plant protease. The present inventors have also developed antimicrobial peptides which are resistant to such degradation, and have shown that changes to effect such resistance do not compromise antimicrobial activity and do not increase phytotoxicity.

OBJECTS AND SUMMARY OF THE PRESENT INVENTION

It is therefore one object of the present invention to provide for peptides which have been specifically designed to be useful for retarding plant pathogens and, more particularly, for protecting plants from plant pathogens.

It is also an object of the present invention to provide antimicrobial peptides which are resistant to degradation by plants.

It is also an object of the present invention to provide antimicrobial peptides which have antimicrobial properties and acceptable phytotoxic properties.

It is also an object of the present invention to provide antimicrobial peptides having an N-terminal Met or (f)Met amino acid.

Yet another object in accordance with the present invention is the provision of a process for retarding plant pathogens, especially to the benefit of agricultural and horticultural cultivation.

Another object in accordance with the present invention is the provision of DNA capable of expressing the aforementioned peptides, especially when the DNA is expressed in a genetically engineered cell such as a plant cell.

These and other objects will be readily apparent to those in the relevant technologies upon review hereof.

The present invention represents the culmination of the recognition and discovery of certain facts peculiar to specific antimicrobial peptides and their interaction with plant pathogens, plant cells, and/or subcellular organelles of plants. The present inventors have identified and characterized a class of antimicrobial peptides designated AMPPPs which are active against plant pathogens and useful in protecting plants from disease, infection, infestation, and other conditions deleterious to plants. The present invention is not limited in its applications to peptides which may serve to eradicate plant pathogens. The present inventors have also discovered how these AMPPPs may be rendered ineffective by the natural mechanisms of the organisms that they seek to protect and have developed ways to prevent this occurrence. The present inventors have discovered that AMPPPs, including Magainin 1 and Magainin 2, are cleaved between positions 7 and 8 ($Xaa^7$–$Xaa^8$) and also between positions 21 and 22 ($Xaa^{21}$–$Xaa^{22}$) when exposed to a plant protease. It has also been found that the cleavage of the bond between positions 7 and 8 has a most dramatic effect on the antimicrobial activity of the resulting peptide fragments. Cleavage of the bond between amino acids 21 and 22 also has a dramatic effect on the antimicrobial activity of the resulting fragments. However, when cleavage of the bond between $Xaa^7$ and $Xaa^8$ is minimized, the cleavage of the bond between $Xaa^{21}$ and $Xaa^{22}$ appears to significantly change only antibacterial activity and not antifungal activity. It has also been discovered, quite unexpectedly, that the substitution of specific amino acids at positions 7 and/or 8 can significantly reduce proteolytic sensitivity of AMPPPs. In fact, the present inventors discovered that the substitution of a lysine (Lys) or arginine (Arg) at position 7 all but eliminates proteolytic sensitivity at that site. This is particularly unexpected in view of the charge similarities between arginine, lysine, and the histidine (His) residue which normally occupies that position. The substitution of glutamic acid (Glu) at position 8 similarly all but eliminated proteolytic degradation of a so-substituted AMPPP.

It has additionally and unexpectedly been found that several of the substitutions which produce AMPPPs having increased resistance to proteolysis also resulted in AMPPPs having acceptable, or even enhanced, antifungal and/or antibacterial activity. For example, modifications such as a substitution of Arg or Lys at position 7 not only reduces the susceptibility of the peptide bond between positions 7 and 8 to plant proteolysis but also increases the resulting AMPPP's activity with regard to specific plant pathogens.

The present inventors have also determined that the addition of a Met residue at the N-terminus of AMPPPs, in general, does not substantially reduce the bioactivity thereof against specific plant pathogens. For example, addition of Met to the N-terminus of Magainin 2 or [$Ala^{13}$, $Ala^{18}$]Magainin 1 produced AMPPPs which were still significantly active against several plant pathogens.

It has also been discovered that Magainin 1 and AMPPPs based thereupon are preferred for use with plants especially for combating plant pathogens negatively effecting agronomic and horticultural plants of commercial significance. These peptides also have good resistance to degradation by plant proteases and exhibit low phytotoxicity.

Having established the aforementioned parameters, the inventors have been able to engineer antimicrobial peptides specifically adapted for use in or with plants and which evidence the necessary characteristics of resistance to plant degradation, e.g., proteolysis, significant antimicrobial activity, and sufficiently low phytotoxicity. The engineered AMPPPs of this invention are useful for protecting plants from plant pathogens by conventional application technology. These AMPPPs will be far more successful when genes which can express these peptides are inserted and incorporated into the genome of a plant such that the peptide is expressed in the plant and in subsequent generations thereof.

In accordance with the above objects, there is provided a composition of matter which is a Magainin 1 substitution derivative and which has the amino acid sequence Gly—Ile—Gly—Lys—Phe—Xaa—Xaa—Xaa—Ala—Xaa—Xaa—

Phe—Xaa—Lys—Ala—Phe—Val—Xaa—Xaa—Ile—Xaa—Lys—

Xaa wherein $Xaa^6$, $Xaa^7$, $Xaa^8$, $Xaa^{11}$, $Xaa^{13}$, $Xaa^{18}$, $Xaa^{19}$, $Xaa^{21}$ and $Xaa^{23}$, may be the same or different and are selected from the group consisting of Ala, Arg, Orn, Asn, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val, and wherein $Xaa^{10}$ is selected from the group consisting of Ala, Arg, Orn, Asn, Asp, Gln, Glu, Gly, His, Ile, Leu, Lys, Met, Phe, Ser, Thr, Trp, Tyr, 3,4-dihydroxyphenylalanine, and Val, with the proviso that the AMPPP is not Magainin 1. With regard thereto, "not Magainin 1" is understood to mean that the compositions in accordance herewith are not inclusive of an unsubstituted Magainin 1 peptide.

Compounds in accordance with this aspect of the present invention are generally useful against one or more type of plant pathogen. These AMPPPs may additionally have increased resistance to proteolytic degradation when compared to, at least, Magainin 1 and are designed to have acceptable phytotoxicity, most particularly so in conjunction with agricultural uses of such compounds.

In accordance with another aspect of the present invention, there is provided a composition of matter which is a Magainin 2 substitution derivative and which has the amino acid sequence Gly—Ile—Gly—Lys—Phe—Xaa—Xaa—Xaa—Ala—Xaa—Xaa—

-continued

Phe—Xaa—Lys—Ala—Phe—Val—Xaa—Xaa—Ile—Xaa—Asn—

Xaa wherein $Xaa^6$, $Xaa^7$, $Xaa^8$, $Xaa^{11}$, $Xaa^{13}$, $Xaa^{18}$, Xaa19, $Xaa^{21}$ and $Xaa^{23}$ may be the same or different and are selected from the group consisting of Ala, Arg, Orn, Asn, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val, and wherein $Xaa^{10}$ is selected from the group consisting of Ala, Arg, Orn, Asn, Asp, Gln, Glu, Gly, His, Ile, Leu, Lys, Met, Phe, Ser, Thr, Trp, Tyr, 3,4-dihydroxyphenylalanine and Val with the proviso that the AMPPP is not Magainin 2, Magainin 2 substituted only at $Xaa^{21}$, Magainin 2 substituted only in at least two of $Xaa^8$, $Xaa^{13}$ and $Xaa^{18}$ with Ala and with the further proviso that the AMPPP is not Magainin 2 substituted with only a single Ala.

These AMPPPs, which are substitution derivatives of Magainin 2, like their Magainin 1 counterparts, have the benefit of either specific or broad spectrum antimicrobial/antibiotic activity against plant pathogens. Many also have increased resistance to proteolytic degradation and/or do not have increased phytotoxicity when compared to their Magainin 2 counterparts.

Particularly preferred AMPPPs in accordance with the foregoing discussion are the Magainin 1 or Magainin 2 substitution derivatives previously described, wherein $Xaa^6$ is an amino acid selected from the group consisting of Asn, Pro, 3Hyp, 4Hyp, Ile, and Leu; $Xaa^7$ is an amino acid selected from the group consisting of Phe, Ala, Met, Ser, Thr, Trp, Tyr, 3,4-dihydroxyphenylalanine, Gln, Pro, 3Hyp, 4Hyp, Lys, Asn, Glu, His, Asp, Orn, and Arg, $Xaa^8$ is an amino acid selected from the group consisting of Ala, Met, Pro, 3Hyp, 4Hyp, Thr, Ser, Trp, Tyr, 3,4-dihydroxyphenylalanine, Gln, Lys, Asn, Glu, His, Asp, Orn, and Arg, $Xaa^{10}$ is an amino acid selected from the group consisting of Gly, Leu, Ile, Val, Ala, Phe, Met, Thr, Ser, Trp, Tyr, 3,4-dihydroxyphenylalanine, Gln, Lys, Asn, Glu, His, Asp, Orn, and Arg, $Xaa^{11}$ is an amino acid selected from the group consisting of Met, Trp, Tyr, 3,4-dihydroxyphenylalanine, Gln, Lys, His, Pro, 3Hyp, 4Hyp, Ser, Orn, and Arg, $Xaa^{13}$ is an amino acid selected from the group consisting of Leu, Ile, Trp, Phe, Val, Ala, Gly, Pro, 3Hyp, and 4Hyp, $Xaa^{18}$ is an amino acid selected from the group consisting of Thr, Trp, Tyr, Asp, Glu, Lys, Arg, Gln, His, Met, Ala, Gly, Pro, 3Hyp, and 4Hyp, $Xaa^{19}$ is an amino acid selected from the group consisting of Ala, Glu, Pro, 3Hyp, and 4Hyp, and $Xaa^{21}$ and $Xaa^{23}$ may be the same or different and are selected from the group consisting of Arg, Orn, Asp, His, Glu, Lys, Gln, Tyr, Thr, 3,4-dihydroxyphenylalanine, Trp, Met, Asn, Ser, Ala, Phe, Val, Ile, Leu, Pro, 3Hyp and 4Hyp.

More preferred AMPPPs in accordance with the previously described substitution derivatives include those having an amino acid sequence wherein $Xaa^6$ is Leu, $Xaa^7$ is an amino acid selected from the group consisting of Phe, Ala, Met, Ser, Asp, Glu, Thr, Tyr, Gln, Lys, His and Arg, $Xaa^8$ is an amino acid selected from the group consisting of Ser, Ala, Met, Thr, Trp, Tyr, Gln, Lys, Asn, Glu, His, Asp and Arg, $Xaa^{10}$ is an amino acid selected from the group consisting of Gly, Leu, Val, Ala, Met, Thr, Ser, Trp, Tyr, Gln, Lys, Asn, Glu, His, Asp and Arg, $Xaa^{11}$ is an amino acid selected from the group consisting of Met, Trp, Tyr, Gln, Lys, His, Ser, and Arg, $Xaa^{13}$ is an amino acid selected from the group consisting of Ala, Gly, Leu, Ile, Trp, Phe, and Val, $Xaa^{18}$ is an amino acid selected from the group consisting of Ala, Gly, Thr, Trp, Tyr, Asp, Glu, Lys, Arg, Gln, His and Met, $Xaa^{19}$ is an amino acid selected from the group consisting of Ala and Glu, $Xaa^{21}$ is an amino acid selected from the group consisting of Arg, Asp, His, Glu, Lys, Gln, Tyr, Thr, Trp, Met, and Ala, and $Xaa^{23}$ is an amino acid selected from the group consisting of Ser, Thr, Val, Ala, Leu, Ile, Trp, Phe, His, Gln, and Tyr.

Of course, the preferred and more preferred AMPPPs just described are subject to the same provisos as previously articulated.

In another preferred embodiment in accordance with this aspect of the present invention, AMPPPs are provided which are substitution derivatives of Magainin 1 or Magainin 2 and which are designed to be especially resistant to plant proteolysis. These substitution derivatives generally include at least one substitution at $Xaa^7$, $Xaa^8$, and/or $Xaa^{21}$. More preferably, $Xaa^7$ is an amino acid selected from the group consisting of Phe, Ala, His, Lys, Ser, Glu, Asp, and Arg, $Xaa^8$ is an amino acid selected from the group consisting of Thr, Ser, Ala, His, Asp, and Glu, and/or $Xaa^{21}$ is an amino acid selected from the group consisting of Arg, Lys, His, Gln, Trp, Tyr, Thr, Val, Ala, Leu, Ile, Glu, Asp, Phe, and Met.

In accordance with another aspect of the present invention, there is provided a composition of matter which is neither a substitution derivative of Magainin 1 nor a substitution derivative of Magainin 2. These AMPPPs generally have the amino acid sequence Gly—Ile—Gly—Lys—Phe—Xaa—Xaa—Xaa—Ala—Xaa—Xaa—

Phe—Xaa—Lys—Ala—Phe—Val—Xaa—Xaa—Ile—Xaa—Xaa—

Xaa wherein $Xaa^6$, $Xaa^7$, $Xaa^8$, $Xaa^{11}$, $Xaa^{13}$, $Xaa^{18}$, $Xaa^{19}$, $Xaa^{21}$, $Xaa^{22}$, and $Xaa^{23}$ may be the same or different and are selected from the group consisting of Ala, Arg, Orn, Ash, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val, and wherein $Xaa^{10}$ is selected from the group consisting of Ala, Arg, Orn, Asn, Asp, Gln, Glu, Gly, His, Ile, Leu, Lys, Met, Phe, Ser, Thr, Trp, Tyr, 3,4-dihydroxyphenylalanine and Val and wherein when $Xaa^{22}$ is Lys, $Xaa^{10}$ may not be Gly and when $Xaa^{22}$ is Asn, $Xaa^{10}$ may not be Lys.

AMPPPs in accordance with this aspect of the present invention are similar in structure to Magainin 1, Magainin 2, and the substitution derivatives thereof previously described. These AMPPPs also have either specific or broad spectrum activity against plant pathogens, and may also have increased resistance to plant proteolysis and/or may not have substantially increased phytotoxicity.

In accordance with yet another aspect of the present invention, AMPPPs are provided which include an amino acid selected from the group consisting of Met and N-formylated Met, "(f)Met," bound through a peptide bond to the N-terminus of a peptide selected from the group consisting of an AMPPP, wherein one or more amino acids thereof are substituted with an amino acid selected from the group consisting of Ala, Arg, Orn, Asn, Asp, Gln, Glu, Gly, His, Ile, Leu, Lys, Met, Phe, Ser, Thr, Trp, Tyr, 3,4-dihydroxyphenylalanine and Val and wherein any amino acid other than the amino acid at position 10 of the AMPPP may additionally be substituted with an amino acid selected from the group consisting of Pro, 3Hyp and 4Hyp.

In accordance with a more preferred aspect of the above-described invention, AMPPPs have Met or (f)Met appended to the N-terminus of the amino acid sequence Gly—Ile—Gly—Lys—Phe—Xaa—Xaa—Xaa—Ala—Xaa—Xaa—

Phe—Xaa—Lys—Ala—Phe—Val—Xaa—Xaa—Ile—Xaa—Xaa—

Xaa wherein $Xaa^6$, $Xaa^7$, $Xaa^8$, $Xaa^{11}$, $Xaa^{13}$, $Xaa^{18}$, $Xaa^{19}$, $Xaa^{21}$, $Xaa^{22}$, and $Xaa^{23}$ may be the same or different and are selected from the group consisting of Ala, Arg, Orn, Asn, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val, and wherein $Xaa^{10}$ is selected from the group consisting of Ala, Arg, Orn, Asn, Asp, Gln, Glu, Gly, His, Ile, Leu, Lys, Met, Phe, Ser, Thr, Trp, Tyr, 3,4-dihydroxyphenylalanine and Val.

These Met-AMPPPs and (f)Met-AMPPPs are useful in retarding plant pathogens in as much as it has been found that these peptides retain specific and/or broad spectrum activity against plant pathogens, despite the Met or (f)Met extension. These peptides may additionally possess decreased proteolytic sensitivity to plant proteases and/or do not possess increased phytotoxicity. These peptides may also be particularly useful for incorporation within plant or bacterial cells and for genetic expression in cells generally.

In accordance with another aspect of the present invention, there are provided single residue omission derivatives of an AMPPP having the amino acid sequence Gly—Ile—Gly—Lys—Phe—Xaa—Xaa—Xaa—Ala—Xaa—Xaa—

Phe—Xaa—Lys—Ala—Phe—Val—Xaa—Xaa—Ile—Xaa—Xaa—

Xaa wherein $Xaa^6$, $Xaa^7$, $Xaa^8$, $Xaa^{11}$, $Xaa^{13}$, $Xaa^{18}$, $Xaa^{19}$, $Xaa^{21}$, $Xaa^{22}$, and $Xaa^{23}$ may be the same or different and are selected from the group consisting of Ala, Arg, Orn, Asn, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val, and wherein $Xaa^{10}$ is selected from the group consisting of Ala, Arg, Orn, Asn, Asp, Gln, Glu, Gly, His, Ile, Leu, Lys, Met, Phe, Ser, Thr, Trp, Tyr, 3,4-dihydroxyphenylalanine and Val and wherein when $Xaa^{22}$ is Lys, $Xaa^{10}$ may not be Gly and when $Xaa^{22}$ is Asn, $Xaa^{10}$ may not be Lys.

Other peptides in accordance with a related aspect of the present invention include double residue omission derivatives of an AMPPP having the amino acid sequence Gly—Ile—Gly—Lys—Phe—Xaa—Xaa—Xaa—Ala—Xaa—Xaa—

Phe—Xaa—Lys—Ala—Phe—Val—Xaa—Xaa—Ile—Xaa—Xaa—

Xaa wherein $Xaa^6$, $Xaa^7$, $Xaa^8$, $Xaa^{11}$, $Xaa^{13}$, $Xaa^{18}$, Xaa19, $Xaa^{21}$, $Xaa^{22}$, and $Xaa^{23}$ may be the same or different and are selected from the group consisting of Ala, Arg, Orn, Asn, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val, and wherein $Xaa^{10}$ is selected from the group consisting of Ala, Arg, Orn, Asn, Asp, Gln, Glu, Gly, His, Ile, Leu, Lys, Met, Phe, Ser, Thr, Trp, Tyr, 3,4-dihydroxyphenylalanine and Val and wherein when $Xaa^{22}$ is Asn, $Xaa^{10}$ may not be Lys.

These single and double residue omission derivatives may further include an amino acid selected from the group consisting of Met and (f)Met, bound through a peptide bond to the N-terminus thereof.

In accordance with another aspect of the present invention, there is provided a composition of matter comprising a peptide selected from the group consisting of single residue omission derivatives of a peptide having a sequence Gly-Ile-Gly-Lys-Phe-Xaa-Xaa-Xaa-Ala-Gly-Xaa-Phe-Xaa-Lys-Ala-Phe-Val-Xaa-Xaa-Ile-Xaa-Lys-Xaa, double residue omission derivative of a peptide having a sequence Gly-Ile-Gly-Lys-Phe-Xaa-Xaa-Xaa-Ala-Gly-Xaa-Phe-Xaa-Lys-Ala-Phe-Val-Xaa-Xaa-Ile-Xaa-Lys-Xaa, single residue omission derivatives of a peptide having a sequence Gly-Ile-Gly-Lys-Phe-Xaa-Xaa-Xaa-Ala-Lys-Xaa-Phe-Xaa-Lys-Ala-Phe-Val-Xaa-Xaa-Ile-Xaa-Asn-Xaa, and double residue omission derivatives of a peptide having a sequence Gly-Ile-Gly-Lys-Phe-Xaa-Xaa-Xaa-Ala-Lys-Xaa-Phe-Xaa-Lys-Ala-Phe-Val-Xaa-Xaa-Ile-Xaa-Asn-Xaa, wherein $Xaa^6$, $Xaa^7$, $Xaa^8$, $Xaa^{11}$, $Xaa^{13}$, $Xaa^{18}$, $Xaa^{21}$, $Xaa^{23}$ may be the same or different and may be selected from the group consisting of Ala, Arg, Orn, Asn, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val with the proviso that at least one non-omitted position is substituted.

These single and double residue omission AMPPPs may also include an amino acid selected from the group consisting of Met and (f)Met bound to the N-terminus thereof through a peptide bond. The phrase "at lease one non-omitted position is substituted" is intended to describe AMPPPs in accordance with the present invention which when compared to Magainin 1 and/or Magainin 2 include at least one substitution in addition to a single or double residue omission. These peptides would include [$Arg^7$, Des $Lys^{22}$, Des $Ser^{23}$]Mag 1, [Des $Gly^1$, $Glu^8$, Des $Ser^{23}$]Mag 1 and/or [$Ala^{13}$, $Ala^{18}$, Des $Met^{21}$]Mag 1 (Mag 1=Magainin 1). With regard to the AMPPPs in accordance with this aspect of the present invention, at least one substitution must persist, even after omissions are made.

The AMPPPS previously described which are neither Magainin 1 nor Magainin 2 preferably include a sequence as provided herein wherein $Xaa^{22}$ is an amino acid selected from the group consisting of Arg, Orn, Asp, His, Glu, Lys, Gln, Tyr, 3,4-dihydroxyphenylalanine, Trp, Met, Asn, Ala, Pro, Ile, 3Hyp, Ser, Thr, and 4Hyp, and wherein $Xaa^6$ is an amino acid selected from the group consisting of Asn, Pro, 3Hyp, 4Hyp, Ile, and Leu, $Xaa^7$ is an amino acid selected from the group consisting of Phe, Ala, Met, Ser, Thr, Trp, Tyr, 3,4-dihydroxyphenylalanine, Gln, Pro, 3Hyp, 4Hyp, Lys, Asn, Glu, His, Asp, Orn, and Arg, $Xaa^8$ is an amino acid selected from the group consisting of Ala, Met, Pro, 3Hyp, 4Hyp, Thr, Ser, Trp, Tyr, 3,4-dihydroxyphenylalanine, Gln, Lys, Asn, Glu, His, Asp, Orn, and Arg, $Xaa^{10}$ is an amino acid selected from the group consisting of Gly, Leu, Ile, Val, Ala, Phe, Met, Thr, Ser, Trp, Tyr, 3,4-dihydroxyphenylalanine, Gln, Lys, Asn, Glu, His, Asp, Orn, and Arg, $Xaa^{11}$ is an amino acid selected from the group consisting of Met, Trp, Tyr, 3,4-dihydroxyphenylalanine, Gln, Lys, His, Pro, 3Hyp, 4Hyp, Ser, Orn, and Arg, $Xaa^{13}$ is an amino acid selected from the group consisting of Leu, Ile, Trp, Phe, Val, Ala, Gly, Pro, 3Hyp, and 4Hyp, $Xaa^{18}$ is an amino acid selected from the group consisting of Thr, Trp, Tyr, Asp, Glu, Lys, Arg, Gln, His, Met, Ala, Gly, Pro, 3Hyp, and 4Hyp, $Xaa^{19}$ is an amino acid selected from the group consisting of Ala, Glu, Pro, 3Hyp, and 4Hyp, and $Xaa^{21}$ and $Xaa^{23}$ may be the same or different and are selected from the group consisting of Arg, Orn, Asp, His, Glu, Lys, Gln, Tyr, Thr, 3,4-dihydroxyphenylalanine, Trp, Met, Asn, Ser, Ala, Phe, Val, Ile, Leu, Pro, 3Hyp and 4Hyp.

In a more preferred aspect of the present invention, AMPPPs which are neither Magainin 1 nor Magainin 2 preferably have a sequence wherein $Xaa^{22}$ is an amino acid selected from the group consisting of Ile, Asn, Arg, Asp, His, Glu, Lys, Gln, Tyr, Thr, Trp, Met, and Ala, $Xaa^6$ is Leu, $Xaa^7$ is an amino acid selected from the group consisting of Phe, Ala, Met, Thr, Tyr, Gln, Lys, His, Asp, Glu, Ser, and Arg, $Xaa^8$ is an amino acid selected from the group consisting of Ser, Ala, Met, Thr, Trp, Tyr, Gln, Lys, Asn, Glu, His, Asp and Arg, $Xaa^{10}$ is an amino acid selected from the group consisting of Gly, Leu, Val, Ala, Met, Thr, Ser, Trp, Tyr, Gln, Lys, Asn, Glu, His, Asp and Arg, $Xaa^{11}$ is an amino acid selected from the group consisting of Met, Trp, Tyr, Gln, Lys, His, Ser, and Arg, $Xaa^{13}$ is an amino acid selected from the group consisting of Ala, Gly, Leu, Ile, Trp, Phe, and Val, $Xaa^{18}$ is an amino acid selected from the group consisting of Ala, Gly, Thr, Trp, Tyr, Asp, Glu, Lys, Arg, Gln, His and Met, $Xaa^{19}$ is an amino acid selected from the group consisting of Ala and Glu, $Xaa^{21}$ is an amino acid selected from the group consisting of Arg, Asp, His, Glu, Lys, Gln, Tyr, Thr, Trp, Met, and Ala, and $Xaa^{23}$ is an amino acid selected from the group consisting of Ser, Thr, Val, Ala, Leu, Ile, Trp, Phe, Pro, 3Hyp, 4Hyp, His, Gln and Tyr.

In another preferred aspect of the present invention, these AMPPPs including the single and double residue omission derivatives, the Met and (f)Met AMPPPs, and the non-Magainin 1, non-Magainin 2 AMPPPs described above, preferably have an increased resistance to degradation by one or more plant proteases. These more preferred AMPPPs generally include at least one substitution at $Xaa^7$, $Xaa^8$, $Xaa^{21}$ and/or $Xaa^{22}$. More preferably, $Xaa^7$ is an amino acid selected from the group consisting of Phe, Ala, His, Lys, Orn, and Arg, $Xaa^8$ is an amino acid selected from the group consisting of Thr, Ser, Ala and Glu, $Xaa^{21}$ is an amino acid selected from the group consisting of Arg, Lys, His, Gln, Trp, Tyr, Thr, Ala, Leu, Ile, Val, Phe, and Met, and $Xaa^{22}$ is an amino acid selected from the group consisting of Arg, Lys, His, Gln, Trp, Tyr, Ser, 3,4-dihydroxyphenylalanine, Thr, Pro, 3Hyp, 4Hyp, Val, Ala, Glu, Asp, Phe, Ile, Leu, and Met.

There are also provided peptides, in accordance with one aspect of the present invention, which include an amino acid selected from the group consisting of Met and (f)Met, bound through a peptide bond to the N-terminus of a peptide selected from the group consisting of single residue omission derivatives of a peptide having a sequence Gly-Ile-Gly-Lys-Phe-Xaa-Xaa-Xaa-Ala-Gly-Xaa-Phe-Xaa-Lys-Ala-Phe-Val-Xaa-Xaa-Ile-Xaa-Lys-Xaa, double residue omission derivative of a peptide having a sequence Gly-Ile-Gly-Lys-Phe-Xaa-Xaa-Xaa-Ala-Gly-Xaa-Phe-Xaa-Lys-Ala-Phe-Val-Xaa-Xaa-Ile-Xaa-Lys-Xaa, single residue omission derivatives of a peptide having a sequence Gly-Ile-Gly-Lys-Phe-Xaa-Xaa-Xaa-Ala-Lys-Xaa-Phe-Xaa-Lys-Ala-Phe-Val-Xaa-Xaa-Ile-Xaa-Asn-Xaa, and double residue omission derivatives of a peptide having a sequence Gly-Ile-Gly-Lys-Phe-Xaa-Xaa-Xaa-Ala-Lys-Xaa-Phe-Xaa-Lys-Ala-Phe-Val-Xaa-Xaa-Ile-Xaa-Asn-Xaa, wherein $Xaa^{6}$, $Xaa^{7}$, $Xaa^{8}$, $Xaa^{11}$, $Xaa^{13}$, $Xaa^{18}$, $Xaa^{19}$, $Xaa^{21}$, $Xaa^{23}$ may be the same or different and may be selected from the group consisting of Ala, Arg, Orn, Asn, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val.

In accordance with another aspect of the present invention, an AMPPP composition is provided comprising a peptide having between about 18 and about 23 amino acid residues, the peptide being substituted such that it is resistant to degradation by at least one plant protease.

More specifically, a composition of matter is provided including a peptide having between about 18 and about 23 amino acid residues, said peptide being a derivative of a peptide having the amino acid sequence Gly—Ile—Gly—Lys—Phe—Xaa—Xaa—Xaa—Ala—Xaa—Xaa—

Phe—Xaa—Lys—Ala—Phe—Val—Xaa—Xaa—Ile—Xaa—Xaa—

Xaa wherein $Xaa^{6}$, $Xaa^{7}$, $Xaa^{8}$, $Xaa^{11}$, $Xaa^{13}$, $Xaa^{18}$, $Xaa^{19}$, $Xaa^{21}$, $Xaa^{22}$, and $Xaa^{23}$, may be the same or different and are selected from the group consisting of: Ala, Arg, Orn, Asn, Asp, Gln, Glu, Gly, His, Ile, Leu, Lys, Met, Phe, Pro, 3Hyp, 4Hyp, Ser, Thr, Trp, Tyr, 3,4-dihydroxyphenylalanine and Val, and wherein $Xaa^{10}$ is selected from the group consisting of Ala, Arg, Orn, Asn, Asp, Gln, Glu, Gly, His, Ile, Leu, Lys, Met, Phe, Ser, Thr, Trp, Tyr, 3,4-dihydroxyphenylalanine and Val, the peptide being substituted such that it is resistant to proteolytic degradation by at least one plant protease.

Another preferred aspect of the present invention is the provision of an oligonucleotide whose nucleotide sequence is specifically selected to encode or express any of the AMPPPs previously described.

For example, Magainin 1 substitution derivatives can be expressed from an oligonucleotide having the nucleotide sequence

```
GGNATHGGNA ARTTYNNNNN NNNNGCNNNN NNNTTYNNNA   40
ARGCNTTYGT NNNNNNNATH NNNAARNNN               69
```

where C is a nucleotide including the base cytosine, A is a nucleotide including the base adenine, G is a nucleotide including the base guanine, T is a nucleotide including the base thymine, H is a variable which is a nucleotide including the base adenine, cytosine, or thymine but not guanine, R is a variable which is a nucleotide including the base adenine or guanine, Y is a variable which is a nucleotide including the base cytosine or thymine, and N is a variable which is a nucleotide including the base adenine, cytosine, guanine or thymine, and wherein N16–N18, N19–N21, N22–N24, N31–N33, N37–N39, N52–N54, N55–N57, N61–N63, and N67–N69 cooperate to code for an amino acid which may be the same or different and are selected from the group consisting of Ala, Arg, Asn, Asp, Gln, Glu, Gly, His, Ile, Leu, Lys, Met, Phe, Pro, Ser, Thr, Trp, Tyr, and Val, and wherein N28–N30 cooperate to code for an amino acid selected from the group consisting of Ala, Arg, Asn, Asp, Gln, Glu, Gly, His, Ile, Leu, Lys, Met, Phe, Ser, Thr, Trp, Tyr, and Val with the proviso that said oligonucleotide may not code for Magainin 1.

Magainin 2 substitution derivatives can be expressed from an oligonucleotide having the nucleotide sequence

```
GGNATHGGNA ARTTYNNNNN NNNNGCNNNN NNNTTYNNNA   40
ARGCNTTYGT NNNNNNNATH NNNAAYNNN               69
```

wherein N16–N18, N19–N21, N22–N24, N31–N33, N37–N39, N52–N54, N55–N57, N61–N63 and N67–N69 cooperate to code for an amino acid which may be the same or different and are selected from the group consisting of Ala, Arg, Asn, Asp, Gln, Glu, Gly, His, Ile, Leu, Lys, Met, Phe, Pro, Ser, Thr, Trp, Tyr, and Val, and wherein N28–N30 cooperate to code for an amino acid selected from the group consisting of Ala, Arg, Asn, Asp, Gln, Glu, Gly, His, Ile, Leu, Lys, Met, Phe, Ser, Thr, Trp, Tyr, and Val, with the provisos that said oligonucleotide may not code for Magainin 2, Magainin 2 substituted only at position 21, Magainin 2 substituted only in at least two of positions 8, 13 or 18 with Ala, and with the further proviso that said peptide is not Magainin 2 substituted with only a single Ala.

Similarly, AMPPPs which are not Magainin 1 or Magainin 2, as previously described, can be expressed by an oligonucleotide having the nucleotide sequence

```
GGNATHGGNA ARTTYNNNNN NNNNGCNNNN NNNTTYNNNA   40
ARGCNTTYGT NNNNNNNATH NNNNNNNNN               69
```

wherein N16–N18, N19–N21, N22–N24, N31–N33, N37–N39, N52–N54, N55–N57, N61–N63, N64–N66, N67–N69 cooperate to code for an amino acid which may be the same or different and are selected from the group consisting of Ala, Arg, Asn, Asp, Gln, Glu, Gly, His, Ile, Leu, Lys, N28–N30 cooperate to code for an amino acid selected from the group consisting of Ala, Arg, Asn, Asp, Gln, Glu, Gly, His, Ile, Leu, Lys, Met, Phe, Ser, Thr, Trp, Tyr, and Val with the proviso that when N64–N66 cooperate to code for the amino acid Lys, N28–N30 may not cooperate to code for the amino acid Gly and when N64–N66 cooperate to code for the amino acid Asn, N28–N30 may not cooperate to code for the amino acid Lys.

Met and (f)Met AMPPPs in accordance with the present invention may be expressed by a first plurality of nucleotides whose nucleotide sequence is ATG and which cooperate to code for an amino acid selected from the group consisting of Met and (f)Met, the first plurality of nucleotides being bound through a phosphodiester bond to a second plurality of nucleotides which cooperate to code for an AMPPP, wherein one or more amino acids thereof are substituted with an amino acid selected from the group consisting of Ala, Arg, Asn, Asp, Gln, Glu, Gly, His, Ile, Leu, Lys, Met, Phe, Ser, Thr, Trp, Tyr, and Val and wherein any amino acid other than the amino acid at position 10 of said substitution derivatives of Magainin 1 or Magainin 2 may additionally be substituted with Pro.

Single residue omission derivatives of AMPPPs in accordance with the present invention are expressed by a trinucleotide omission derivative of an oligonucleotide having the nucleotide sequence

GGNATHGGNA ARTTYNNNNN NNNNGCNNNN NNNTTYNNNA 40

ARGCNTTYGT NNNNNNNATH NNNNNNNNN 69 wherein N16-N18, N19-N21, N22-N24, N31-N33, N37-N39, N52-N54, N55-N57, N61-N63, N64-N66, N67-N69 cooperate to code for an amino acid which are the same or different and may be selected from the group consisting of Ala, Arg, Asn, Asp, Gln, Glu, Gly, His, Ile, Leu, Lys, Met, Phe, Pro, Ser, Thr, Trp, Tyr, and Val, and wherein N28-N30 cooperate to code for an amino acid selected from the group consisting of Ala, Arg, Asn, Asp, Gln, Glu, Gly, His, Ile, Leu, Lys, Met, Phe, Ser, Thr, Trp, Tyr, and Val and with the proviso that when N64-N66 cooperate to code for the amino acid Lys, N28-N30 may not cooperate to code for the amino acid Gly and when N64-N66 cooperate to code for the amino acid Asn, N28-N30 may not cooperate to code for the amino acid Lys.

Double residue omission derivatives of AMPPPs, in accordance with the present invention, are expressed by a six-nucleotide omission derivative of an oligonucleotide having the nucleotide sequence

GGNATHGGNA ARTTYNNNNN NNNNGCNNNN NNNTTYNNNA 40

ARGCNTTYGT NNNNNNNATH NNNNNNNNN 69 wherein N16-N18, N19-N21, N22-N24, N31-N33, N37-N39, N52-N54, N55-N57, N61-N63, N64-N66, N67-N69 cooperate to code for an amino acid which may be the same or different and are selected from the group consisting of Ala, Arg, Asn, Asp, Gln, Glu, Gly, His, Ile, Leu, Lys, Met, Phe, Pro, Ser, Thr, Trp, Tyr, and Val, and wherein N28-N30 cooperate to code for an amino acid selected from the group consisting of Ala, Arg, Asn, Asp, Gln, Glu, Gly, His, Ile, Leu, Lys, Met, Phe, Ser, Thr, Trp, Tyr, and Val and with the proviso that when N64-N66 cooperate to code for the amino acid Asn, N28-N30 may not cooperate to code for the amino acid Lys.

The (f)Met and Met derivatives of the aforementioned peptides may also be expressed by the addition to the aforementioned oligonucleotides of a plurality of nucleotides whose nucleotide sequence is ATG which cooperate to code for Met or (f)Met linked by a phosphodiester bond to the oligonucleotide. Similarly, in accordance with the present invention, the Met and (f)Met extensions of the single and double residue omission derivatives of AMPPPs may also be expressed from a corresponding trinucleotide omission derivative or a six-nucleotide omission derivative of an oligonucleotide having the nucleotide sequence

GGNATHGGNA ARTTYNNNNN NNNNGCNNNN NNNTTYNNNA 40

ARGCNTTYGT NNNNNNNATH NNNNNNNNN 69 wherein N16-N18, N19-N21, N22-N24, N31-N33, N37-N39, N52-N54, N55-N57 N61-N63 and N67-N69 may cooperate to code for an amino acid which may be the same or different and said amino acid is selected from the group consisting of Ala, Arg, Asn, Asp, Glu, Glu, Gly, His, Ile, Leu, Lys, Met, Phe, Pro, Ser, Thr, Trp, Tyr, and Val, and wherein N28-N30 cooperate to code for an amino acid selected from the group consisting of Gly and Lys and N64-N66 cooperate to code for an amino acid selected from the group consisting of Lys and Asn.

In accordance with yet another aspect of the present invention, there is provided a process for retarding the survival or growth of plant pathogens which includes the steps of providing at least one AMPPP in accordance with the present invention, or mixtures of a plurality of such AMPPPs, in an amount effective to retard the survival or growth of at least one plant pathogen, and contacting the pathogen therewith. By the term "amount effective to retard at least one plant pathogen," it is understood that although the effective amount is likely to be influenced by the method of application, it is expected that the effective amount would normally be in the range 1-100 micrograms/mL.

In accordance with another aspect of the present invention there is provided hereby a biological screening reagent useful for determining the resistance of a compound to proteolytic degradation comprising at least one plant protease in an amount effective to cause at least 50% degradation of said compound in about five hours. These proteolytic solutions are designed to closely resemble the protease-containing environment within the extracellular space of a plant cell. Therefore, the reagent may be used to provide a more accurate estimation of the relative proteolytic sensitivity of a specific peptide in vivo. The reagent may also simulate the proteolytic activity of plant pathogens and may be used to treat AMPPPs to determine the degree of their degradation.

A process of making these reagents from cells contained within a liquid culture medium in accordance with the present invention is also provided and includes the steps of separating cells from a liquid culture medium and collecting said medium containing at least one extracellular plant protease. This process has several advantages. Most important, however, is the fact that this process may be used to obtain not only the extracellular proteases containing solutions from plant cells, but also the extracellular proteases containing solutions from plant pathogens such as fungi and bacteria.

This aspect of the present invention also includes the use of the above-described reagent to determine a compound's resistance to degradation by at least one plant protease. This method includes the steps of providing a source of a compound to be screened, incubating the compound with the biological screening reagent of the present invention having between about 0.05 parts per million to about one part per thousand of at least one protease in water, for a predetermined time, stopping said reaction by inactivating said reagent, and analyzing the resulting compounds.

DETAILED DESCRIPTION OF THE PREFERRED EMBODIMENTS

"AMPPP" is an acronym for antimicrobial peptide active against plant pathogens, which, as defined, herein, is a protein or peptide having at least antifungal and/or antibacterial activity. While the term may have broader application to one or more entire families of antimicrobial peptides, as used herein the term AMPPP encompasses Magainin 1, Magainin 2, and magainin derivative compositions preferably having between 18 and 24 amino acids. Generally, AMPPPs in accordance with the present invention have the sequence Gly—Ile—Gly—Lys—Phe—Xaa—Xaa—Xaa—Ala—Xaa—Xaa— (I)

Phe—Xaa—Lys—Ala—Phe—Val—Xaa—Xaa—Ile—Xaa—Lys—

Xaa

"Xaa" as used in the above sequence indicates a variable such that any of a select group of amino acids can be positioned therein. Furthermore, "$Xaa^n$" is used to represent not only the variable, but also to describe the relative position of that variable or the amino acids which that variable represents (i.e., "n" represents the position, or the amino acid at the nth position). Thus, $Xaa^6$ represents the variable in the 6th position of the AMPPP having the sequence (I). The "n"th position is relative to the N-terminal end of the peptide which is usually glycine (Gly). When the aforementioned peptide of sequence (I) further includes a methionine (Met) or N-formylated Met, "(f)Met," attached through a peptide bond to the N-terminal glycine, the variable $Xaa^6$ retains its nomenclature and its position relative to the N-terminal glycine. Similarly, if the N-terminal glycine were omitted, such that the variable $Xaa^6$ was the 5th residue in the resulting peptide, it will nonetheless remain designated $Xaa^6$. (IleGlyLysPheXaa . . . , Xaa is still $Xaa^6$) When placed in such terms, Magainin 1 is a specific AMPPP wherein $Xaa^6$ is leucine (Leu), $Xaa^7$ is histidine (His), $Xaa^8$ is serine (Ser), $Xaa^{10}$ is glycine (Gly), $Xaa^{11}$ is lysine (Lys), $Xaa^{13}$ and $Xaa^{18}$ are glycine (Gly), $Xaa^{19}$ is glutamic acid (Glu), $Xaa^{21}$ is methionine (Met), $Xaa^{22}$ is lysine (Lys) and $Xaa^{23}$ is serine (Ser). Magainin 2 is structurally similar to Magainin 1 except that $Xaa^{10}$ is lysine(Lys) and $Xaa^{22}$ is asparagine (Asn).

Similarly, the present invention includes the deoxyribonucleic acids and/or ribonucleic acids (DNA and/or RNA) which are oligonucleotides capable of expressing the AMPPPs of the present invention and which contain a nucleotide sequence of

```
GGNATHGGNA ARTTYNNNNN NNNNGCNNNN NNNTTYNNNA   40   (II)
ARGCNTTYGT NNNNNNNATH NNNNNNNNN               69
```

If RNA is the oligonucleotide in question, T represents the pyrimidine base uracil. As is well known, oligonucleotides such as DNA are read in codons, or groups of three. That is, it is the combination of the information contained in three adjacent nucleotides which determine the type of amino acid which will be incorporated in the specific and corresponding position of the encoded peptide. For example, the codon GGN, which includes the first three nucleotides of oligonucleotide sequence II, codes for the amino acid Gly which is the N-terminal amino acid of the peptides in accordance with the present invention. Therefore, it should be understood that groups of three nucleotides cooperate to code for specific amino acids. Furthermore, the term "Nn" where "n" equals the position number of the nucleotide from 1 to 69 in oligonucleotide sequence (II) is used to identify variable nucleotides which can cooperate with other nucleotides in a codon to code for a plurality of amino acids. Thus, N16–N18 represents a specific codon which will code for the amino acid in position $Xaa^6$ of the resulting expressed peptide.

The term "substitution derivatives of Magainin 1 or Magainin 2" or "omission derivatives of Magainin 1 or Magainin 2" are generally synonymous with the term "AMPPP" as used in the context of the present invention. The term "substitution derivative" includes not only peptides as previously described wherein at least one of $Xaa^6$, $Xaa^7$, $Xaa^8$, $Xaa^{10}$, $Xaa^{11}$, $Xaa^{13}$, Xaa18, $Xaa^{19}$, $Xaa^{21}$, $Xaa^{22}$, and $Xaa^{23}$ are substituted, but may also include peptides of 21 to 24 amino acids in length with substitutions in any of the other positions.

The term "substitution" is intended to define compositions in which at least one of the 18–24 residues in either Magainin 1, Magainin 2, or non-Magainin 1, non-Magainin 2 peptides embodied in the present invention, or the single or double residue omission derivatives thereof are intentionally altered from their otherwise natural structure and order as previously described. Illustrative examples of substitution derivatives would include [$Arg^7$, $Glu^8$]Mag 1 (where Mag 1 refers to Magainin 1) [$Lys^7$, $Glu^8$, Des $Lys^{22}$, Des Ser $^{23}$]Mag 1, [$Ala^{19}$]Mag 1, [$Arg^7$, Des $Met^{21}$]Mag 1, [$Phe^7$, $Ala^{13}$, $Ala^{18}$]Mag 2, [$Lys^7$]Mag 2, [$Arg^7$]Mag 2, Met[Des $Gly^1$, $Glu^8$]Mag 2 and the like.

The term "derivative" as used herein includes AMPPPs having between about 18 and about 23 amino acid residues in length. These peptides, but for the absence of up to five amino acids, are the same in both sequence and order as the full 23 residue AMPPPs in accordance herewith. Because the omission or deletion of up to five amino acids can be in any of the 23 positions of the peptides having the general sequence II, to the extent such deletions are made, it is more convenient and more conventional to describe the 23 residue AMPPP counterpart preceded by the indication of which omissions are made. Illustrative examples of such derivative AMPPs are [Des $Gly^1$, Des $Ile^2$, Des $Gly^3$, Des $Lys^4$, $Ala^{13}$, $Ala^{18}$, Des $Ser^{23}$]Mag 1 and [Des $Gly^1$, Des $Ile^2$, Des $Gly^3$, Des $Lys^4$, Des $Phe^5$, $Ala^{19}$]Mag 2. "Derivative" does not necessarily mean that the AMPPP is first constructed and then specific deletions are made. The term also includes AMPPPs which are constructed with less than 23 residues.

The terms "single residue omission derivative," "single omission derivative" and "single residue deletion derivative" are meant to include AMPPPs 22 residues in length. These are peptides which, but for the omission of one of 23 residues when compared to a Magainin 1, Magainin 2, or the non-Magainin 1, non-Magainin 2 peptides embodied in the present invention, or substitution derivatives thereof, are otherwise not modified. Because the omission or deletion can be in any of the 23 positions of the parent AMPPP, it is more convenient and more conventional to describe the 23 residue AMPPP counterpart preceded by the indication of which single residue omission has been made. For example, the deletion derivative of Magainin 2 which omits residue 5 is described by the nomenclature [Des $Phe^5$]Magainin 2 where "Des" indicates a deletion. Similarly, the deletion derivative of a Magainin 2 substituted with Arg at position 7 which omits residue 5 is described by the nomenclature [Des $Phe^5$, Arg 7]Magainin 2.

However, despite the fact that, for example, a 23 residue AMPPP may recite the use of Pro in position 11 ($Xaa^{11}$=Pro), the single residue omission derivative thereof may exclude the residue at position 11. In such an instance, the descriptive nomenclature which would be used would be, for example, [Des $Xaa^{11}$]AMPPP wherein AMPPP would refer to the peptide counterpart to this single residue omission derivative (which counterpart itself may be a substitution and/or single residue omission derivative) from which the residue at position 11 had been deleted.

Similarly, the term "trinucleotide omission derivative of an oligonucleotide" contemplates an oligonucleotide designed to express an AMPPP which is a single residue omission derivative as previously defined. Because oligonucleotides are functional as codons, it is necessary that the entire three nucleotide codon be eliminated from the sequence to prevent expression of a particular amino acid and to ensure that the reading frame of the remaining sequences remain the same. An illustrative example of a trinucleotide omission derivative of an oligonucleotide within the scope of the present invention is the oligonucleotide having the sequence

```
GGAATAGGAA AGTTTCTGCA CTCAGCAG ARGTTTGGAA    40    (III)

AGGCATTTGT GGGAGAGATA ATGAAG                 66
```

which encodes the peptide [Des $Ser^{23}$]Mag 1.

The terms "double omission derivative" or "double residue omission derivative" are used in the same manner as the terms "single omission derivatives" or "single residue omission derivatives" and are meant to include AMPPPs of 21 residues in length. Omissions of amino acid residues in double residue omission derivatives may be consecutive, such that, for example, residues 22 and 23 ($Xaa^{22}$–$Xaa^{23}$) are omitted or they may be staggered such that, for example, residue 9 (Ala) and residue 17 (Val) are simultaneously omitted.

The term "six-nucleotide omission derivative of an olignucleotide" contemplates an oligonucleotide designed to express an AMPPP which is a double residue omission derivative. With reference to the oligonucleotide sequence (III), the further omission of nucleotides 64, 65 and 66 would result in an oligonucleotide which encodes the peptide [Des $Lys^{22}$, Des $Ser^{23}$]Magainin 1.

AMPPPs in accordance with the present invention may be advantageously produced by either a traditional chemical synthesis or by one or more methods of inserting specific DNA material genetically encoding one or more AMPPPs into a host cell and allowing that cell to express the desired peptide.

With regard to the traditional chemical synthesis, AMPPP's in accordance with the present invention can by synthesized using any of the known peptide synthesis protocols such as those described in "The Peptides: Analysis, Synthesis, Biology"; Volume 2—"Special Methods in Peptide Synthesis, Part A", E. Gross and J. Meienhofer, Eds., Academic Press, New York, 1980, and Volume 9—"Special Methods in Peptide Synthesis, Part C", S. Udenfriend and J. Meienhofer, Eds., Academic Press, San Diego, 1987.

Preferred for use in this invention for the chemical synthesis of peptides are solid phase techniques because they allow the rapid synthesis of highly pure peptides. In such procedures, peptides are synthesized, preferentially one amino acid at a time, on an insoluble polymer support (called a resin) starting from the C-terminus of the peptide. A synthesis is begun by appending the C-terminal amino acid (CTAA) of the peptide to the resin through a chemical linking group, such as an amide or an ester. If the latter is linked to the resin as an ester, the resulting peptide will be a C-terminal carboxylic acid; if linked as an amide, the resulting peptide will be a C-terminal amide. The CTAA, as well as all other amino acids used in peptide synthesis need to have their alpha-amino groups and side chain functionalities (if present) differentially protected as derivatives that can selectively be removed (deprotected) during the synthesis. Synthesis (coupling) is performed by reacting an activated form of an amino acid, such as its symmetrical anhydride or an active ester, with the unblocked alpha-amino group of the N-terminal amino acid appended to the resin. The sequence of deprotecting such alpha-amino groups followed by coupling is repeated until the entire peptide chain is constructed. All of the functionalities present in the peptide are then deprotected and the peptide is cleaved from the resin, usually in the presence of compounds called scavengers, which inhibit side reactions with the peptide during this process. The resulting peptide is then purified by a variety of techniques such as gel filtration, ion exchange and high performance liquid chromatography (HPLC). During the cleavage and purification processes, the peptide may be converted into any of a number of acid-salt forms bound to the amino groups present at the N-terminus and to any lysines, arginines, histidines or ornithines of the peptide and, consequently, the resulting pure peptide is usually obtained in the form of such a salt.

Preferred for use in this invention are Merrifield-type solid phase techniques as described in G. Barany and R. B. Merrifield, "Solid-Phase Peptide Synthesis," *The*

*Peptides: Analysis, Synthesis, Biology,* Volume 2, Ch. 1, pp 3–284; and in J. M. Stewart and J. D. Young in "Solid-Phase Peptide Synthesis, 2nd Ed.", Pierce Chemical Company, Rockford, Ill., 1984. In general, any standard side group protection strategy may be advantageously utilized, although t-Boc (tert-butyloxycarbonyl; see, for example, Barany and Merrifield, and Stewart and Young, supra) and FMOC (9-fluorenylmethoxycarbonyl; see, for example, E. Atherton and R. C. Sheppard in "The Fluorenylmethoxycarbonyl Amino Protecting Group," supra, Volume 9, Ch. 1, pp 1–38) strategies are preferred.

The synthesis of peptide-resins required as precursors to peptides containing a C-terminal carboxylic acid are typically begun on commercially available cross-linked polystyrene or polyamide polymer resins such as chloromethyl, hydroxymethyl, aminomethyl, PAM (phenylacetamidomethyl), HMP (p-hydroxymethylphenoxyacetic acid), p-benzyloxybenzyl alcohol, Hycram (4-bromocrotonyl-beta-alanylamidomethyl); Advanced Chemtech, Inc., Louisville, Ky.), or Sasrin (2-methoxy-4-alkoxybenzyl) alcohol; Bachem Bioscience, Inc., Philadelphia, Pa.). Coupling of amino acids can be accomplished using either symmetrical anhydrides produced, for example, from DCC (dicyclohexylcarbodiimide), HOBT (1-hydroxybenzotriazole) active esters produced, for example, from DCC/HOBT or, for example, from various BOP reagents (see, for example, J. Coste, et al., "BOP and Congeners: Present Status and New Developments", Proceedings of the Eleventh American Peptide Symposium; Peptides: Chemistry, Structure and Biology, J. E. Rivier and G. R. Marshall, Eds., ESCOM, Leiden, Neith., 1990, pp 885–888) in solvents such as DCM (dichloromethane), DCM containing TFE (trifluoroethanol), DMF (N,N-dimethylformamide), NMP (N-methylpyrrolidone), or NMP containing DMSO (dimethylsulfoxide).

Preferred for use in this invention are coupling of symmetrical anhydrides of t-Boc-protected amino acids, except for arginine (Arg), asparagine (Asn), glutamine (Gln), and histidine (His), which are preferably coupled as HOBT active esters produced from DCC/HOBT, on PAM resins in DMF or DMF/DCM solutions, and coupling of DCC/HOBT produced HOBT active esters of FMOC protected amino acids on HMP-polystyrene resins in NMP solutions.

More preferred for use in this invention is coupling of DCC/HOBT produced HOBT active esters of t-Boc protected amino acids on PAM resins first in NMP, then in an 80/20 solution of NMP/DMSO, and finally in an 80/20 solution of NMP/DMSO containing 1.9 mmol DIEA/0.5 mmol PAM resin.

Synthesis of peptide-resins as precursors to peptides containing a C-terminal amide can satisfactorily be achieved using the previously described procedures. However, a polymer support such as a benzhydrylamine (BHA) or 4-methylbenzhydrylamine (MBHA) polystyrene resins should be used. Preferred for use in accordance with this aspect of the present invention, i.e., the production of AMPPPs having an amide group bound at the C-terminus are 4-methylbenzhydrylamine-polystyrene resins.

Many types of side-chain protecting groups may be used for either the t-Boc or FMOC solid-phase synthesis as described, for example, by Barany and Merrifield, supra, Gross and Meienhofer, Eds., "The Peptides: Analysis, Synthesis, Biology", Volume 3—"Protection of Functional Groups in Peptide Synthesis", Academic Press, New York, 1981, and Stewart and Young, supra, for t-Boc amino acids, and by Atherton and Sheppard, supra, for FMOC amino acids.

Preferred for use in this invention for t-Boc amino acids are MTS (mesitylene-2-sulfonyl) for arginine, OBzl (benzyl ester) for aspartic acid, 4-MeBzl (4-methylbenzylthioether) for cysteine, $Bzl_2$ (dibenzyldiether) for 3,4-dihydroxyphenylalanine, OBzl for glutamic acid, Bom (benzyloxymethyl) or Z (benzyloxycarbonyl) for histidine, Bzl for both 3- and 4-hydroxyproline, Cl-Z (2-chlorobenzyloxycarbonyl) for both lysine and ornithine, $Bz_1$ for both serine and threonine, CHO (formyl) for tryptophan and Br-Z (2-bromobenzyloxycarbonyl) for tyrosine. Methionine may be protected as its sulfoxide, Met(O), but preferably is used unprotected.

AMPPPs in accordance with the present invention can be synthesized using either automated instruments or manual techniques. However, automated techniques are preferred. All of the examples of AMPPPs described in this invention were actually prepared using an Applied Biosystems, Inc. (ABI) Model 430A automated peptide synthesizer using the t-Boc protocols described in the Applied Biosystems Model 430A peptide synthesizer User's Manual, Version 1.30, Section 6, Applied Biosystems, Foster City, Calif., February 1987 (revised November 1987 and October 1988).

According to these protocols, the peptides are assembled on the resins starting from the C-terminus of the peptide. PAM or HMP resins required for the synthesis of C-terminal carboxylic acids can be purchased from ABI or other manufacturers already linked to the alpha-amino acid and side chain protected C-terminal amino acid. However, when preparing C-terminal carboxyamides, the C-terminal amino acid must first be coupled to either a BHA or MBHA resin. In either case, the resin containing the alpha-amino and side chain protected C-terminal amino acid is placed into the reaction vessel and the peptide chain is preferably assembled one amino acid at a time (assemblage of peptide fragments is possible but is usually less preferred for the AMPPPs described in this invention) by a repetitive sequence of deprotecting the alpha-amino group of the N-terminal amino acid appended to the resin and coupling to this the next amino acid, which is also alpha-amino and side chain protected.

The sequence of deprotection of the alpha-amino group of the N-terminal amino acid followed by coupling of the next, protected amino acid is continued until the desired peptide chain is assembled. The resulting N-terminal and side chain protected peptide linked to a polymer support resin is then subjected to the appropriate deprotection and cleavage procedure to provide the unprotected peptide, usually as N-terminal and lysine, histidine, arginine and ornithine acid salts.

Syntheses were performed using t-Boc protection strategies starting from 0.5 mmol of the C-terminal amino acid resin and 2.0 mmol of the side-chain protected, t-Boc amino acid in the coupling steps. These amounts, however, are not critical and proportionally larger or smaller amounts can be used depending on the type of automated instrument or manual apparatus employed. For example, syntheses utilizing as little as 0.1 mmol and as large as 0.6 mmol of amino acid-PAM resin have been performed by the inventors using the ABI instrument. Although a molar ratio of the to-be-coupled amino acid to the amino acid or peptide appended to the PAM resin of 4.0 is preferred when using this instrument, smaller and larger ratios may be employed. Ratios as low as 3.33 (0.6 mmol PAM resin/2.0 mmol of amino acid) have been used without any significant decrease in coupling efficiencies. Lower ratios may be employed to increase the quantity of peptide produced per run but are less preferred because the coupling efficiency and, hence, peptide purity may be lower. Larger ratios are generally not preferred because they are not any more efficient.

In syntheses based on t-Boc protection strategies in DMF, deprotection of alpha-amino groups is performed at ambient temperature using TFA/DCM followed by neutralization with DIEA/DMF. Symmetrical anhydrides are formed from DCC in DCM, except for leucine, methionine sulfoxides, tryptophan and formyl-tryptophan, which are formed in 10% DMF in DCM. After filtration of by-product DCU (N,N-dicyclohexylurea), the DCM is evaporated and replaced with DMF while the temperature is maintained at 10°-15° C. For AMPPPs synthesized using this protocol, amino acids were double coupled after the length of the growing peptide chain exceeded nine amino acids. For these cases, the DCM solution, after filtration, is used directly in the next step. HOBT active esters are formed for asparagine, glutamine and protected histidine from the reaction of DCC with HOBT containing 8-10% v/v DCM, and from arginine(MTS) from the reaction of DCC with HOBT containing 25-30% v/v DCM. After filtration of by-product DCU, the HOBT active ester solutions are used directly in the next step without removal of the DCM. These four amino acids are always double coupled using the same procedure.

Once either the amino acid symmetric anhydride or HOBT active ester is produced in the appropriate solvent, the solution is transferred to the reaction vessel and shaken with the N-terminal alpha-amine deprotected peptide-resin. Coupling takes place during this period, which initially ranges from 18-26 minutes for symmetrical anhydrides to 26-42 minutes for HOBT active esters. The coupling period is gradually increased as the peptide chain is lengthened. For example, after 15 amino acids, an additional 10 minutes is added. Couplings are initially performed at the temperatures at which the symmetrical anhydrides are formed, but gradually ambient temperature is reached during the coupling period. At the completion of the coupling period, the resin is washed with DCM, a sample taken for ninhydrin monitoring (see Sarin et al., "Quantitative Monitoring of Solid-Phase Peptide Synthesis by the Ninhydrin Reaction," Anal. Biochem. 117, (1981), 147-157, and then dried in preparation for the next coupling cycle.

In syntheses based on t-Boc protection strategies in NMP, deprotection of alpha-amino groups is performed as above, except that neutralization of excess TFA is accomplished by washes with DIEA/DCM, DIEA/NMP and NMP alone. All amino acids are converted to HOBT active esters by reacting 1.0 equivalent each of DCC, HOBT and an N-terminal and side chain protected amino acid in NMP for about 40-60 minutes at ambient temperature. After filtration of by-product DCU, the HOBT active ester solutions are used directly in the coupling reaction. Coupling is performed at ambient temperature for 30 minutes in DMP, for another 16 minutes after enough DMSO is added to give a 20:80 solution of DMSO in NMP, and finally for another seven minutes after the addition of 1.9 mmol of DIEA. As the length of the peptide chain is increased, longer coupling times are used. For example, after the peptide chain has reached 15 amino acids, the coupling time will have increased by 15 minutes. Double couple cycles are performed in the same manner as the single couple cycles, but were generally used only for $Lys^4$ or the equivalent in AMPPPs. At the completion of the coupling cycles, unreacted amino groups remaining on the peptide-resin are capped by treating them with a solution of 10% acetic anhydride and 5% DIEA in DCM for two minutes, followed by shaking with 10% acetic anhydride in DCM for four minutes. After washing well with DCM, a sample of the resin is taken for ninhydrin monitoring of coupling efficiency as above, and then dried in preparation for the next coupling cycle. Coupling efficiencies using either DMF or NMP were always greater than 98%, and in most cases greater than 99%.

AMPPPs, in accordance with the present invention, may also be successfully synthesized using the FMOC chemistry described herein and available on an ABI Model 430A peptide synthesizer (K. M. Otteson, "Recent Developments with NMP Chemistry" in "Is Protein Chemistry an Art or a Science?", Applied Biosystems, FASEB Meeting, New Orleans, April, 1989). Also, S. Nozaki, "Solid Phase Synthesis of Magainin 1 Under Continuous Flow Conditions", *Chem. Lett.*, (1989), 749-752, has described in detail a method for synthesizing Magainin 1 using HMP resin and an automated FMOC procedure very similar to the one described herein.

Although all of the peptides described herein may be individually prepared, it is sometimes desirable and expedient to simultaneously prepare multiple peptides. Procedures for performing such syntheses are well known in the literature, and commercial instruments for performing such tasks are also available. For example, Cuervo, et al., "The Magainins: Sequence Factors Relevant to Increased Antimicrobial Activity and Decreased Hemolytic Activity" supra, and "Synthesis and Antimicrobial Activity of Magainin Alanine Substitution Analogues", supra, reports the simultaneous preparation of omission and alanine substitution analogues of C-terminal amides and carboxylic acids of Magainin 1 and Magainin 2 using the SMPS (simultaneous multiple peptide synthesis) method with t-Boc protected amino acids on both PAM and 4-methylbenzhydryl amine resins. Also, F. S. Tjoeng, et al., "Multiple Peptide Synthesis Using a Single Support (MPS3)," *Int. J. Peptide Protein Res.* 35, (1990), 141-146, simultaneously prepared Magainin 2 analogues substituted with a variety of amino acids at position 21 using manual synthesis of t-Boc protected amino acids and PAM resins. In the same paper, however, these authors also showed that the method could be automated using an ABI Model 430A peptide synthesizer for the simultaneous synthesis of 11-substituted analogues of a porcine angeotensinogen peptide.

Procedures similar to those disclosed in the aforementioned paper have been used in the practice of the present invention specifically. In accordance herewith, a preferred technique employed t-Boc amino acids, PAM resins and DCC/HOBT couplings in NMP-NMP/DMSO for the simultaneous synthesis of three magainin substitution analogues. A larger number of substitution analogues can simultaneously be coupled, but the separation of the resulting peptides becomes more difficult and the yield of each resulting peptide decreases.

In the practice of the present invention, it has been possible to simultaneously synthesize portions of a variety of AMPPPs containing large common segments. For example, AMPPPs differing only at the C-terminus in substitution or chain length can simultaneously be synthesized by mixing together PAM resins containing the differing C-terminal sequences and then simultaneously sequentially coupling the common amino acid segments onto the mixture of resins in the normal manner. For this purpose, the use of HOBT active esters produced using DCC/HOBT in NMP-NMP/DMSO using t-Boc amino acids on PAM resins is the preferred method.

Similarly, large segments of AMPPPs differing mainly at the N-terminus can simultaneously be synthesized by first preparing the peptide-PAM resin containing the common C-terminal chain until the first differing amino acid at the N-terminus is reached. The peptide-resin is then divided into separate vessels and each individual peptide synthesis continued independently. The two growing peptide-resins may be coupled to completion or further divided at a later stage of peptide synthesis if other desirable branching positions are reached. Preferred for use in multiple peptide syntheses within the scope of this invention are t-Boc protocols on PAM resins utilizing DCC/HOBT couplings in NMP-NMP/DMSO. In order to increase the amount of peptide-resin produced, 0.6 mmole rather than the standard 0.5 mmole of resin may be employed in multiple peptide syntheses without losing coupling efficiency.

The peptides obtained as precursors for either C-terminal carboxylic acid or amide peptides may be deprotected and cleaved from the resins using any of the well known, standard procedures described in the literature (see, for example, Barany and Merrified, supra; Stewart et al., supra; J. P. Tam and R. B. Merrifield in "Strong Acid Deprotection of Synthetic Peptides: Mechanisms and Methods", ("The Peptides: Analysis, Synthesis, Biology", Volume 9, Ch. 5, pp 185–248); and Applied Biosystems, "Strategies in Peptide Synthesis-Introduction to Cleavage Techniques", Applied Biosystems, 1990. For t-Boc peptide-resins, for example, these include standard anhydrous HF (hydrogen fluoride), low-high HF, TFMSA (trifluoromethanesulfonic acid) and TMSOTf (trimethylsilyl trifluoromethanesulfonate). However, standard HF and low-high HF procedures are preferred for use in this invention for deprotection of and cleavage from t-Boc peptide-resins. It is also preferred that the N-terminal t-Boc protecting group be removed before the peptide is subjected to HF deprotection and cleavage.

Cleavage and deprotection of t-Boc-peptide-PAM resins using "standard" anhydrous HF conditions is generally performed according to the procedures given in the references cited above. Typically, about 1 g of the peptide-resin is stirred for about 50–90 min. at −5° C. to 0° C. in a solution of 10–12 mL of anhydrous HF containing 1.0 mL of anisole, 0.4 mL of dimethylsulfide (DMS), 0.2–0.4 mL of 1,2-ethanedithiol and 3 mg of 2-mercaptopyridine as scavengers. Slight variations in the amounts of scavengers present do not materially affect the results, and other scavengers, such as the ones described in the literature references cited above, may be used (for example, 3 mg of skatole should also be added for peptides containing tryptophan). It is preferred, however, that the reaction times and temperatures specified above be used, since shorter reaction times or lower reaction temperatures may result in incomplete deprotection or cleavage, while higher reaction temperatures may cause side reactions to occur. Longer reaction times are generally not beneficial and may lead to side reactions, although in certain cases, for example if an arginine protected with a tosyl group or several arginines are present in the peptide chain, reaction times up to two hours may be required to produce more complete deprotection. A particularly preferred procedure for performing the HF procedure is that of Immuno-Dynamics Inc., La Jolla, Calif. In this procedure the HF/scavenger/peptide-resin mixture is first stirred for 30 min. at −10° C. and then for 30 min. at 0° C. (5 min. longer per arginine at 0° C.).

The "low-high" anhydrous HF procedure may be used for the deprotection and cleavage of any of the peptide-resins described in this invention in order to minimize side reactions, such as methionine alkylation, but is particularly preferred for deprotection and cleavage of the peptide-resin mixtures produced from the simultaneous synthesis of multiple peptides. The preferred procedure followed is basically that described by J. P. Tam et al. in "$SN_2$ Deprotection of Synthetic Peptides with a Low Concentration of HF in Dimethyl Sulfide: Evidence and Application in Peptide Synthesis", *J. Am. Chem. Soc.* 105, (1983), 6442–6455, and Tam and Merrifield, "Strong Acid Deprotection of Synthetic Peptides: Mechanisms and Methods," supra and involves stirring for about two hours at −5° C. to 0° C. about 1 g of the peptide-resin in a solution of 10–20 mL (10–12 mL is preferred) of 2.5:6.5:1 anhydrous HF/dimethyl sulfide/p-cresol (if the peptide-resin contains Trp(For), then a solution of 10:26:3:1 anhydrous HF/dimethyl sulfide/p-cresol/thiocresol is instead used). The HF and DMS are then removed at about −5° C. to 0° C. under vacuum, and 10 mL of fresh, anhydrous HF is added. The "high" or "standard" cleavage is then performed by stirring the mixture for an additional 45–90 min. at −5° C. to 0° C. A more preferred method for performing this "high" HF deprotection is that of Immuno-Dynamics Inc. In this procedure, 1 mL of anisole, 0.4 mL of DMS, 0.4 mL of 1,2-ethanedithiol and 3 mg of 2-mercaptopyridine are added along with the 10 mL of fresh, anhydrous HF, and the mixture is stirred for 30 min. at −10° C. and 30 min. at 0° C. (5 min. longer per arginine at 0° C.).

After completion of either the "standard" or "low-high" HF deprotection and cleavage procedure, the HF and any remaining DMS are completely evaporated under vacuum at −5° C. to 0° C. The resulting peptide-resin-scavenger mixture is then mixed with about 10–15 mL of diethyl ether, ethyl acetate or the like (volume is not critical, diethyl ether is preferred), filtered, and the residue washed another 2–4 times with 10–15 mL of diethyl ether, ethyl acetate or the like (volume is not critical, diethyl ether is preferred) to remove organic scavengers. It is preferable at this point to stir the residue for 30 min. with 5 mL of 2-mercaptoethanol (BME) in order to reduce methionine sulfoxides to methionines. The peptide is then extracted three times with 5–30 mL of 10–30% acetic acid containing 2% BME, the extracts are combined, diluted (if necessary) with water to give a final concentration of acetic acid of 10% or less, and then lyophilized (freeze-dried) to dryness. The weight of crude peptide obtained typically ranges from 50–90%.

After completing the "low-high" HF cleavage and deprotection procedure, a preferred method for extracting the peptide is that used by Immuno-Dynamics Inc.

In this procedure, after evaporation of the HF and DMS, the peptide/resin mixture is swollen with chloroform, washed with 3×10 mL of ether, and stirred for 20–30 min. with 5 mL of BME. The mixture is then extracted three times with 5–30 mL of 1:1 10–30% acetic acid/BME (sometimes an additional extraction with 20–30 mL of 50% aqueous acetonitrile containing 0.1% TFA is beneficial). The extracts are then combined and extracted three times with 20 mL of ether to remove remaining scavengers, and the peptide is recovered by lyophilization of the aqueous acetic acid/-(acetonitrile)/BME layer.

The crude peptides obtained from the HF deprotection cleavage procedures are present as N-terminal, lysine, arginine, histidine, and ornithine hydrogen fluoride salts and presumably also contaminated with other fluoride salts and scavengers (if other deprotection schemes are used, such as trifluoromethanesulfonic acid, other inorganic salts, such as trifluoromethanesulfonates, will instead be present). Such peptide or inorganic salts are not desirable, since alone or in the presence of moisture they may act as strong acids, which may either decompose the peptide or be toxic to a plant. It is therefore preferable to rid the peptide of such salts by further purification, which also provides a peptide with higher activity per unit weight. A preferred method for purifying the peptide is to remove the fluoride salts by anion exchange chromatography and then isolate it by HPLC (high performance liquid chromatography).

As typically performed in the practice of this invention, anion exchange chromatography provides the AMPPPs as acetate salts, while HPLC provides the AMPPPs as trifluoroacetate salts.

A typical method for performing ion exchange chromatography is to dissolve the crude peptide in a minimum volume of 5–30% acetic acid (the higher concentrations of acetic acid are required for the more hydrophobic peptides), filter off any residual insoluble material (such as occluded resin) and pass the solution through an anion exchange resin, such as BioRad AG 1X-8 (acetate form) (Bio-Rad Laboratories, Richmond, Calif.) in 5–30% acetic acid. The resulting peptide fractions, detected by a ninhydrin test (Sarin et al., supra) are combined and lyophilized to provide the peptides as N-terminal, lysine, arginine, histidine, and ornithine acetate salts, free of inorganic impurities, but possibly still containing scavengers. The peptides obtained in this manner are 50–80% pure, according to HPLC analysis (see below), and, as such, are highly effective in destroying plant pathogens. A peptide with somewhat higher activity per unit weight may be obtained, either before or after the anion exchange procedure, by treating the peptide salts with a weak base such as 5–10% ammonium bicarbonate or 6M guanidine hydrochloride in order to reverse any N→O acyl shift that occurred in peptides containing serines and/or threonines under the acidic cleavage conditions. Typically, this is accomplished by dissolving the peptide salt in 5–10% ammonium bicarbonate, allowing the solution to sit overnight at 15°–25° C. and then recovering the peptide by lyophilization.

In some cases, particularly when methionine is protected as its sulfoxides during the peptide chain assembly, it is advantageous to again treat the peptide mixture with a reducing agent in order to reduce any remaining methionine sulfoxides back to methionine. Although many reagents are described in the literature for this purpose, such as DTT (dithiothreitol) and DTE (dithioerythritol), MMA (N-methylmercaptoacetamide) is preferred. The reduction is typically performed by incubating a solution of 1 to 5 mg/mL of peptide in about a 10% w/v solution of MMA in 10–30% acetic acid for 12–48 hours at 20°–40° C. under a nitrogen atmosphere following the procedure of A. Culwell in "Reduction of Methionine Sulfoxide in Peptides Using N-Methylmercaptoacetamide" (MMA), Applied Biosystems Peptide Synthesizer User Bulletin No. 17, (1987), Foster City, Calif. The reduction can be monitored by HPLC, and the incubation stopped when the reduction is complete. Reduction of the methionine sulfoxides to methionine is not required, since the inventors have shown that such methionine sulfoxide containing peptides have activity against plant pathogens, but peptides with a higher activity per unit weight can be obtained by performing the reduction procedure. In cases where the peptides have been treated with MMA, excess MMA and associated by-products are removed by passing a solution of the peptide mixture in 5–30% acetic acid through a Sephadex G-25 column (Pharmacia LKB Biotechnology, Inc., Piscataway, N.J.) and monitoring the effluent at 254 nm. The peptide-containing fractions are combined and dried by lyophilization.

Peptides with the highest activity per unit weight are obtained by further purifying them by HPLC (high performance liquid chromatography). Typically, the peptides are purified by reversed phase HPLC by injecting 15–30 mg of the peptide dissolved in 1–2 mL of 0.1% TFA (trifluoracetic acid) onto a 2.2×25 cm, 10 micron, 300 angstrom Vydac (Nest Group, Southboro, Mass.) C-4 column and eluting with various gradients of acetonitrile and water containing 0.1% TFA. The peptides obtained in this manner are N-terminal, lysine, arginine, histidine, and ornithine trifluoracetic acid salts, which are generally greater than 95% pure according to HPLC integration at 215 nm. Analytical HPLC of the peptide fractions is performed on a 0.46×25 cm, 10 micron, 300 angstrom, Vydac C-4 column using the following elution conditions: linear gradient of 0 to 60% B in A over 30 min; flow rate=1.0 mL/min; solvent A=0.1% aqueous TFA; solvent B=0.08% TFA in acetonitrile; monitoring by UV absorbance at 215 nm.

The structures of the peptides in most cases have been confirmed by amino acid or mass spectral analysis. Amino acid analysis of peptides was performed, following hydrolysis with 6N hydrochloric acid at 100° C. for 24 hours with an ion exchange column (for example, a Beckman Spherogel AA-$Li^+$ cation exchange column) by HPLC using a Beckman System Gold Amino Acid Analyzer (Beckman Instruments, Inc., Fullerton, Calif.) using ninhydrin detection. Amino acid analysis was also performed by Immuno-Dynamics, which detected the amino acids as PTC (phenylthiocarbamyl) derivatives on a Waters Associates Pico-Tag system (Millipore Corporation, Bedford, Mass.).

Amino acid analysis of the peptides have also been obtained using peptide-resins following the procedure of F. Westall et al. in "Fifteen Minute Acid Hydrolysis of Peptides," *Anal. Biochem* 61, (1974), 610–613. In these cases, the peptide-resin is hydrolyzed by 1:1 hydrochloric/propionic acid instead of hydrochloric acid alone. The resulting mixture is filtered through a 0.45 micron nylon filter using 2 to 4 volumes of water for washing, the filtrate is lyophilized and the residue analyzed as above.

Sprecra from FAB-MS (fast atom bombardment-mass spectrometry) of the peptides were obtained using a Kratos MS50RF mass spectrometer equipped with an Ion Tech B11NF saddled field gun operated at 8 kV and 40 microamps of current using xenon to create energetic ions. Spectra were obtained from a solution prepared by mixing 1 microliter of a 4 mM solution of the peptide with 1 microliter of 90% glycerol in 40 mM oxalic acid on the copper target of the sample probe. The instrument was calibrated with cesium iodide, scanned at a rate of 5 to 10 seconds per scan from a mass range from approximately 500 atomic mass units above and below the expected mass, and data were collected with multichannel analyzer programs available on a DS90 data system to provide $(M+H)^+$ fragments.

AMPPP Genetic Synthesis and Purification

As previously noted, AMPPPs can also be prepared by introducing into a host cell a deoxyribonucleotide or DNA gene sequence, like those of formulas II and III, encoding one or more AMPPPs with appropriate regulatory signals such as a gene promoter sequence and a gene terminator sequence appended to such a gene sequence, and realizing expression of the gene sequences encoding AMPPPs in such a host cell through biological processes for protein synthesis. The host cell for this process can be either procaryotic (for example, a bacterial cell) or eucaryotic (for example, a plant or animal cell) in origin. For purposes of large scale production, microbial hosts such as bacteria or yeasts may be used due to the advanced state of fermentation processes for those organisms. Alternatively, other gene expression systems can be used for production of AMPPPs such as those involving fungi (for example, Neurospora), cultured human cells or insect cells.

Genes encoding AMPPPs can be prepared entirely by chemical synthetic means or can consist in part of a portion or all of a sequence derived from natural sequences encoding magainins. Chemical synthesis of oligonucleotides composed entirely of deoxyribonucleotides can be achieved through application of solution chemistries or can be preferably carried out on solid supports. Several synthesis chemistries for oligonucleotides have been devised and include phosphotriester, phosphite-triester and phosphoramidite chemistries. See M. H. Caruthers, "New methods for chemically synthesizing deoxyoligonucleotides" in *Methods of DNA and RNA Sequencing* (S. M. Weissman, Ed.; Praeger Publishers, New York), (1983), 1-22, and K. Itakura et al., "Synthesis and use of synthetic oligonucleotides:, *Ann. Rev. Biochem.* 53, (1984), 323 356. Phosphoramidite synthesis chemistries such as those involving N,N-dimethylaminophosphoramidites or beta-cyanoethyl-diisopropylaminophosphoramidites or deoxyribonucleoside-morpholino-methoxyphosphines are preferred because of their efficient coupling of nucleotides to a growing oligonucleotide chain and for the stability of the chemical reagents employed. The most preferred phosphoramidite chemistries are those employing beta-cyanoethyl-diisopropylaminophosphoramidites because of their extended stability relative to comparable intermediates and their avoidance of toxic reagents such as thiophenol. See, S. L. Beaucage and M. H. Caruthers, "Deoxynucleoside phosphoramidites—a new class of key intermediates for deoxypolynucleotide synthesis", *Tetrahedron Lett.* 22, (1981), 1859–1862; L. J. McBride and M. H. Caruthers, "An investigation of several deoxynucleotide phosphoramidites useful for synthesizing deoxyoligonucleotides:, *Tetrahedron Lett.* 24, (1983), 245–248; T. Dorper and E. L. Winnacker, "Improvements in the phosphoramidite procedure for the synthesis of oligodeoxyribonucleotides", *Nuc. Acids Res.* 11, (1983) 2575–2584; and S. P. Adams et al., "Hindered dialkylamino nucleoside phosphite reagents in the synthesis of two DNA 51-mers",*J. Amer. Chem. Soc.* 105, (1983), 661–663. Phosphoramidite chemistries on solid supports in brief consist of attaching a modified nucleotide to a solid material such as glass, silica gel, polyacrylamide, cellulose, polystyrene, nitrocellulose and some other generally chemically inert material. The nucleotide phosphate group and any exocyclic nitrogen atoms in the nucleotide base are protected on such supports with chemical groups so as to prevent unwanted side reactions during linear elongation of the oligonucleotide chain. Such attachments can be through a variety of linker or spacer moieties, but preferred linkers are generally long chain alkyl amines. See M.D. Matteucci and M. H. Caruthers, U.S. Pat. No. 4,458,066. The attached nucleotide is protected at the 5′ sugar position with an acid labile dimethoxytrityl chemical group which is removed with an acid such as benzenesulfonic acid, trichloroacetic acid or dichloracetic acid to free a 5′—OH group for coupling, thereby beginning linkage of additional nucleotides. Preferred acids for this deblocking or activation step are dichloroacetic acid or trichloracetic acid. A phosphoramidite monomer nucleoside protected similarly to the nucleotide attached to the solid support is then added in the presence of a weak acid to promote nucleophilic attack of the 5′—OH group on the phosphoramidite reagent. Preferred weak acids for the coupling step include tetrazole, amine hydrochlorides, and 3-nitrotriazole, with the most preferred weak acid being tetrazole. Failed coupling sites on the solid support are then blocked or capped by acetylation of free hydroxyl groups with acetic anhydride. A preferred coreactant in the capping step is 1-methylimidazole. The natural internucleotide phosphate diester linkage is subsequently generated at each cycle of nucleotide addition by treatment of the growing nucleotide chains on the solid support with a mild oxidation mixture. This oxidation step converts phosphorus (III) to the more stable phosphorus (V) oxidation state and prevents nucleotide chain scission at any subsequent deblocking or activation treatment steps by acid species such as dichloroacetic acid or trichloroacetic acid. Iodine is used as the oxidizing species with water as the oxygen donor. Preferred coreagents include tetrahydrofuran and lutidine. Following a wash of the solid support with anhydrous acetonitrile, the deblock/coupling/oxidation/capping cycle can be repeated as many times as necessary to prepare the oligonucleotide or oligonucleotides of choice, each time using the appropriate protected beta-cyanoethylphosphoramidite nucleoside to insert the nucleotide of choice carrying a purine or pyrimidine base. The purine bases preferably will be either adenine or guanine on the inserted nucleotide and the pyrimidine bases preferably will be cytosine or thymine. The simplicity of chemical synthesis of oligonucleotides has led to the development of practical guides for laboratory work and common use of commercial automated DNA synthesizers. See, M.H. Caruthers, "Gene synthesis machines: DNA chemistry and its uses", *Science* 230, (1985), 281–285; and J. W. Efcavitch, "Automated system for the optimized chemical synthesis of oligodeoxyribonucleotides" in *Macromolecular Sequencing and Synthesis, Se-*

*lected Methods and Applications* (Alan R. Liss, Inc., New York), (1988), 221–234. Commercial instruments are available from several sources such as DuPont Company (Wilmington, Del.), Milligen/BioSearch, Inc. (San Rafael, Calif.) and Applied Biosystems (Foster City, Calif.). Instruments used in accordance with the present invention were the Biosearch 8700 or the Applied Biosystems 391 PCR-Mate DNA synthesis instruments. The operation of these instruments and the details of the beta-cyanoethylphosphoramidite chemistry cycles used with them is described in either the Biosearch, Inc. model 8600/8700 instruction manual or the PCR-Mate Model 391 DNA synthesizer user's manual (Applied Biosystems part number 900936, version 1.00, revision A dated May 1989).

The last coupling cycle of oligonucleotides can be completed leaving the 5′ terminal dimethoxytrityl group on or off. The dimethoxytrityl group is preferably left on for convenience in subsequent purification of full-length oligonucleotides. The completed and protected oligonucleotides must be deprotected and cleaved from the solid support prior to purification. The solid support bearing the completed oligonucleotides is treated with fresh concentrated ammonium hydroxide at room temperature for at least one hour to cleave the oligonucleotides from the support resin. The solid support is then washed with more concentrated ammonium hydroxide and the combined concentrated ammonium hydroxide is incubated at 55°–60° C. for at least eight hours in a sealed vial in order to remove the protecting chemical functionalities from the protected bases. The sample is then cooled and evaporated to dryness under vacuum. The sample may also be reevaporated from fresh concentrated ammonium hydroxide or ethanol of at least 95% purity by volume. The final sample can then be stored in a lyophilized (dry) state or can be resuspended in sterile distilled water before storage at −20° C. See the PCR-Mate Model 391 user's manual, supra, and M. H. Caruthers et al., "Chemical Synthesis of Deoxyoligonucleotides by the Phosphoramidite Method," *Methods in Enzymology* 154, (1987), 287–313.

Any cleaved and deprotected oligonucleotides prepared by methodology drawn from the preferred choices above can be purified by one or more of several methods known in the art. These purification techniques include but are not limited to polyacrylamide gel electrophoresis, agarose gel electrophoresis, size exclusion chromatography, affinity chromatography, high performance liquid chromatography and hydrophobic interaction chromatography. The preferred method is selected from the group of purification techniques which consists of polyacrylamide gel electrophoresis, high performance liquid chromatography and hydrophobic interaction chromatography. One such preferred method is polyacrylamide gel electrophoretic purification of oligonucleotides, lacking a dimethoxytrityl moiety on the 5′ terminus, on a vertical 12% polyacrylamide slab gel, 20×40×0.08 cm, in 7M urea, 90 mM Tris-HCl, pH 8.3, 90 mM borate, 1–2 mM disodium ethylenediaminetetraacetic acid (EDTA). A portion of each oligonucleotide to be purified (0.3–3.0 $A_{260}$ units) is evaporated to dryness under vacuum, resuspended in formamide: 1 mM disodium EDTA (>9:<1) containing at least 0.01% bromophenol blue and at least 0.01% xylene cyanol, heated 2–3 minutes in a boiling water bath, quickly placed in an ice slurry and then loaded in an individual well (at least 6 mm in width). The sample(s) is electrophoresed at 80–90 W towards the anode until the bromophenol blue has migrated at least two-thirds the length of the polyacrylamide gel. The full-length oligonucleotides are then visualized by placing the polyacrylamide gel on a piece of flexible, clear plastic wrap such as Saran Wrap, placing it on top of a thin layer chromatography plate (e.g., Silica Gel F-254; Fisher Scientific Company, Pittsburgh, Pa.) containing a fluorescent indicator compound and examining the polyacrylamide gel under short wavelength ultraviolet light illumination. The full-length band material is then excised in polyacrylamide and can be purified out of the gel by various methods such as electroelution or simple diffusion in buffer. The preferred method of extraction is diffusion into 0.5 mL of 0.3M sodium acetate, pH 7.5, overnight with shaking and successive extractions of the aqueous phase with phenol:chloroform (1:1, v:v) and ethanol precipitation. The precipitated oligonucleotide can then be resuspended in an appropriate volume (usually in the range of 10–1000 microliters) of a suitable buffer such as 10 mM Tris-HCl, pH 7.5, 1 mM disodium EDTA or in sterile distilled water and stored at −20° C. See unit 2.12, "Purification of oligonucleotides using denaturing polyacrylamide gel electrophoresis," in *Current Protocols in Molecular Biology*, F. M. Ausubel et al., Eds., (1989).

An alternative more preferred method of purification and one well suited for purification of oligonucleotides still having a dimethoxytrityl moiety on the 5′ terminus is high performance liquid chromatography (HPLC) on a reverse phase HPLC column. Such a reverse phase HPLC column can be packed with any of a variety of silica or polymer based resins which are commercially available from a number of vendors such as Millipore/-Waters (Milford, Mass.), The Nest Group (Southboro, Mass.), Rainin Instrument Company, Inc. (Woburn, Mass.), J. T. Baker Inc. (Phillipsburg, N.J.), Alltech Associates Inc. (Deerfield, Ill.), or Pierce Chemical Company (Rockford, Ill.). Oligonucleotides are loaded, fractionated and eluted from such an HPLC column by, for example, an acetonitrile gradient in any of several suitable non-destructive buffers. Preferred acetonitrile gradients are in the range of 5% to 40% and more preferably in the range of 5% to 30% in 0.1M triethylammonium acetate, pH 7.0, buffer. Preferred reverse phase HPLC columns include those with linear alkyl chain moieties bound to them such as $C^4$, $C^8$, or $C^{18}$ alkyl chains. The appropriate fractions containing purified full-length oligonucleotide are then pooled, evaporated under vacuum and resuspended in 3% (v/v) acetic acid in water at room temperature for 10–30 minutes. The detritylated oligonucleotides are then ethanol precipitated or purified by other suitable means such as size exclusion chromatography. Alternatively, full-length detritylated oligonucleotides can also be purified by HPLC using various types of columns and gradient materials. For guidance, see G. Zon and J. A. Thompson, "A review of high-performance liquid chromatography in nucleic acids research," *BioChromatography* 1, (1986), 22–32.

Another alternative more preferred method is purification of the oligonucleotide by hydrophobic interaction chromatography. This purification technique for the purposes of the present invention is a form of reverse phase chromatography under atmospheric pressure over a hydrophobic resin. A crude oligonucleotide mixture in the ammonium hydroxide deprotection and cleavage solution is applied to the hydrophobic resin which has been equilibrated in a suitable buffer such as 1.0M triethylammonium acetate, pH 7.0. Bound oligonucleotides are then detritylated by exposure to 2% trifluoracetic acid for 1-3 minutes and then recovered in 15-40% acetonitrile in water. The recovered oligonucleotide is then lyophilized and resuspended as described above in a suitable buffer or sterile distilled water.

One or more synthetic oligonucleotides will be necessary to prepare a partially or completely synthetic gene for the purposes of the present invention. Any appropriate oligonucleotides and/or portions or all of a natural gene such as a natural magainin gene can be assembled into a gene encoding one or more AMPPPs by denaturing these DNAs by some means such as heating, mixing with a chaotropic agent such as urea or formamide or exposure to an alkaline solution. Phosphate moieties can be attached enzymatically to any DNAs or oligonucleotides lacking them using an enzyme such as T4 polynucleotide kinase. See section 3.10 in *Current Protocols in Molecular Biology,* supra. Any oligonucleotides being used in the preparation of a gene within the scope of the present invention and in the presence or absence of any additional natural DNAs are then renatured or annealed by appropriate means, such as slow cooling to room temperature or dialysis to remove any chaotropic agents. These annealed DNAs can be linked covalently by treatment with a suitable enzyme such as T4 DNA ligase. See section 3.14 in *Current Protocols in Molecular Biology,* supra.

If necessary and where suitable, the gene products encoding AMPPPs prepared by this means can be prepared for appending to genetic regulatory DNA sequences by treatment with restriction endonucleases according to manufacturer's specifications or by methods known in the art. See, for example, T. Maniatis et al., *Molecular Cloning,* supra, pp. 104-106.

Genetic regulatory signals which are appended to genes encoding AMPPPs so as to render them capable of expression as protein in a defined host cell may include gene promoter sequences, which are DNA sequences recognized by the biological machinery of the host cell and which induce transcription of the DNA sequence into messenger RNA (mRNA) by an RNA polymerase within the host cell. This mRNA must then be capable of being translated on ribosomes within the host cell into a protein product. The gene promoter sequences may be derived in part or in whole from promoter sequences found in cells unlike those of the host cell so long as they meet the above criteria for transcription and translation. For example, a vegetative gene promoter sequence from the gram-positive bacterium *Bacillus subtilis* may be satisfactory for expression of an AMPPP gene in the gram-negative bacterium *Escherichia coli.*

A second genetic regulatory element which may be appended to an AMPPP gene for the expression of one or more AMPPPs is a gene terminator or polyadenylation sequence. This DNA sequence contains genetic information that interrupts and halts further transcription, and, in the case of eucaryotic cells, provides information directing attachment of one or more adenosine nucleotides at the 3' end of the mRNA. A gene terminator sequence may represent in part or in whole a terminator sequence originating from the genome of the host cell or from the genome of some unlike cell that is known to be effective at appropriately terminating transcription within the host cell. An example of such a sequence would be the *Salmonella typhimurium* his operon rho-independent transcription terminator sequence (see, for example, M. E. Winkler, *Escherichia coli and Salmonella typhimurium: Cellular and Molecular Biology* [F. C. Neidhardt, Ed.-in-chief; American Society for Microbiology, 1987], chapter 25) or the octopine synthase terminator sequence from an *Agrobacterium tumefaciens* Ti plasmid (see, for example, H. DeGreve et al., "Nucleotide sequence and transcript map of the *Agrobacterium tumefaciens* Ti plasmid-encoded octopine synthase gene,", *J. Mol. Appl. Genet.* 1, (1982), 499-511.

An AMPPP gene or genes with attached genetic regulatory signals is preferably introduced into a host cell of either procaryotic or eucaryotic origin for the intent of expressing the one or more AMPPPs encoded by the relevant genes. The means of introduction is well-described in the art and depends upon the type of host cell in which gene expression is being sought. For example, transformation of bacterial cells with externally supplied DNA such as cells of *Escherichia coli* can be accomplished by a calcium chloride procedure. Typically, the AMPPP gene or genes with attached genetic regulatory signals are covalently bound into a suitable transformation vector prior to the transformation procedure. Such vectors have been reviewed in *Vectors: a Survey of Molecular Cloning Vectors and Their Uses* by R. L. Rodriguez and D. T. Denhardt (Butterworths, Boston; 1988). See, also, T. Maniatis et al., *Molecular Cloning*, supra, pp. 247-255.

Once expressed with any such gene expression system in a suitable host cell, the AMPPPs may be extracted and/or purified by conventional means and used against plant pathogens in either a partially purified or a substantially purified form. Methods of extracting AMPPPs from host cells include heat and/or enzymatic lysis of the host cell, solubilization in a lipidic solvent or aqueous-organic micellar solution, and pressure rupturing of cell membranes and/or cell walls by forcing the host cells through a French press. The preferred method for cell lysis for the case of bacteria as host cells depends upon the scale of production being sought. For large scale production, heat or pressure rupturing of the bacterial cells is preferred. See, for example, H. Hellebust, "Different approaches to stabilize a recombinant fusion protein," *Bio Technology* 7, (1989), 165-168. The extracted AMPPPs may be used in their immediate form without further purification or may be partially or completely purified by application of one or more fractionations of cellular contents by a method such as size exclusion chromatography, ion exchange chromatography, electrophoresis, affinity chromatography and the like.

Another possibility is to use totipotent plant cells as the host recipient for expressing those genes encoding AMPPPs and expressing AMPPPs as protein product whereby the plant cells are capable of regenerating fertile crop plants. In this latter instance, the recipient plants are termed genetically transformed or transgenic plants. There are several known methods for introducing foreign genes into plants. The method of choice depends primarily on the type of crop plant that is to be transformed. However, many of these methods may be used in accordance with the present invention.

One method that is particularly efficient for the transfer of DNA into dicotyledonous plants involves the use of *Agrobacterium.* In this method the gene of interest (for example, a gene for an AMPPP with a *cauliflower mosaic* virus 35S 5' promoter region and a 3' OCS terminator region) is inserted between the borders of the T-DNA region that has been spliced into a small recombinant plasmid with a selectable gene (for example, genes encoding neomycin phosphotransferase II of transposon Tn5, phosphinothricin acetyltransferase, and the like). The recombinant plasmid is then introduced into an *Agrobacterium* host either by direct transformation or by triparental mating. The *Agrobacterium* strain carrying the gene of interest is then used in transformation of dicot plant tissue by co-culturing the bacterium with the plant sample (e.g., leaf disc) for a period of 2–3 days. Transformed cells are recovered by selection on the appropriate agent and plants can then be regenerated. See, R. B. Horsch et al., "A Simple and General Method of Transferring Genes into Plants," *Science* 227, 1985), 1229–1231.

Other methods that have been used in the transformation of plant cells, and in particular on the more recalcitrant monocotyledonous crop plants, include chemically induced transfer (e.g., with polyethylene glycol; see H. Lorz et al., "Gene transfer to cereal cells mediated by protoplast transformation." *Mol. Gen. Genet.* 199, (1985), 178–182), biolistics (W. J. Gordon-Kamm et al., "Transformation of Maize Cells and Regeneration of Fertile Transgenic Plants," *The Plant Cell,* 2, (1990), 603–618), microinjection (G. Neuhaus et al., "Transgenic rapeseed plants obtained by microinjection of DNA into microspore-derived proembryoids, "*Theor. Appl Genet.,* 74, (1987), 30-36) and others (I. Potrykus, *Bio technology* 9, (1990), 535–542.

External Application of AMPPP

If an external application of AMPPPs is to be used to protect a plant against pathogens, it would be expected that the AMPPPs would be diluted to form a liquid solution or suspension containing between 1–100 micrograms/mL of the AMPPPs or mixed with a diluent solid to be applied as a dust. The precise nature of application will depend in part on the particular pathogens being targeted. Detailed methods for adapting general methods of application to specific crops and pathogens can be found in *Methods For Evaluating Pesticides For Control Of Plant Pathogens,* K. D. Hickey, Ed., The American Phytopathological Society (St. Paul, Minn.), 1986. Methods of application that are expected to be particularly useful in accordance with this aspect of the present invention include intermittent aqueous and non-aqueous sprays of the entire plant or parts thereof, seed coatings, and inclusion in irrigation systems (e.g., greenhouse mist-benches). Adjuncts that could be added to the formulation would include agents to aid solubilization, wetting agents and stabilizers, or agents that would produce a microencapsulated product. The formulation should preferably not contain high concentrations of inorganic salts and particularly not divalent cations such as $Ca^{++}$, $Mg^{++}$, or $Fe^{++}$. External applications could also utilize recombinant microorganisms in either a viable form or after being converted into a non-viable form by a method that does not inactivate the AMPPPs. If viable recombinant organisms are used to deliver the AMPPPs, it would be preferable if they had the ability to colonize the target plant.

AMPPP Antimicrobial Activity

Those AMPPP compositions which are preferred for the purposes of the present invention are those which meet at least some of a multiplicity of criteria. A primary criterion for AMPPPs in accordance with the present invention is activity against one or more plant pathogens. That is, these peptides should be effective in retarding plant pathogens. The term "plant pathogens" encompasses those organisms that can cause damage and/or disease to plants, and includes fungi, procaryotes (bacteria and mycoplasma), viruses and viroids, nematodes, protozoa, and the like.

For example, there are more than 8,000 species of fungi that can cause plant disease. See, *Plant Pathology,* George N. Agrios, Third ed., Academic Press, Inc., 1988; *A Literature Guide for Identification Of Plant Pathogenic Bacteria,* A. Y. Rossman et al., American Pathological Society, St. Paul, Minn., 1988; *The Laboratory Guide for Identification Of Plant Pathogenic Bacteria,* N. W. Schad, Ed., American Phytopathological Society, St. Paul, Minn., 1980. In recognition of the extensive array of such pathogens, the most useful AMPPPs within the context of one aspect of the present invention are those which have a broad spectrum of activity, inhibiting or retarding the growth or survival of numerous plant pathogens, or which are very effective against specific groups of pathogens, especially groups which cause diseases in many crops. For example, *Erwinia* species are responsible for a variety of soft rot and wilt diseases that cost farmers hundreds of millions of dollars annually. One or more AMPPPs which could control the survival or proliferation of *Erwinia* species would therefore be desirable. More desirable, however, are AMPPPs which would also provide some measure of activity against other species of fungi and/or against other classes of pathogens which may combine to attack a specific host. Examples of such a condition are stalk rots in maize that are caused by different combinations of several species of fungi and bacteria (e.g. *Fusarium spp, Gibberella spp, Diplodia spp, Macrophomina spp, Pythium spp, Cephalosporium spp, Erwinia spp, Pseudomonas spp*). Other examples include conditions where damaged tissues are invaded by saprophytic organisms as in postharvest diseases of plant products.

A number of symbiotic or benign microorganisms, which are mainly bacterial species, are found associated with plants. Useful AMPPPs would be those which do not have an effect on the survival of these microorganisms while exhibiting effective control of one or more distinct plant pathogens. Therefore, in some situations, a degree of specificity is beneficial. For example, when protection of a root system is desirable, it would be beneficial to leave intact organisms such as *Rhizobium spp,* which fix atmospheric nitrogen or root colonizing organisms such as *Pseudomonas spp,* that serve to protect the roots from certain pathogens. Since many of these beneficial or benign organisms are bacteria, there is a specific utility for AMPPPs that have diminished activity against bacteria. AMPPPs in accordance with this aspect include, without limitation, [$His^{10}$]Mag 2, [$His^{11}$]Mag 2, [$His^{10}$, $His^{11}$]Mag 2, [$Thr^{8}$]Mag 2, [$Glu^{8}$]-Mag 2, and [$Phe^{7}$]Mag 2.

AMPPP Proteolytic Resistance

Another basis for selecting preferred AMPPP compositions in accordance with the present invention is resistance to digestion or degradation by one or more plant proteases or plant pathogen proteases. Plants contain enzymes which are used to degrade proteins within a cell, within a subcellular organelle, within a compartment, or within the extracellular space between cells. These enzymes, also known as proteases, degrade proteins and peptides by breaking specific bonds linking amino acid sequences and producing inactive or less active fragments. In the context of the present invention, this natural phenomenon can be disastrous because it can deactivate the AMPPPs which may otherwise protect a plant by retarding plant pathogens. This problem presents itself for both topically applied AMPPPs which are exposed to proteases contained within the extracellular spaces and expressed AMPPPs which are exposed to intracellular proteases.

Post-translational cleavage of the $Xaa^{10}$-$Xaa^{11}$ position is caused naturally by proteases native to the exudates of the skin of *Xenopus laevis*, indicating that this site is available to proteases for digestion. See *M. G. Giovannini* et al., supra.

At least some amino acid substitutions and/or deletions at sites adjacent to peptide bonds which can be characterized as sensitive to one or more plant proteases should reduce or eliminate proteolysis. This may be due, at least in part, to inhibition of the action of the respective plant protease or proteases through induction of a poor "fit" between the protease enzyme and the AMPPP substrate cleavage site.

It has been unexpectedly found that plant proteolytic degradation due to treatment of AMPPPs with plant extracellular fluid containing plant proteases occurs by cleavage of the bonds between His and Ser at positions 7 and 8, respectively, of Magainin 1 and Magainin 2, and Met and Asn at positions 21 and 22, respectively, of Magainin 2. In recognition of these phenomena, specific substitutions have been discovered at one or more of these positions which are effective in greatly reducing adverse proteolytic degradation by plant proteases. The peptides so modified are therefore likely candidates for expression in transgenic plants as well as being useful for conventional application for crop protection. Substitutions at the foregoing positions which may be effective in reducing, if not eliminating adverse proteolytic degradation by plants and/Or plant pathogen proteases, include Phe, Ala, Glu, Asp, Lys, Ser, or Arg at $Xaa^7$, Thr Asp Ala His or Glu at $Xaa^8$ Arg, Lys, His, Gln, Trp, Tyr, Thr, Val, Ala, Leu, Ile, Glu, Asp, or Phe at $Xaa^{21}$, or Arg, His, Glu, Trp, Tyr, Thr, Val, Ala, Leu, Ile, Gly, Asp, Phe, Pro, 3Hyp, 4Hyp, or Met at $Xaa^{22}$. The more preferred substitutions in accordance with this aspect of the present invention are Arg or Lys substitutions at $Xaa^7$ and/or Glu substitutions at $Xaa^8$.

The fact that Arg and Lys have been found to have a substantial effect on proteolysis is unexpected because of the similarity in charge at physiological pH between these compounds and the His residue that they replace in Magainin 1 and Magainin 2. Any or all of the preferred amino acid substitutions at positions 7, 8, 21, and/or 22 in AMPPPs may be combined with other substitutions, deletions, and/or extensions in accordance with the present invention to provide a peptide which is not only resistant to proteolysis, but also one with increased activity against one or more plant pathogens, with selected activity against specific plant pathogens, and/or with low phytotoxicity.

In deciding which substitution or substitutions to make at these positions to improve resistance to proteolytic degradation of an AMPPP, a number of factors should be considered. One factor to be considered is the effect of proteolytic degradation at the various sites. The fragments that result from the degradation of the bond between $Xaa^7$ and $Xaa^8$ are inactive against most plant pathogens. However, the 21-mer that results from cleavage at the bond between $Xaa^{21}$ and $Xaa^{22}$ may retain significant activity, particularly against plant pathogenic fungi. Thus, it is usually desirable to make substitutions in AMPPPs which will stabilize the $Xaa^7$-$Xaa^8$ bond, but it is not essential to make substitutions which will preserve the $Xaa^{21}$-$Xaa^{22}$ bond against proteolytic attack.

Furthermore, the size of the AMPPP may be significant in dictating whether or not a substitution should be made at the various positions, and particularly at positions 21 and 22. For example, [Des $Asn^{22}$, Des $Ser^{23}$-]Magainin 2 is a double residue omission derivative in accordance with the present invention which has significant antifungal activity. However, this 21-mer is identical to the 21-mer that might otherwise result from proteolytic degradation, there is no need to preserve the non-existent $Xaa^{21}$-$Xaa^{22}$ bond. It is nonetheless desirable to provide for decreased sensitivity of the remaining 21-mer by making substitutions which will reduce or eliminate degradation of the $Xaa^7$-$Xaa^8$ bond.

A measure of the relative resistance of an AMPPP to one or more plant proteases in a plant tissue, and particularly extracellular proteases, may be obtained by the use of a solution enriched in proteins, including plant proteases derived from plant tissue. In the case of extracellular proteases, this can be accomplished using standard methods for obtaining extracellular fluid such as that discussed in Z. Klement, "Method Of Obtaining Fluid From the Intercellular Spaces Of Foliage and the Fluid's Merit As Substrate For Phytobacterial Pathogens," *Phytopathology* 55, (1965), 1033–1034, or by collecting some portion of a supernatant solution taken from cultured cells of a particular crop plant or a plant tissue infiltrate. These procedures may also be employed to obtain proteases from plant pathogens. A dose response relationship can be inferred for any proteolytic degradation of the AMPPP if it can be demonstrated that incubation of an AMPPP for increasing lengths of time or with increasing concentrations of a solution, which contains one or more plant proteases, leads to an increasing amount of proteolytic degradation of the AMPPP. This method is far superior to other methodologies because it subjects an AMPPP to the proteolytic conditions and compounds that they might encounter in a crop plant treated therewith, or produced therein.

In addition to extracellular proteases, AMPPPs can also be tested against proteases resident in other organelles or compartments. This would be accomplished by mechanically or enzymatically disrupting the plant cells or tissue and then fractionating the organelles by velocity and density gradient centrifugation. The organelle would then be disrupted to release the internal protease(s). This general procedure could be used to examine the stability of AMPPPs in the presence of proteases in organelles such as chloroplasts, mitochondria, peroxisomes, vacuoles and the like.

Solutions prepared from a subcellular organelle, plant tissue, plant cell cultures, or plant pathogen cell cultures in accordance with the present invention are generally very dilute. The protease is usually present in solution in an amount of from about 1 ppm in water (one part per million parts of water) to about 1 ppt in water (one part per thousand parts of water). However, when used to test resistance to proteolytic degradation, the solution is further diluted up to 20 times with water. Thus, the protease may be present in an amount of as little as about 0.05 ppm in water. The actual amount of protease useful in reagents in accordance with the present invention is understandably difficult to articulate. However, it is preferred that the reagent used contain an amount of protease sufficient to cause at least 50% degradation of a tested compound in a predetermined time, usually less than about five hours. The reagent and the compound being tested are incubated at a temperature in the range of 15°-50° C., and preferably in the range of 20°-40° C. Degradation, to the extent it occurs, is stopped by inactivating the proteases within the reagent. This may be accomplished by a number of means such as the addition of an acid, such as citric acid or trifluoroacetic acid, the addition of a surfactant, or heating. A simple check for verifying the efficacy of the reagent is by testing its effect on Magainin 1 or Magainin 2 which have no natural resistance to proteolysis. If the Magainin 1 or Magainin 2 tested is sufficiently degraded in less than about five hours, then other AMPPPs tested with the reagent may be compared thereto.

Other conventional additives may be included in the reagents in accordance with the present invention for reasons which are readily apparent. These include buffers, such as Tris (tris-[hydroxymethyl]aminomethane); MES (2-[N-morpholino]ethane sulfonic acid); and HEPES (N-[2-hydroxyethyl]piperazine-N'-[2-ethanesulfonic acid]) and preservatives, such as sodium azide or thimerosal. Mixtures of these additives may also be useful. When present, these additives generally are present in an amount of about 0.01% to about 0.10%.

Proteolytic degradation can be monitored by a number of techniques, such as ion exchange chromatography, electrophoresis analytical techniques, isoelectric focusing, high performance liquid chromatography, size exclusion chromatography, affinity chromatography, immunoassay, and other methods known in the art. Confirmation of proteolytic degradation can be obtained by detecting fragments of an AMPPP. Additional proof of proteolytic degradation can be obtained by characterizing the composition of such AMPPP fragments. Such characterization can be by a variety of techniques known in the art, including but not limited to amino acid analysis and molecular weight determinations on such fragments. Preferred methods of molecular weight determination include FAB-MS and HPLC-MS. Information of this nature may also provide evidence as to the site or sites of proteolytic attack on an AMPPP and suggest sites of amino acid replacements and/or substitutions which would increase the resistance of an AMPPP to proteolytic degradation.

It is also possible that one or more of the AMPPPs embodied within the present invention would prove resistant to degradation by one or more plant proteases, but would be sensitive to proteolytic degradation by one or more proteases secreted by a plant pathogen. In this instance, detection of such proteases may be possible by incubating an AMPPP with culture supernatant of one or more plant pathogens towards which AMPPP effectiveness is sought, and determining whether or not the AMPPP is degraded exo- or endoproteolytically by one or more methods discussed above. Any microbially-derived protease activity of this nature against an AMPPP so detected could then serve as the basis for determining the site or sites of such cleavage within an AMPPP and potentially lead to the design and synthesis of amino acid substitutions and/or deletions within the AMPPP which would reduce or eliminate its susceptibility to degradation by proteases originating from a target plant pathogen.

It is possible that certain amino acid substitutions and/or deletions, while preferred in order to reduce proteolysis, will have a negative effect on AMPPP potency against one or more agriculturally important plant pathogens. Conversely, those substitutions and/or deletions which might be preferred for preserving or enhancing AMPPP potency could prove ineffective in providing resistance to one or more plant proteases. Therefore, the greatest benefit would be derived from those peptides which produce greater resistance to plant proteolysis while also preserving or enhancing some preferred feature of antibiosis, such as a high level of activity against some preferred plant pathogen as a target organism, or some other improved characteristic such as reduced phytotoxicity.

Providing resistance to proteolytic degradation of AMPPPs must also take into account the site or sites within plant tissue where a significant concentration of one or more AMPPPs is being sought. For example, if the AMPPP is desired at effective concentrations primarily in plant roots in order to provide greater resistance to disease brought about by infections at the root level, such as by fungi and/or nematodes, then resistance to root-specific protease activities would be of prime concern.

Another factor to consider in constructing AMPPPs in accordance with the present invention is the rate of proteolysis as it impacts on phytotoxicity. A specific AMPPP with potential phytotoxicity may not be functionally phytotoxic if its concentration is maintained below a certain level. Therefore, it may be desirable to modify any of the aforementioned positions to provide reduced, but not complete, resistance to proteolytic degradation, at least at positions 7 and 8. It may be possible to design an AMPPP that is degraded at a rate which avoids accumulation of phytotoxic concentrations.

AMPPP Phytotoxicity

Yet another basis for selecting preferred compositions to be used in retarding plant pathogens is phytotoxicity. AMPPPs should preferably exhibit relatively minimal toxic behavior against the plant cells or plant tissue. More particularly, modifications designed to increase antimicrobial activity or stability to protease degradation should not increase phytotoxicity. Toxic behavior can be manifested by the death, reduced growth, reduced photofixation of atmospheric carbon, reduced assimilation of nutrients such as nitrogen or phosphorus, or reduced crop yield. Therefore, it is important to provide peptides which are functionally compatible with their host.

Some relative index of phytotoxicity is therefore preferred in comparing one AMPPP to another or to natural magainins or other antibiotic compounds of actual or prospective commercial value. Such an index could be the possible effect of an AMPPP on inhibiting normal pant cell organelle function. Preferred indices are the inhibition of oxygen evolution or carbon fixation by isolated plant chloroplasts or oxygen respiration by isolated plant mitochondria, or cells. These effects could be monitored by a variety of techniques and instruments available in the art such as a Warburg apparatus or, preferably, an oxygen electrode. See, "The Use Of the Oxygen Electrode and Fluorescence Probes In Simple Measurements Of Photosynthesis," D. Walker, 1987, Hansatech Ltd., Kings Lynn, Norfolk, England.

AMPPP Size

In addition to the criteria for judging peptide-plant tissue interactions just discussed, AMPPPs in accordance with the present invention have a preferred size. The preferred size for an AMPPP modeled on a natural magainin is approximately 18–24 amino acids, and more preferably approximately 21–24 amino acids. The minimal size of 18 amino acids for an AMPPP is selected because this represents the approximate minimal size for a transmembrane peptide. A preferred minimal size of approximately 21 amino acids is chosen for an AMPPP because this size represents the approximate size of derivatives of natural magainins which have essentially complete or nearly complete activity against at least some human pathogenic microorganisms and at least some plant pathogens when tested by means discussed herein. The upper limit on length is preferably about 24 residues because this size represents an extension of the AMPPPs in accordance with the present invention that include an N-terminal Met or (f) Met.

Preferred substitutions of Magainin 1 in accordance with the present invention include the compositions having the sequence of formula (I) where $Xaa^{22}$ is Lys, wherein $Xaa^{6}$ is an amino acid selected from the group consisting of Asn, Pro, 3Hyp, Ile, 4Hyp, and Leu, $Xaa^{7}$ is an amino acid selected from the group consisting of Phe, Ala, Met, Ser, Thr, Trp, Tyr, 3,4-dihydroxyphenylalanine, Gln, Pro, 3Hyp, 4Hyp, Lys, Asn, Glu, His, Asp, Orn, and Arg, $Xaa^{8}$ is an amino acid selected from the group consisting of Ala, Met, Pro, 3Hyp, 4Hyp, Thr, Ser, Trp, Tyr, 3,4-dihydroxyphenylalanine, Gln, Lys, Asn, Glu, His, Asp, Orn, and Arg, $Xaa^{10}$ is an amino acid selected from the group consisting of Gly, Leu, Ile, Val, Ala, Phe, Met, Thr, Ser, Trp, Tyr, 3,4 -dihydroxyphenylalanine, Gln, Lys, Asn, Glu, His, Asp, Orn, and Arg, $Xaa^{11}$ is an amino acid selected from the group consisting of Met, Trp, Tyr, 3,4 -dihydroxyphenylalanine, Gln, Lys, His, Pro, 3Hyp, 4Hyp, Ser, Orn, and Arg, $Xaa^{13}$ is an amino acid selected from the group consisting of Leu, Ile, Trp, Phe, Val, Ala, Gly, Pro, 3Hyp, and 4Hyp, $Xaa^{18}$ is an amino acid selected from the group consisting of Thr, Trp, Tyr, Asp, Glu, Lys, Arg, Gln, His, Met, Ala, Gly, Pro, 3Hyp, and 4Hyp, Xaa 19 is an amino acid selected from the group consisting of Ala, Glu, Pro, 3Hyp, and 4Hyp, and $Xaa^{21}$ and $Xaa^{23}$ may be the same or different and are selected from the group consisting of Arg, Orn, Asp, His, Glu, Lys, Gln, Tyr, Thr, 3,4-dihydroxyphenylalanine, Trp, Met, Asn, Ser, Ala, Phe, Val, Ile, Leu, Pro, 3Hyp and 4Hyp. Magainin 1 substituted with one or more of these amino acids at the positions indicated are preferred because of their utility in retarding plant pathogens. The terms "retard" and "retarding" as used herein mean inhibition, destruction, and/or deactivation. Thus, the peptides in accordance with the present invention need not necessarily kill the target plant pathogen, but need only impede its progress in otherwise infecting a plant.

In accordance with a more preferred aspect, substitutions in accordance with the present invention include compositions having the sequence of formula (I), where $Xaa^{22}$ is Lys and wherein $Xaa^{6}$ is Leu, $Xaa^{7}$ is an amino acid selected from the group consisting of Phe, Ser, Asp, Glu, Ala, Met, Thr, Tyr, Gln, Lys, His and Arg, $Xaa^{8}$ is an amino acid selected from the group consisting of Ser, Ala, Met, Thr, Trp, Tyr, Gln, Lys, Asn, Glu, His, Asp and Arg, $Xaa^{10}$ is an amino acid selected from the group consisting of Gly, Leu, Val, Ala, Met, Thr, Ser, Trp, Tyr, Gln, Lys, Asn, Glu, His, Asp and Arg, $Xaa^{11}$ is an amino acid selected from the group consisting of Met, Trp, Tyr, Gln, Lys, His, Ser, and Arg, $Xaa^{13}$ is an amino acid selected from the group consisting of Ala, Gly, Leu, Ile, Trp, Phe, and Val, $Xaa^{18}$ is an amino acid selected from the group consisting of Ala, Gly, Thr, Trp, Tyr, Asp, Glu, Lys, Arg, Gln, His and Met, $Xaa^{19}$ is an amino acid selected from the group consisting of Ala and Glu, $Xaa^{21}$ is an amino acid selected from the group consisting of Arg, Asp, His, Glu, Lys, Gln, Tyr, Thr, Trp, Met, and Ala, and $Xaa^{23}$ is an amino acid selected from the group consisting of Ser, Val, Ala, Leu, Ile, Pro, 3Hyp, 4Hyp, Trp, Phe, Thr, His, Gln and Tyr, wherein at least one of $Xaa^{7}$, $Xaa^{8}$, $Xaa^{10}$, $Xaa^{11}$, $Xaa^{13}$, $Xaa^{18}$, $Xaa^{19}$, $Xaa^{21}$ or $Xaa^{23}$ is substituted when compared to Magainin 1.

Some of the more preferred substitutions of AMPPs where $Xaa^{22}$ is Lys are substitutions of Magainin 1 in accordance with the present invention which include $Ala^{13}$, $Ala^{18}$; $Lys^{7}$; $Arg^{7}$; $Ala^{7}$; $Phe^{7}$; $Thr^{8}$; $Glu^{8}$; $Lys^{10}$; $Ala^{18}$; $Ala^{19}$; $Arg^{7}$, $Thr^{8}$; $Arg^{7}$, Glu8; $Arg^{7}$, $Ala^{8}$; $Lys^{7}$, $Thr^{8}$; $Lys^{7}$, $Ala^{8}$; $Lys^{7}$, $Glu^{8}$; $Ala^{7}$, $Thr^{8}$; $Ala^{7}$, $Glu^{8}$; $Ala^{7}$ $Ala^{8}$; $Phe^{7}$, $Thr^{8}$; $Phe^{7}$, $Ala^{8}$; $Phe^{7}$, $Glu^{8}$; $Pro^{11}$; $His^{10}$; $His^{11}$; and $His^{10}$, $His^{11}$.

Naturally occurring Magainin 1 and Magainin 2 are active against animal pathogens and as found in the African clawed frog *Xenopus laevis* have no methionyl residue, whether Met or (f)Met, at the N-terminal end. This is not surprising because they originate as peptides processed from a larger preprotein.

Active AMPPPs constructed in accordance with the teachings of this invention can, and in certain instances desirably do, have N-terminal methionyl residues, i.e., (f)Met or Met. This is a significant discovery because the need for cellular processing of AMPPPs constructed as set forth herein is significantly reduced, if not eliminated. Thus, AMPPPs engineered to have Met or (f)Met at their N-terminal end, whether by addition of a methionyl residue or by deletion and/or substitution of other amino acid residues coupled with the addition of a methionyl residue, exhibit antimicrobial activity without further cellular processing. Exploitation of this discovery will not only greatly facilitate development of products for agricultural use, but will facilitate genetically engineered production of AMPPPs.

The extension of an AMPPP by the addition of one of the amino acids Met or (f)Met to the amino terminus of an AMPPP is therefore also among the preferred aspects in accordance with the present invention because proteins produced in nature generally have a Met at the amino terminus. Bacterial proteins, however, generally initiate protein synthesis by introducing an N-formylated Met or (f)Met at the N-terminus followed by post-translational removal of the formyl group. Unlike naturally occurring Magainin 1 and 2 therefore, or magainin derivatives produced in eucaryotic cells, some or all of the active AMPPP produced by bacteria should include an (f)Met amino acid at the N-terminus.

AMPPPs of the present invention involve certain specific single and double residue omission derivatives. These AMPPPs retain their antimicrobial activity against plant pathogens despite the fact that similar compounds had previously been reported to be ineffective in treatment of human bacterial pathogens. For example, [Des $Gly^{1}$]Mag 1 and [Des $Gly^{1}$, Des $Ile^{2}$]-Mag 1 were both efficacious in treatment of specific plant pathogens such as P3 Fusarium despite a report that [Des $Gly^1$]Mag 1 is not active against the human pathogens *Escherichia coli, Staphylococcus epidermis* or *Candida albicans*. See Cuervo et al., *Peptide Res.*, supra.

Some of the preferred deletions and/or extensions of Magainin 1 in accordance with the present invention are Met-; Met [$Ala^{13}$, $Ala^{18}$]; [Des $Gly^1$, Des $Ile^2$]; Met [Des $Met^{21}$]; Met [Des $Lys^{22}$, Des $Ser^{23}$]; and [Des $Lys^{22}$, Des $Ser^{23}$]. Recall that "Des" indicates a deletion and the number in superscript indicates the position relative to the N-terminal Gly or N-terminus as previously defined, "Met" indicates the Met residue addition to the N-terminus, and the remaining three letter combinations indicate the amino acid which is substituted for the naturally occurring amino acid in the position or positions indicated by the corresponding superscript number.

Combinations of the aforementioned AMPPP constructions are also contemplated such as, for example, [$Arg^7$, $Glu^8$, $Ala^{13}$, $Ala^{18}$, Des Lys $^{22}$, Des $Ser^{23}$]Mag 1, Met[$Phe^7$]Mag 1, or [$Lys^7$, $Glu^8$, $Ala^{19}$]Mag 1. Further, substitutions in other positions, such as, for example, $Xaa^6$ or $Xaa^{21}$, may be combined with the aforementioned substitutions, deletions, and/or extensions. This is with the proviso that the resulting peptide is not Magainin 1 or just a single residue omission analog of Magainin 1.

Similar substitutions, deletions, and/or extensions of Magainin 2 are also contemplated. These include the preferred and more preferred substitutions described above as well as the preferred deletions and extensions described with regard to Magainin 1. However, in these cases, $Xaa^{22}$ is Asn. This is with the proviso that the resulting peptide is not Magainin 2, Magainin 2 substituted only in two or more of $Xaa^8$, Xaa13, or $Xaa^{18}$ with Ala, Magainin 2 substituted with only one Ala, a single residue omission analog of Magainin 2 without other substitutions and/or extensions, [Des $Gly^1$, Des $Ile^2$]-Mag 2 or Magainin 2 substituted only in position 21 ($Xaa^{21}$). Therefore, some of the most preferred substitutions as well as some of the preferred deletions and/or extensions of Magainin 2 in accordance with the present invention include $Lys^7$; $Arg^7$; $Ala^7$; $Phe^7$; $Thr^8$; $Glu^8$; $Lys^{10}$; $Arg^7$, $Thr^8$; $Arg^7$, $Glu^8$; $Arg^7$, $Ala^8$; $Lys^7$, $Thr^8$; $Lys^7$, $Ala^8$; $Lys^7$, $Glu^8$; $Ala^7$, $Thr^8$, $Ala^7$, $Glu^8$; $Ala^7$, $Ala^8$; $Phe^7$, $Thr^8$; $Phe^7$, $Ala^8$; $Phe^7$, $Glu^8$; $Pro^{11}$; $His^{10}$; $His^{11}$; $His^{10}$, $His^{11}$; Met-; Met[$Ala^{13}$, $Ala^{18}$]; Met[Des $Gly^1$, Des $Ile^2$]; Met[Des $Met^{21}$]; Met[Des $Asn^{22}$, Des $Ser^{23}$]; and/or [Des $Asn^{22}$, Des $Ser^{23}$].

AMPPP constructions akin to the aforediscussed substitutions, deletions, and/or extensions may be made in magainin derived peptides which are not Magainin 1 or Magainin 2. That is to say, strictly speaking, these peptides are not Magainin 1 or Magainin 2 or direct derivatives thereof. Such AMPPPs would not include a Lys or Asn in position 22 and the corresponding Gly or Lys, respectively, at position 10. These include, for example, in a preferred embodiment, compositions having the sequence of formula (I) wherein $Xaa^{22}$ is an amino acid selected from the group consisting of Arg, Orn, Asp, His, Glu, Lys, Gln, Tyr, 3,4-dihydroxyphenylalanine, Trp, Met, Asn, Ala, Pro, 3Hyp, Ser, Thr, and 4Hyp, and wherein $Xaa^6$ is an amino acid selected from the group consisting of Asn, Pro, 3Hyp, 4Hyp, Ile, and Leu, $Xaa^7$ is an amino acid selected from the group consisting of Phe, Ala, Met, Ser, Thr, Trp, Tyr, 3,4-dihydroxyphenylalanine, Gln, Pro, 3Hyp, 4Hyp, Lys, Asn, Glu, His, Asp, Orn, and Arg, $Xaa^8$ is an amino acid selected from the group consisting of Ala, Met, Pro, 3Hyp, 4Hyp, Thr, Ser, Trp, Tyr, 3,4-dihydroxyphenylalanine, Gln, Lys, Asn, Glu, His, Asp, Orn, and Arg, $Xaa^{10}$ is an amino acid selected from the group consisting of Gly, Leu, Ile, Val, Ala, Phe, Met, Thr, Ser, Trp, Tyr, 3,4-dihydroxyphenylalanine, Gln, Lys, Asn, Glu, His, Asp, Orn, and Arg, $Xaa^{11}$ is an amino acid selected from the group consisting of Met, Trp, Tyr, 3,4-dihydroxyphenylalanine, Gln, Lys, His, Pro, 3Hyp, 4Hyp, Ser, Orn, and Arg, $Xaa^{13}$ is an amino acid selected from the group consisting of Leu, Ile, Trp, Phe, Val, Ala, Gly, Pro, 3Hyp, and 4Hyp, $Xaa^{18}$ is an amino acid selected from the group consisting of Thr, Trp, Tyr, Asp, Glu, Lys, Arg, Gln, His, Met, Ala, Gly, Pro, 3Hyp, and 4Hyp, $Xaa^{19}$ is an amino acid selected from the group consisting of Ala, Glu, Pro, 3Hyp, and 4Hyp, and $Xaa^{21}$ and $Xaa^{23}$ may be the same or different and are selected from the group consisting of Arg, Orn, Asp, His, Glu, Lys, Gln, Tyr, Thr, 3,4-dihydroxyphenylalanine, Trp, Met, Asn, Ser, Ala, Phe, Val, Ile, Leu, Pro, 3Hyp and 4Hyp.

In accordance with a more preferred aspect of the present invention, antimicrobial peptides which are not substitution, omission or addition derivatives of Magainin 1 or Magainin 2 include compositions having the sequence of formula (I) wherein $Xaa^{22}$ is an amino acid selected from the group consisting of Lys, Asn, Arg, Asp, His, Glu, Lys, Gln, Tyr, Thr, Trp, Met, and Ala, $Xaa^6$ is Leu, $Xaa^7$ is an amino acid selected from the group consisting of Phe, Asp, Glu, Ser, Ala, Met, Thr, Tyr, Gln, Lys, His and Arg, $Xaa^8$ is an amino acid selected from the group consisting of Ser, Ala, Met, Thr, Trp, Tyr, Gln, Lys, Asn, Glu, His, Asp and Arg, $Xaa^{10}$ is an amino acid selected from the group consisting of Gly, Leu, Val, Ala, Met, Thr, Ser, Trp, Tyr, Gln, Lys, Asn, Glu, His, Asp and Arg, $Xaa^{11}$ is an amino acid selected from the group consisting of Met, Trp, Tyr, Gln, Lys, His, Ser, and Arg, $Xaa^{13}$ is an amino acid selected from the group consisting of Ala, Gly, Leu, Ile, Trp, Phe, and Val, $Xaa^{18}$ is an amino acid selected from the group consisting of Ala, Gly, Thr, Trp, Tyr, Asp, Glu, Lys, Arg, Gln, His and Met, $Xaa^{19}$ is an amino acid selected from the group consisting of Ala and Glu, $Xaa^{21}$ is an amino acid selected from the group consisting of Arg, Asp, His, Glu, Lys, Gln, Tyr, Thr, Trp, Met, and Ala, and $Xaa^{23}$ is an amino acid selected from the group consisting of Ser, Val, Ala, Leu, Thr, Pro, 3Hyp, 4Hyp, Ile, Trp, Phe, His, Gln and Tyr.

These substitutions may be combined with other substitutions, deletions, and/or extensions to provide a peptide which is not only resistant to plant proteolysis, but also one with increased activity against one or more plant pathogens, selected activity against specific plant pathogens, and/or low phytotoxicity.

Also illustrative of the AMPPPs which fall within the scope of this invention are the peptides having the following sequences. Note that the amino acids listed conform to standard usages except that DOPA represents 3,4-dihydroxyphenylalanine and f(Met) represents N-formylated Met.

GlyIleGlyLysPheLeuArgSerAlaGlyLysPheGlyLysAlaPheValGlyGluIleMetLysSer
GlyIleGlyLysPheLeuLysSerAlaGlyLysPheGlyLysAlaPheValGlyGluIleMetLysSer
GlyIleGlyLysPheLeuPheSerAlaGlyLysPheGlyLysAlaPheValGlyGluIleMetLysSer

-continued

GlyIleGlyLysPheLeuGluSerAlaGlyLysPheGlyLysAlaPheValGlyGluIleMetLysSer
GlyIleGlyLysPheLeuAspSerAlaGlyLysPheGlyLysAlaPheValGlyGluIleMetLysSer
GlyIleGlyLysPheLeuMetSerAlaGlyLysPheGlyLysAlaPheValGlyGluIleMetLysSer
GlyIleGlyLysPheLeuTyrSerAlaGlyLysPheGlyLysAlaPheValGlyGluIleMetLysSer
GlyIleGlyLysPheLeuAlaSerAlaGlyLysPheGlyLysAlaPheValGlyGluIleMetLysSer
GlyIleGlyLysPheLeuHisAlaAlaGlyLysPheGlyLysAlaPheValGlyGluIleMetLysSer
GlyIleGlyLysPheLeuHisGluAlaGlyLysPheGlyLysAlaPheValGlyGluIleMetLysSer
GlyIleGlyLysPheLeuHisThrAlaGlyLysPheGlyLysAlaPheValGlyGluIleMetLysSer
GlyIleGlyLysPheLeuHisTyrAlaGlyLysPheGlyLysAlaPheValGlyGluIleMetLysSer
GlyIleGlyLysPheLeuHisLysAlaGlyLysPheGlyLysAlaPheValGlyGluIleMetLysSer
GlyIleGlyLysPheLeuHisArgAlaGlyLysPheGlyLysAlaPheValGlyGluIleMetLysSer
GlyIleGlyLysPheLeuHisAspAlaGlyLysPheGlyLysAlaPheValGlyGluIleMetLysSer
GlyIleGlyLysPheLeuHisTrpAlaGlyLysPheGlyLysAlaPheValGlyGluIleMetLysSer
GlyIleGlyLysPheLeuLysAlaAlaGlyLysPheGlyLysAlaPheValGlyGluIleMetLysSer
GlyIleGlyLysPheLeuLysGluAlaGlyLysPheGlyLysAlaPheValGlyGluIleMetLysSer
GlyIleGlyLysPheLeuLysThrAlaGlyLysPheGlyLysAlaPheValGlyGluIleMetLysSer
GlyIleGlyLysPheLeuLysTrpAlaGlyLysPheGlyLysAlaPheValGlyGluIleMetLysSer
GlyIleGlyLysPheLeuLysMetAlaGlyLysPheGlyLysAlaPheValGlyGluIleMetLysSer
GlyIleGlyLysPheLeuArgAlaAlaGlyLysPheGlyLysAlaPheValGlyGluIleMetLysSer
GlyIleGlyLysPheLeuArgGluAlaGlyLysPheGlyLysAlaPheValGlyGluIleMetLysSer
GlyIleGlyLysPheLeuArgThrAlaGlyLysPheGlyLysAlaPheValGlyGluIleMetLysSer
GlyIleGlyLysPheLeuArgTrpAlaGlyLysPheGlyLysAlaPheValGlyGluIleMetLysSer
GlyIleGlyLysPheLeuArgMetAlaGlyLysPheGlyLysAlaPheValGlyGluIleMetLysSer
GlyIleGlyLysPheLeuPheAlaAlaGlyLysPheGlyLysAlaPheValGlyGluIleMetLysSer
GlyIleGlyLysPheLeuPheGluAlaGlyLysPheGlyLysAlaPheValGlyGluIleMetLysSer
GlyIleGlyLysPheLeuPheThrAlaGlyLysPheGlyLysAlaPheValGlyGluIleMetLysSer
GlyIleGlyLysPheLeuPheTrpAlaGlyLysPheGlyLysAlaPheValGlyGluIleMetLysSer
GlyIleGlyLysPheLeuPheMetAlaGlyLysPheGlyLysAlaPheValGlyGluIleMetLysSer
GlyIleGlyLysPheLeuGluAlaAlaGlyLysPheGlyLysAlaPheValGlyGluIleMetLysSer
GlyIleGlyLysPheLeuGluGluAlaGlyLysPheGlyLysAlaPheValGlyGluIleMetLysSer
GlyIleGlyLysPheLeuGluThrAlaGlyLysPheGlyLysAlaPheValGlyGluIleMetLysSer
GlyIleGlyLysPheLeuGluTrpAlaGlyLysPheGlyLysAlaPheValGlyGluIleMetLysSer
GlyIleGlyLysPheLeuGluMetAlaGlyLysPheGlyLysAlaPheValGlyGluIleMetLysSer
GlyIleGlyLysPheLeuMetAlaAlaGlyLysPheGlyLysAlaPheValGlyGluIleMetLysSer
GlyIleGlyLysPheLeuMetGluAlaGlyLysPheGlyLysAlaPheValGlyGluIleMetLysSer
GlyIleGlyLysPheLeuMetThrAlaGlyLysPheGlyLysAlaPheValGlyGluIleMetLysSer
GlyIleGlyLysPheLeuMetTrpAlaGlyLysPheGlyLysAlaPheValGlyGluIleMetLysSer
GlyIleGlyLysPheLeuMetMetAlaGlyLysPheGlyLysAlaPheValGlyGluIleMetLysSer
GlyIleGlyLysPheLeuGlnAlaAlaGlyLysPheGlyLysAlaPheValGlyGluIleMetLysSer
GlyIleGlyLysPheLeuGlnGluAlaGlyLysPheGlyLysAlaPheValGlyGluIleMetLysSer
GlyIleGlyLysPheLeuGlnThrAlaGlyLysPheGlyLysAlaPheValGlyGluIleMetLysSer
GlyIleGlyLysPheLeuGlnTrpAlaGlyLysPheGlyLysAlaPheValGlyGluIleMetLysSer
GlyIleGlyLysPheLeuGlnMetAlaGlyLysPheGlyLysAlaPheValGlyGluIleMetLysSer
IleGlyLysPheLeuArgSerAlaGlyLysPheGlyLysAlaPheValGlyGluIleMetLysSer
IleGlyLysPheLeuLysSerAlaGlyLysPheGlyLysAlaPheValGlyGluIleMetLysSer
IleGlyLysPheLeuPheSerAlaGlyLysPheGlyLysAlaPheValGlyGluIleMetLysSer
IleGlyLysPheLeuGluSerAlaGlyLysPheGlyLysAlaPheValGlyGluIleMetLysSer
IleGlyLysPheLeuAspSerAlaGlyLysPheGlyLysAlaPheValGlyGluIleMetLysSer
IleGlyLysPheLeuMetSerAlaGlyLysPheGlyLysAlaPheValGlyGluIleMetLysSer
IleGlyLysPheLeuTyrSerAlaGlyLysPheGlyLysAlaPheValGlyGluIleMetLysSer
IleGlyLysPheLeuAlaSerAlaGlyLysPheGlyLysAlaPheValGlyGluIleMetLysSer
IleGlyLysPheLeuHisAlaAlaGlyLysPheGlyLysAlaPheValGlyGluIleMetLysSer
IleGlyLysPheLeuHisGluAlaGlyLysPheGlyLysAlaPheValGlyGluIleMetLysSer
IleGlyLysPheLeuHisThrAlaGlyLysPheGlyLysAlaPheValGlyGluIleMetLysSer
IleGlyLysPheLeuHisMetAlaGlyLysPheGlyLysAlaPheValGlyGluIleMetLysSer
IleGlyLysPheLeuHisTyrAlaGlyLysPheGlyLysAlaPheValGlyGluIleMetLysSer
IleGlyLysPheLeuHisLysAlaGlyLysPheGlyLysAlaPheValGlyGluIleMetLysSer
IleGlyLysPheLeuHisArgAlaGlyLysPheGlyLysAlaPheValGlyGluIleMetLysSer
IleGlyLysPheLeuHisAspAlaGlyLysPheGlyLysAlaPheValGlyGluIleMetLysSer
IleGlyLysPheLeuHisTrpAlaGlyLysPheGlyLysAlaPheValGlyGluIleMetLysSer
IleGlyLysPheLeuLysAlaAlaGlyLysPheGlyLysAlaPheValGlyGluIleMetLysSer
IleGlyLysPheLeuLysGluAlaGlyLysPheGlyLysAlaPheValGlyGluIleMetLysSer
IleGlyLysPheLeuLysThrAlaGlyLysPheGlyLysAlaPheValGlyGluIleMetLysSer
IleGlyLysPheLeuLysTrpAlaGlyLysPheGlyLysAlaPheValGlyGluIleMetLysSer
IleGlyLysPheLeuLysMetAlaGlyLysPheGlyLysAlaPheValGlyGluIleMetLysSer
IleGlyLysPheLeuArgAlaAlaGlyLysPheGlyLysAlaPheValGlyGluIleMetLysSer
IleGlyLysPheLeuArgGluAlaGlyLysPheGlyLysAlaPheValGlyGluIleMetLysSer
IleGlyLysPheLeuArgThrAlaGlyLysPheGlyLysAlaPheValGlyGluIleMetLysSer
IleGlyLysPheLeuArgTrpAlaGlyLysPheGlyLysAlaPheValGlyGluIleMetLysSer
IleGlyLysPheLeuArgMetAlaGlyLysPheGlyLysAlaPheValGlyGluIleMetLysSer
IleGlyLysPheLeuPheAlaAlaGlyLysPheGlyLysAlaPheValGlyGluIleMetLysSer
IleGlyLysPheLeuPheGluAlaGlyLysPheGlyLysAlaPheValGlyGluIleMetLysSer
IleGlyLysPheLeuPheThrAlaGlyLysPheGlyLysAlaPheValGlyGluIleMetLysSer
IleGlyLysPheLeuPheTrpAlaGlyLysPheGlyLysAlaPheValGlyGluIleMetLysSer
IleGlyLysPheLeuPheMetAlaGlyLysPheGlyLysAlaPheValGlyGluIleMetLysSer
IleGlyLysPheLeuGluAlaAlaGlyLysPheGlyLysAlaPheValGlyGluIleMetLysSer
IleGlyLysPheLeuGluGluAlaGlyLysPheGlyLysAlaPheValGlyGluIleMetLysSer
IleGlyLysPheLeuGluThrAlaGlyLysPheGlyLysAlaPheValGlyGluIleMetLysSer
IleGlyLysPheLeuGluTrpAlaGlyLysPheGlyLysAlaPheValGlyGluIleMetLysSer
IleGlyLysPheLeuGluMetAlaGlyLysPheGlyLysAlaPheValGlyGluIleMetLysSer
IleGlyLysPheLeuMetAlaAlaGlyLysPheGlyLysAlaPheValGlyGluIleMetLysSer
IleGlyLysPheLeuMetGluAlaGlyLysPheGlyLysAlaPheValGlyGluIleMetLysSer
IleGlyLysPheLeuMetThrAlaGlyLysPheGlyLysAlaPheValGlyGluIleMetLysSer

-continued

IleGlyLysPheLeuMetTrpAlaGlyLysPheGlyLysAlaPheValGlyGluIleMetLysSer
IleGlyLysPheLeuMetMetAlaGlyLysPheGlyLysAlaPheValGlyGluIleMetLysSer
IleGlyLysPheLeuGlnAlaAlaGlyLysPheGlyLysAlaPheValGlyGluIleMetLysSer
IleGlyLysPheLeuGlnGluAlaGlyLysPheGlyLysAlaPheValGlyGluIleMetLysSer
IleGlyLysPheLeuGlnThrAlaGlyLysPheGlyLysAlaPheValGlyGluIleMetLysSer
IleGlyLysPheLeuGlnTrpAlaGlyLysPheGlyLysAlaPheValGlyGluIleMetLysSer
IleGlyLysPheLeuGlnMetAlaGlyLysPheGlyLysAlaPheValGlyGluIleMetLysSer
GlyIleGlyLysPheLeuArgSerAlaGlyLysPheGlyLysAlaPheValGlyGluIleMetLys
GlyIleGlyLysPheLeuLysSerAlaGlyLysPheGlyLysAlaPheValGlyGluIleMetLys
GlyIleGlyLysPheLeuPheSerAlaGlyLysPheGlyLysAlaPheValGlyGluIleMetLys
GlyIleGlyLysPheLeuGluSerAlaGlyLysPheGlyLysAlaPheValGlyGluIleMetLys
GlyIleGlyLysPheLeuAspSerAlaGlyLysPheGlyLysAlaPheValGlyGluIleMetLys
GlyIleGlyLysPheLeuMetSerAlaGlyLysPheGlyLysAlaPheValGlyGluIleMetLys
GlyIleGlyLysPheLeuTyrSerAlaGlyLysPheGlyLysAlaPheValGlyGluIleMetLys
GlyIleGlyLysPheLeuAlaSerAlaGlyLysPheGlyLysAlaPheValGlyGluIleMetLys
GlyIleGlyLysPheLeuHisAlaAlaGlyLysPheGlyLysAlaPheValGlyGluIleMetLys
GlyIleGlyLysPheLeuHisGluAlaGlyLysPheGlyLysAlaPheValGlyGluIleMetLys
GlyIleGlyLysPheLeuHisThrAlaGlyLysPheGlyLysAlaPheValGlyGluIleMetLys
GlyIleGlyLysPheLeuHisMetAlaGlyLysPheGlyLysAlaPheValGlyGluIleMetLys
GlyIleGlyLysPheLeuHisTyrAlaGlyLysPheGlyLysAlaPheValGlyGluIleMetLys
GlyIleGlyLysPheLeuHisLysAlaGlyLysPheGlyLysAlaPheValGlyGluIleMetLys
GlyIleGlyLysPheLeuHisArgAlaGlyLysPheGlyLysAlaPheValGlyGluIleMetLys
GlyIleGlyLysPheLeuHisAspAlaGlyLysPheGlyLysAlaPheValGlyGluIleMetLys
GlyIleGlyLysPheLeuHisTrpAlaGlyLysPheGlyLysAlaPheValGlyGluIleMetLys
GlyIleGlyLysPheLeuLysAlaAlaGlyLysPheGlyLysAlaPheValGlyGluIleMetLys
GlyIleGlyLysPheLeuLysGluAlaGlyLysPheGlyLysAlaPheValGlyGluIleMetLys
GlyIleGlyLysPheLeuLysThrAlaGlyLysPheGlyLysAlaPheValGlyGluIleMetLys
GlyIleGlyLysPheLeuLysTrpAlaGlyLysPheGlyLysAlaPheValGlyGluIleMetLys
GlyIleGlyLysPheLeuLysMetAlaGlyLysPheGlyLysAlaPheValGlyGluIleMetLys
GlyIleGlyLysPheLeuArgAlaAlaGlyLysPheGlyLysAlaPheValGlyGluIleMetLys
GlyIleGlyLysPheLeuArgGluAlaGlyLysPheGlyLysAlaPheValGlyGluIleMetLys
GlyIleGlyLysPheLeuArgThrAlaGlyLysPheGlyLysAlaPheValGlyGluIleMetLys
GlyIleGlyLysPheLeuArgTrpAlaGlyLysPheGlyLysAlaPheValGlyGluIleMetLys
GlyIleGlyLysPheLeuArgMetAlaGlyLysPheGlyLysAlaPheValGlyGluIleMetLys
GlyIleGlyLysPheLeuPheAlaAlaGlyLysPheGlyLysAlaPheValGlyGluIleMetLys
GlyIleGlyLysPheLeuPheGluAlaGlyLysPheGlyLysAlaPheValGlyGluIleMetLys
GlyIleGlyLysPheLeuPheThrAlaGlyLysPheGlyLysAlaPheValGlyGluIleMetLys
GlyIleGlyLysPheLeuPheTrpAlaGlyLysPheGlyLysAlaPheValGlyGluIleMetLys
GlyIleGlyLysPheLeuPheMetAlaGlyLysPheGlyLysAlaPheValGlyGluIleMetLys
GlyIleGlyLysPheLeuGluAlaAlaGlyLysPheGlyLysAlaPheValGlyGluIleMetLys
GlyIleGlyLysPheLeuGluGluAlaGlyLysPheGlyLysAlaPheValGlyGluIleMetLys
GlyIleGlyLysPheLeuGluThrAlaGlyLysPheGlyLysAlaPheValGlyGluIleMetLys
GlyIleGlyLysPheLeuGluTrpAlaGlyLysPheGlyLysAlaPheValGlyGluIleMetLys
GlyIleGlyLysPheLeuGluMetAlaGlyLysPheGlyLysAlaPheValGlyGluIleMetLys
GlyIleGlyLysPheLeuMetAlaAlaGlyLysPheGlyLysAlaPheValGlyGluIleMetLys
GlyIleGlyLysPheLeuMetGluAlaGlyLysPheGlyLysAlaPheValGlyGluIleMetLys
GlyIleGlyLysPheLeuMetThrAlaGlyLysPheGlyLysAlaPheValGlyGluIleMetLys
GlyIleGlyLysPheLeuMetTrpAlaGlyLysPheGlyLysAlaPheValGlyGluIleMetLys
GlyIleGlyLysPheLeuMetMetAlaGlyLysPheGlyLysAlaPheValGlyGluIleMetLys
GlyIleGlyLysPheLeuGlnAlaAlaGlyLysPheGlyLysAlaPheValGlyGluIleMetLys
GlyIleGlyLysPheLeuGlnGluAlaGlyLysPheGlyLysAlaPheValGlyGluIleMetLys
GlyIleGlyLysPheLeuGlnThrAlaGlyLysPheGlyLysAlaPheValGlyGluIleMetLys
GlyIleGlyLysPheLeuGlnTrpAlaGlyLysPheGlyLysAlaPheValGlyGluIleMetLys
GlyIleGlyLysPheLeuGlnMetAlaGlyLysPheGlyLysAlaPheValGlyGluIleMetLys
GlyLysPheLeuHisSerAlaGlyLysPheGlyLysAlaPheValGlyGluIleMetLysSer
GlyLysPheLeuArgSerAlaGlyLysPheGlyLysAlaPheValGlyGluIleMetLysSer
GlyLysPheLeuLysSerAlaGlyLysPheGlyLysAlaPheValGlyGluIleMetLysSer
GlyLysPheLeuPheSerAlaGlyLysPheGlyLysAlaPheValGlyGluIleMetLysSer
GlyLysPheLeuGluSerAlaGlyLysPheGlyLysAlaPheValGlyGluIleMetLysSer
GlyLysPheLeuAspSerAlaGlyLysPheGlyLysAlaPheValGlyGluIleMetLysSer
GlyLysPheLeuMetSerAlaGlyLysPheGlyLysAlaPheValGlyGluIleMetLysSer
GlyLysPheLeuTyrSerAlaGlyLysPheGlyLysAlaPheValGlyGluIleMetLysSer
GlyLysPheLeuAlaSerAlaGlyLysPheGlyLysAlaPheValGlyGluIleMetLysSer
GlyLysPheLeuHisAlaAlaGlyLysPheGlyLysAlaPheValGlyGluIleMetLysSer
GlyLysPheLeuHisGluAlaGlyLysPheGlyLysAlaPheValGlyGluIleMetLysSer
GlyLysPheLeuHisThrAlaGlyLysPheGlyLysAlaPheValGlyGluIleMetLysSer
GlyLysPheLeuHisMetAlaGlyLysPheGlyLysAlaPheValGlyGluIleMetLysSer
GlyLysPheLeuHisTyrAlaGlyLysPheGlyLysAlaPheValGlyGluIleMetLysSer
GlyLysPheLeuHisLysAlaGlyLysPheGlyLysAlaPheValGlyGluIleMetLysSer
GlyLysPheLeuHisArgAlaGlyLysPheGlyLysAlaPheValGlyGluIleMetLysSer
GlyLysPheLeuHisAspAlaGlyLysPheGlyLysAlaPheValGlyGluIleMetLysSer
GlyLysPheLeuHisTrpAlaGlyLysPheGlyLysAlaPheValGlyGluIleMetLysSer
GlyLysPheLeuLysAlaAlaGlyLysPheGlyLysAlaPheValGlyGluIleMetLysSer
GlyLysPheLeuLysGluAlaGlyLysPheGlyLysAlaPheValGlyGluIleMetLysSer
GlyLysPheLeuLysThrAlaGlyLysPheGlyLysAlaPheValGlyGluIleMetLysSer
GlyLysPheLeuLysTrpAlaGlyLysPheGlyLysAlaPheValGlyGluIleMetLysSer
GlyLysPheLeuLysMetAlaGlyLysPheGlyLysAlaPheValGlyGluIleMetLysSer
GlyLysPheLeuArgAlaAlaGlyLysPheGlyLysAlaPheValOlyGluIleMetLysSer
GlyLysPheLeuArgGluAlaGlyLysPheGlyLysAlaPheValGlyGluIleMetLysSer
GlyLysPheLeuArgThrAlaGlyLysPheGlyLysAlaPheValGlyGluIleMetLysSer
GlyLysPheLeuArgTrpAlaGlyLysPheGlyLysAlaPheValGlyGluIleMetLysSer
GlyLysPheLeuArgMetAlaGlyLysPheGlyLysAlaPheValGlyGluIleMetLysSer
GlyLysPheLeuPheAlaAlaGlyLysPheGlyLysAlaPheValGlyGluIleMetLysSer

-continued

GlyLysPheLeuPheGluAlaGlyLysPheGlyLysAlaPheValGlyGluIleMetLysSer
GlyLysPheLeuPheThrAlaGlyLysPheGlyLysAlaPheValGlyGluIleMetLysSer
GlyLysPheLeuPheTrpAlaGlyLysPheGlyLysAlaPheValGlyGluIleMetLysSer
GlyLysPheLeuPheMetAlaGlyLysPheGlyLysAlaPheValGlyoluIleX&tLysSer
GlyLysPheLeuGluAlaAlaGlyLysPheGlyLysAlaPheValGlyGluIleMetLysSer
GlyLysPheLeuGluGluAlaGlyLysPheGlyLysAlaPheValGlyGluIleMetLysSer
GlyLysPheLeuGluThrAlaGlyLysPheGlyLysAlaPheValGlyGluIleMetLysSer
GlyLysPheLeuGluTrpAlaGlyLysPheGlyLysAlaPheValGlyGluIleMetLysSer
GlyLysPheLeuGluMetAlaGlyLysPheGlyLysAlaPheValGlyGluIleMetLysSer
GlyLysPheLeuMetAlaAlaGlyLysPheGlyLysAlaPheValGlyGluIleMetLysSer
GlyLysPheLeuMetGluAlaGlyLysPheGlyLysAlaPheValGlyGluIleMetLysSer
GlyLysPheLeuMetThrAlaGlyLysPheGlyLysAlaPheValGlyGluIleMetLysSer
GlyLysPheLeuMetTrpAlaGlyLysPheGlyLysAlaPheValGlyGluIleMetLysSer
GlyLysPheLeuMetMetAlaGlyLysPheGlyLysAlaPheValGlyGluIleMetLysSer
GlyLysPheLeuGlnAlaAlaGlyLysPheGlyLysAlaPheValGlyGluIleMetLysSer
GlyLysPheLeuGlnGluAlaGlyLysPheGlyLysAlaPheValGlyGluIleMetLysSer
GlyLysPheLeuGlnThrAlaGlyLysPheGlyLysAlaPheValGlyGluIleMetLysSer
GlyLysPheLeuGlnTrpAlaGlyLysPheGlyLysAlaPheValGlyGluIleMetLysSer
GlyLysPheLeuGlnMetAlaGlyLysPheGlyLysAlaPheValGlyGluIleMetLysSer
GlyIleGlyLysPheLeuHisSerAlaGlyLysPheGlyLysAlaPheValGlyGluIleMet
GlyIleGlyLysPheLeuArgSerAlaGlyLysPheGlyLysAlaPheValGlyGluIleMet
GlyIleGlyLysPheLeuLysSerAlaGlyLysPheGlyLysAlaPheValGlyGluIleMet
GlyIleGlyLysPheLeuPheSerAlaGlyLysPheGlyLysAlaPheValGlyGluIleMet
GlyIleGlyLysPheLeuGluSerAlaGlyLysPheGlyLysAlaPheValGlyGluIleMet
GlyIleGlyLysPheLeuAspSerAlaGlyLysPheGlyLysAlaPheValGlyGluIleMet
GlyIleGlyLysPheLeuMetSerAlaGlyLysPheGlyLysAlaPheValGlyGluIleMet
GlyIleGlyLysPheLeuTyrSerAlaGlyLysPheGlyLysAlaPheValGlyGluIleMet
GlyIleGlyLysPheLeuAlaSerAlaGlyLysPheGlyLysAlaPheValGlyGluIleMet
GlyIleGlyLysPheLeuHisAlaAlaGlyLysPheGlyLysAlaPheValGlyGluIleMet
GlyIleGlyLysPheLeuHisGluAlaGlyLysPheGlyLysAlaPheValGlyGluIleMet
GlyIleGlyLysPheLeuHisThrAlaGlyLysPheGlyLysAlaPheValGlyGluIleMet
GlyIleGlyLysPheLeuHisMetAlaGlyLysPheGlyLysAlaPheValGlyGluIleMet
GlyIleGlyLysPheLeuHisTyrAlaGlyLysPheGlyLysAlaPheValGlyGluIleMet
GlyIleGlyLysPheLeuHisLysAlaGlyLysPheGlyLysAlaPheValGlyGluIleMet
GlyIleGlyLysPheLeuHisArgAlaGlyLysPheGlyLysAlaPheValGlyGluIleMet
GlyIleGlyLysPheLeuHisAspAlaGlyLysPheGlyLysAlaPheValGlyGluIleMet
GlyIleGlyLysPheLeuHisTrpAlaGlyLysPheGlyLysAlaPheValGlyGluIleMet
GlyIleGlyLysPheLeuLysAlaAlaGlyLysPheGlyLysAlaPheValGlyGluIleMet
GlyIleGlyLysPheLeuLysGluAlaGlyLysPheGlyLysAlaPheValGlyGluIleMet
GlyIleGlyLysPheLeuLysThrAlaGlyLysPheGlyLysAlaPheValGlyGluIleMet
GlyIleGlyLysPheLeuLysTrpAlaGlyLysPheGlyLysAlaPheValGlyGluIleMet
GlyIleGlyLysPheLeuLysMetAlaGlyLysPheGlyLysAlaPheValGlyGluIleMet
GlyIleGlyLysPheLeuArgAlaAlaGlyLysPheGlyLysAlaPheValGlyGluIleMet
GlyIleGlyLysPheLeuArgGluAlaGlyLysPheGlyLysAlaPheValGlyGluIleMet
GlyIleGlyLysPheLeuArgThrAlaGlyLysPheGlyLysAlaPheValGlyGluIleMet
GlyIleGlyLysPheLeuArgTrpAlaGlyLysPheGlyLysAlaPheValelyGluIleMet
GlyIleGlyLysPheLeuArgMetAlaGlyLysPheGlyLysAlaPheValGlyGluIleMet
GlyIleGlyLysPheLeuPheAlaAlaGlyLysPheGlyLysAlaPheValGlyGluIleMet
GlyIleGlyLysPheLeuPheGluAlaGlyLysPheGlyLysAlaPheValGlyGluIleMet
GlyIleGlyLysPheLeuPheThrAlaGlyLysPheGlyLysAlaPheValGlyGluIleMet
GlyIleGlyLysPheLeuPheTrpAlaGlyLysPheGlyLysAlaPheValGlyGluIleMet
GlyIleGlyLysPheLeuPheMetAlaGlyLysPheGlyLysAlaPheValGlyGluIleMet
GlyIleGlyLysPheLeuGluAlaAlaGlyLysPheGlyLysAlaPheValGlyGluIleMet
GlyIleGlyLysPheLeuGluGluAlaGlyLysPheGlyLysAlaPheValGlyGluIleMet
GlyIleGlyLysPheLeuGluThrAlaGlyLysPheGlyLysAlaPheValGlyGluIleMet
GlyIleGlyLysPheLeuGluTrpAlaGlyLysPheGlyLysAlaPheValGlyGluIleMet
GlyIleGlyLysPheLeuGluMetAlaGlyLysPheGlyLysAlaPheValGlyGluIleMet
GlyIleGlyLysPheLeuMetAlaAlaGlyLysPheGlyLysAlaPheValGlyGluIleMet
GlyIleGlyLysPheLeuMetGluAlaGlyLysPheGlyLysAlaPheValGlyGluIleMet
GlyIleGlyLysPheLeuMetThrAlaGlyLysPheGlyLysAlaPheValGlyGluIleMet
GlyIleGlyLysPheLeuMetTrpAlaGlyLysPheGlyLysAlaPheValGlyGluIleMet
GlyIleGlyLysPheLeuMetMetAlaGlyLysPheGlyLysAlaPheValGlyGluIleMet
GlyIleGlyLysPheLeuGlnAlaAlaGlyLysPheGlyLysAlaPheValGlyGluIleMet
GlyIleGlyLysPheLeuGlnGluAlaGlyLysPheGlyLysAlaPheValGlyGluIleMet
GlyIleGlyLysPheLeuGlnThrAlaGlyLysPheGlyLysAlaPheValGlyGluIleMet
GlyIleGlyLysPheLeuGlnTrpAlaGlyLysPheGlyLysAlaPheValGlyGluIleMet
GlyIleGlyLysPheLeuGlnMetAlaGlyLysPheGlyLysAlaPheValGlyGluIleMet
IleGlyLysPheLeuHisSerAlaGlyLysPheGlyLysAlaPheValGlyGluIleMetLys
IleGlyLysPheLeuArgSerAlaGlyLysPheGlyLysAlaPheValGlyGluIleMetLys
IleGlyLysPheLeuLysSerAlaGlyLysPheGlyLysAlaPheValGlyGluIleMetLys
IleGlyLysPheLeuPheSerAlaGlyLysPheGlyLysAlaPheValGlyGluIleMetLys
IleGlyLysPheLeuGluSerAlaGlyLysPheGlyLysAlaPheValGlyGluIleMetLys
IleGlyLysPheLeuAspSerAlaGlyLysPheGlyLysAlaPheValGlyGluIleMetLys
IleGlyLysPheLeuMetSerAlaGlyLysPheGlyLysAlaPheValGlyGluIleMetLys
IleGlyLysPheLeuTyrSerAlaGlyLysPheGlyLysAlaPheValGlyGluIleMetLys
IleGlyLysPheLeuAlaSerAlaGlyLysPheGlyLysAlaPheValGlyGluIleMetLys
IleGlyLysPheLeuHisAlaAlaGlyLysPheGlyLysAlaPheValGlyGluIleMetLys
IleGlyLysPheLeuHisGluAlaGlyLysPheGlyLysAlaPheValGlyGluIleMetLys
IleGlyLysPheLeuHisThrAlaGlyLysPheGlyLysAlaPheValGlyGluIleMetLys
IleGlyLysPheLeuHisMetAlaGlyLysPheGlyLysAlaPheValGlyGluIleMetLys
IleGlyLysPheLeuHisTyrAlaGlyLysPheGlyLysAlaPheValGlyGluIleMetLys
IleGlyLysPheLeuHisLysAlaGlyLysPheGlyLysAlaPheValGlyGluIleMetLys
IleGlyLysPheLeuHisArgAlaGlyLysPheGlyLysAlaPheValGlyGluIleMetLys -continued IleGlyLysPheLeuHisAspAlaGlyLysPheGlyLysAlaPheValGlyGluIleMetLys
IleGlyLysPheLeuHisTrpAlaGlyLysPheGlyLysAlaPheValGlyGluIleMetLys
IleGlyLysPheLeuLysAlaAlaGlyLysPheGlyLysAlaPheValGlyGluIleMetLys
IleGlyLysPheLeuLysGluAlaGlyLysPheGlyLysAlaPheValGlyGluIleMetLys
IleGlyLysPheLeuLysThrAlaGlyLysPheGlyLysAlaPheValGlyGluIleMetLys
IleGlyLysPheLeuLysTrpAlaGlyLysPheGlyLysAlaPheValGlyGluIleMetLys
IleGlyLysPheLeuLysMetAlaGlyLysPheGlyLysAlaPheValGlyGluIleMetLys
IleGlyLysPheLeuArgAlaAlaGlyLysPheGlyLysAlaPheValGlyGluIleMetLys
IleGlyLysPheLeuArgGluAlaGlyLysPheGlyLysAlaPheValGlyGluIleMetLys
IleGlyLysPheLeuArgThrAlaGlyLysPheGlyLysAlaPheValGlyGluIleMetLys
IleGlyLysPheLeuArgTrpAlaGlyLysPheGlyLysAlaPheValGlyGluIleMetLys
IleGlyLysPheLeuArgMetAlaGlyLysPheGlyLysAlaPheValGlyGluIleMetLys
IleGlyLysPheLeuPheAlaAlaGlyLysPheGlyLysAlaPheValGlyGluIleMetLys
IleGlyLysPheLeuPheGluAlaGlyLysPheGlyLysAlaPheValGlyGluIleMetLys
IleGlyLysPheLeuPheThrAlaGlyLysPheGlyLysAlaPheValGlyGluIleMetLys
IleGlyLysPheLeuPheTrpAlaGlyLysPheGlyLysAlaPheValGlyGluIleMetLys
IleGlyLysPheLeuPheMetAlaGlyLysPheGlyLysAlaPheValGlyGluIleMetLys
IleGlyLysPheLeuGluAlaAlaGlyLysPheGlyLysAlaPheValGlyGluIleMetLys
IleGlyLysPheLeuGluGluAlaGlyLysPheGlyLysAlaPheValGlyGluIleMetLys
IleGlyLysPheLeuGluThrAlaGlyLysPheGlyLysAlaPheValGlyGluIleMetLys
IleGlyLysPheLeuGluTrpAlaGlyLysPheGlyLysAlaPheValGlyGluIleMetLys
IleGlyLysPheLeuGluMetAlaGlyLysPheGlyLysAlaPheValGlyGluIleMetLys
IleGlyLysPheLeuMetAlaAlaGlyLysPheGlyLysAlaPheValGlyGluIleMetLys
IleGlyLysPheLeuMetGluAlaGlyLysPheGlyLysAlaPheValGlyGluIleMetLys
IleGlyLysPheLeuMetThrAlaGlyLysPheGlyLysAlaPheValGlyGluIleMetLys
IleGlyLysPheLeuMetTrpAlaGlyLysPheGlyLysAlaPheValGlyGluIleMetLys
IleGlyLysPheLeuMetMetAlaGlyLysPheGlyLysAlaPheValGlyGluIleMetLys
IleGlyLysPheLeuGlnAlaAlaGlyLysPheGlyLysAlaPheValGlyGluIleMetLys
IleGlyLysPheLeuGlnGluAlaGlyLysPheGlyLysAlaPheValGlyGluIleMetLys
IleGlyLysPheLeuGlnThrAlaGlyLysPheGlyLysAlaPheValGlyGluIleMetLys
IleGlyLysPheLeuGlnTrpAlaGlyLysPheGlyLysAlaPheValGlyGluIleMetLys
IleGlyLysPheLeuGlnMetAlaGlyLysPheGlyLysAlaPheValGlyGluIleMetLys
MetGlyIleGlyLysPheLeuHisSerAlaGlyLysPheGlyLysAlaPheValGlyGluIleMetLysSer
MetGlyIleGlyLysPheLeuArgSerAlaGlyLysPheGlyLysAlaPheValGlyGluIleMetLysSer
MetGlyIleGlyLysPheLeuLysSerAlaGlyLysPheGlyLysAlaPheValGlyGluIleMetLysSer
MetGlyIleGlyLysPheLeuPheSerAlaGlyLysPheGlyLysAlaPheValGlyGluIleMetLysSer
MetGlyIleGlyLysPheLeuGluSerAlaGlyLysPheGlyLysAlaPheValGlyGluIleMetLysSer
MetGlyIleGlyLysPheLeuAspSerAlaGlyLysPheGlyLysAlaPheValGlyGluIleMetLysSer
MetGlyIleGlyLysPheLeuMetSerAlaGlyLysPheGlyLysAlaPheValGlyGluIleMetLysSer
MetGlyIleGlyLysPheLeuTyrSerAlaGlyLysPheGlyLysAlaPheValGlyGluIleMetLysSer
MetGlyIleGlyLysPheLeuAlaSerAlaGlyLysPheGlyLysAlaPheValGlyGluIleMetLysSer
MetGlyIleGlyLysPheLeuHisAlaAlaGlyLysPheGlyLysAlaPheValGlyGluIleMetLysSer
MetGlyIleGlyLysPheLeuHisGluAlaGlyLysPheGlyLysAlaPheValGlyGluIleMetLysSer
MetGlyIleGlyLysPheLeuHisThrAlaGlyLysPheGlyLysAlaPheValGlyGluIleMetLysSer
MetGlyIleGlyLysPheLeuArgGluAlaGlyLysPheGlyLysAlaPheValGlyGluIleMetLysSer
MetGlyIleGlyLysPheLeuLysGluAlaGlyLysPheGlyLysAlaPheValGlyGluIleMetLysSer
MetIleGlyLysPheLeuHisSerAlaGlyLysPheGlyLysAlaPheValGlyGluIleMetLysSer
MetIleGlyLysPheLeuArgSerAlaGlyLysPheGlyLysAlaPheValGlyGluIleMetLysSer
MetIleGlyLysPheLeuLysSerAlaGlyLysPheGlyLysAlaPheValGlyGluIleMetLysSer
MetIleGlyLysPheLeuPheSerAlaGlyLysPheGlyLysAlaPheValGlyGluIleMetLysSer
MetIleGlyLysPheLeuGluSerAlaGlyLysPheGlyLysAlaPheValGlyGluIleMetLysSer
MetIleGlyLysPheLeuAspSerAlaGlyLysPheGlyLysAlaPheValGlyGluIleMetLysSer
MetIleGlyLysPheLeuMetSerAlaGlyLysPheGlyLysAlaPheValGlyGluIleMetLysSer
MetIleGlyLysPheLeuTyrSerAlaGlyLysPheGlyLysAlaPheValGlyGluIleMetLysSer
HatIleGlyLysPheLeuHisAlaAlaGlyLysPheGlyLysAlaPheValGlyGluIleMetLysSer
MetIleGlyLysPheLeuHisAlaAlaGlyLysPheIleLysAlaPheValGlyGluIleMetLysSer
MetIleGlyLysPheLeuHisGluAlaGlyLysPheGlyLysAlaPheValGlyGluIleMetLysSer
MetIleGlyLysPheLeuHisThrAlaGlyLysPheGlyLysAlaPheValGlyGluIleMetLysSer
HatIleGlyLysPheLeuArgGluAlaGlyLysPheGlyLysAlaPheValGlyGluIleMetLysSer
MetIleGlyLysPheLeuLysGluAlaGlyLysPheGlyLysAlaPheValGlyGluIleMetLysSer
MetGlyIleGlyLysPheLeuHisSerAlaGlyLysPheAlaLysAlaPheValGlyGluIleMetLysSer
MetGlyIleGlyLysPheLeuArgSerAlaGlyLysPheAlaLysAlaPheValGlyGluIleMetLysSer
MetGlyIleGlyLysPheLeuLysSerAlaGlyLysPheAlaLysAlaPheValGlyGluIleMetLysSer
MetGlyIleGlyLysPheLeuPheSerAlaGlyLysPheAlaLysAlaPheValGlyGluIleMetLysSer
MetGlyIleGlyLysPheLeuGluSerAlaGlyLysPheAlaLysAlaPheValGlyGluIleMetLysSer
MetGlyIleGlyLysPheLeuAspSerAlaGlyLysPheAlaLysAlaPheValGlyGluIleMetLysSer
MetGlyIleGlyLysPheLeuMetSerAlaGlyLysPheAlaLysAlaPheValGlyGluIleMetLysSer
MetGlyIleGlyLysPheLeuTyrSerAlaGlyLysPheAlaLysAlaPheValGlyGluIleMetLysSer
MetGlyIleGlyLysPheLeuAlaSerAlaGlyLysPheAlaLysAlaPheValGlyGluIleMetLysSer
MetGlyIleGlyLysPheLeuHisAlaAlaGlyLysPheAlaLysAlaPheValGlyGluIleMetLysSer
MetGlyIleGlyLysPheLeuHisGluAlaGlyLysPheAlaLysAlaPheValGlyGluIleMetLysSer
MetGlyIleGlyLysPheLeuHisThrAlaGlyLysPheAlaLysAlaPheValGlyGluIleMetLysSer
MetGlyIleGlyLysPheLeuArgGluAlaGlyLysPheAlaLysAlaPheValGlyGluIleMetLysSer
MetGlyIleGlyLysPheLeuLysGluAlaGlyLysPheAlaLysAlaPheValGlyGluIleMetLysSer
MetIleGlyLysPheLeuHisSerAlaGlyLysPheAlaLysAlaPheValGlyGluIleMetLysSer
MetIleGlyLysPheLeuArgSerAlaGlyLysPheAlaLysAlaPheValGlyGluIleMetLysSer
MetIleGlyLysPheLeuLysSerAlaGlyLysPheAlaLysAlaPheValGlyGluIleMetLysSer
MetIleGlyLysPheLeuPheSerAlaGlyLysPheAlaLysAlaPheValGlyGluIleMetLysSer
MetIleGlyLysPheLeuGluSerAlaGlyLysPheAlaLysAlaPheValGlyGluIleMetLysSer
MetIleGlyLysPheLeuAspSerAlaGlyLysPheAlaLysAlaPheValGlyGluIleMetLysSer
MetIleGlyLysPheLeuMetSerAlaGlyLysPheAlaLysAlaPheValGlyGluIleMetLysSer
MetIleGlyLysPheLeuTyrSerAlaGlyLysPheAlaLysAlaPheValGlyGluIleMetLysSer
MetIleGlyLysPheLeuHisAlaAlaGlyLysPheAlaLysAlaPheValGlyGluIleMetLysSer -continued MetIleGlyLysPheLeuHisAlaAlaGlyLysPheIleLysAlaPheValGlyGluIleMetLysSer
MetIleGlyLysPheLeuHisGluAlaGlyLysPheAlaLysAlaPheValGlyGluIleMetLysSer
MetIleGlyLysPheLeuHisThrAlaGlyLysPheAlaLysAlaPheValGlyGluIleMetLysSer
MetIleGlyLysPheLeuArgGluAlaGlyLysPheAlaLysAlaPheValGlyGluIleMetLysSer
MetIleGlyLysPheLeuLysGluAlaGlyLysPheAlaLysAlaPheValGlyGluIleMetLysSer
GlyIleGlyLysPheLeuHisSerAlaGlyLysPheAlaLysAlaPheValGlyGluIleMetLysSer
GlyIleGlyLysPheLeuArgSerAlaGlyLysPheAlaLysAlaPheValGlyGluIleMetLysSer
GlyIleGlyLysPheLeuLysSerAlaGlyLysPheAlaLysAlaPheValGlyGluIleMetLysSer
GlyIleGlyLysPheLeuPheSerAlaGlyLysPheAlaLysAlaPheValGlyGluIleMetLysSer
GlyIleGlyLysPheLeuGluSerAlaGlyLysPheAlaLysAlaPheValGlyGluIleMetLysSer
GlyIleGlyLysPheLeuAspSerAlaGlyLysPheAlaLysAlaPheValGlyGluIleMetLysSer
GlyIleGlyLysPheLeuMetSerAlaGlyLysPheAlaLysAlaPheValGlyGluIleMetLysSer
GlyIleGlyLysPheLeuTyrSerAlaGlyLysPheAlaLysAlaPheValGlyGluIleMetLysSer
GlyIleGlyLysPheLeuAlaSerAlaGlyLysPheAlaLysAlaPheValGlyGluIleMetLysSer
GlyIleGlyLysPheLeuHisAlaAlaGlyLysPheAlaLysAlaPheValGlyGluIleMetLysSer
GlyIleGlyLysPheLeuHisGluAlaGlyLysPheAlaLysAlaPheValGlyGluIleMetLysSer
GlyIleGlyLysPheLeuHisThrAlaGlyLysPheAlaLysAlaPheValGlyGluIleMetLysSer
GlyIleGlyLysPheLeuAsnGluAlaGlyLysPheAlaLysAlaPheValGlyGluIleMetLysSer
GlyIleGlyLysPheLeuLysGluAlaGlyLysPheAlaLysAlaPheValGlyGluIleMetLysSer
IleGlyLysPheLeuHisSerAlaGlyLysPheAlaLysAlaPheValGlyGluIleMetLysSer
IleGlyLysPheLeuArgSerAlaGlyLysPheAlaLysAlaPheValGlyGluIleMetLysSer
IleGlyLysPheLeuLysSerAlaGlyLysPheAlaLysAlaPheValGlyGluIleMetLysSer
IleGlyLysPheLeuPheSerAlaGlyLysPheAlaLysAlaPheValGlyGluIleMetLysSer
IleGlyLysPheLeuGluSerAlaGlyLysPheAlaLysAlaPheValGlyGluIleMetLysSer
IleGlyLysPheLeuAspSerAlaGlyLysPheAlaLysAlaPheValGlyGluIleMetLysSer
IleGlyLysPheLeuMetSerAlaGlyLysPheAlaLysAlaPheValGlyGluIleMetLysSer
IleGlyLysPheLeuTyrSerAlaGlyLysPheAlaLysAlaPheValGlyGluIleMetLysSer
IleGlyLysPheLeuAlaSerAlaGlyLysPheAlaLysAlaPheValGlyGluIleMetLysSer
IleGlyLysPheLeuHisAlaAlaGlyLysPheAlaLysAlaPheValGlyGluIleMetLysSer
IleGlyLysPheLeuHisAlaAlaGlyLysPheIleLysAlaPheValGlyGluIleMetLysSer
IleGlyLysPheLeuHisGluAlaGlyLysPheAlaLysAlaPheValGlyGluIleMetLysSer
IleGlyLysPheLeuHisThrAlaGlyLysPheAlaLysAlaPheValGlyGluIleMetLysSer
IleGlyLysPheLeuAsnGluAlaGlyLysPheAlaLysAlaPheValGlyGluIleMetLysSer
IleGlyLysPheLeuLysGluAlaGlyLysPheAlaLysAlaPheValGlyGluIleMetLysSer
GlyIleGlyLysPheLeuHisSerAlaLysLysPheGlyLysAlaPheValGlyGluIleMetLysSer
GlyIleGlyLysPheLeuHisSerAlaLysLysPheIleLysAlaPheValGlyGluIleMetLysSer
GlyIleGlyLysPheLeuArgSerAlaLysLysPheGlyLysAlaPheValGlyGluIleMetLysSer
GlyIleGlyLysPheLeuLysSerAlaLysLysPheGlyLysAlaPheValGlyGluIleMetLysSer
GlyIleGlyLysPheLeuPheSerAlaLysLysPheGlyLysAlaPheValGlyGluIleMetLysSer
GlyIleGlyLysPheLeuGluSerAlaLysLysPheGlyLysAlaPheValGlyGluIleMetLysSer
GlyIleGlyLysPheLeuAspSerAlaLysLysPheGlyLysAlaPheValGlyGluIleMetLysSer
GlyIleGlyLysPheLeuMetSerAlaLysLysPheGlyLysAlaPheValGlyGluIleMetLysSer
GlyIleGlyLysPheLeuTyrSerAlaLysLysPheGlyLysAlaPheValGlyGluIleMetLysSer
GlyIleGlyLysPheLeuAlaSerAlaLysLysPheGlyLysAlaPheValGlyGluIleMetLysSer
GlyIleGlyLysPheLeuHisAlaAlaLysLysPheGlyLysAlaPheValGlyGluIleMetLysSer
GlyIleGlyLysPheLeuHisGluAlaLysLysPheGlyLysAlaPheValGlyGluIleMetLysSer
GlyIleGlyLysPheLeuHisThrAlaLysLysPheGlyLysAlaPheValGlyGluIleMetLysSer
GlyIleGlyLysPheLeuHisMetAlaLysLysPheGlyLysAlaPheValGlyGluIleMetLysSer
GlyIleGlyLysPheLeuHisTyrAlaLysLysPheGlyLysAlaPheValGlyGluIleMetLysSer
GlyIleGlyLysPheLeuHisLysAlaLysLysPheGlyLysAlaPheValGlyGluIleMetLysSer
GlyIleGlyLysPheLeuHisArgAlaLysLysPheGlyLysAlaPheValGlyGluIleMetLysSer
GlyIleGlyLysPheLeuHisAspAlaLysLysPheGlyLysAlaPheValGlyGluIleMetLysSer
GlyIleGlyLysPheLeuHisTrpAlaLysLysPheGlyLysAlaPheValGlyGluIleMetLysSer
GlyIleGlyLysPheLeuLysAlaAlaLysLysPheGlyLysAlaPheValGlyGluIleMetLysSer
GlyIleGlyLysPheLeuLysGluAlaLysLysPheGlyLysAlaPheValGlyGluIleMetLysSer
GlyIleGlyLysPheLeuLysThrAlaLysLysPheGlyLysAlaPheValGlyGluIleMetLysSer
GlyIleGlyLysPheLeuLysTrpAlaLysLysPheGlyLysAlaPheValGlyGluIleMetLysSer
GlyIleGlyLysPheLeuLysMetAlaLysLysPheGlyLysAlaPheValGlyGluIleMetLysSer
GlyIleGlyLysPheLeuArgAlaAlaLysLysPheGlyLysAlaPheValGlyGluIleMetLysSer
GlyIleGlyLysPheLeuArgGluAlaLysLysPheGlyLysAlaPheValGlyGluIleMetLysSer
GlyIleGlyLysPheLeuArgThrAlaLysLysPheGlyLysAlaPheValGlyGluIleMetLysSer
GlyIleGlyLysPheLeuArgTrpAlaLysLysPheGlyLysAlaPheValGlyGluIleMetLysSer
GlyIleGlyLysPheLeuArgMetAlaLysLysPheGlyLysAlaPheValGlyGluIleMetLysSer
IleGlyLysPheLeuHisSerAlaLysLysPheGlyLysAlaPheValGlyGluIleMetLysSer
IleGlyLysPheLeuArgSerAlaLysLysPheGlyLysAlaPheValGlyGluIleMetLysSer
IleGlyLysPheLeuLysSerAlaLysLysPheGlyLysAlaPheValGlyGluIleMetLysSer
IleGlyLysPheLeuPheSerAlaLysLysPheGlyLysAlaPheValGlyGluIleMetLysSer
IleGlyLysPheLeuGluSerAlaLysLysPheGlyLysAlaPheValGlyGluIleMetLysSer
IleGlyLysPheLeuAspSerAlaLysLysPheGlyLysAlaPheValGlyGluIleMetLysSer
IleGlyLysPheLeuHisAlaAlaLysLysPheGlyLysAlaPheValGlyGluIleMetLysSer
IleGlyLysPheLeuHisAlaAlaLysLysPheIleLysAlaPheValGlyGluIleMetLysSer
IleGlyLysPheLeuHisGluAlaLysLysPheGlyLysAlaPheValGlyGluIleMetLysSer
IleGlyLysPheLeuHisThrAlaLysLysPheGlyLysAlaPheValGlyGluIleMetLysSer
IleGlyLysPheLeuArgGluAlaLysLysPheGlyLysAlaPheValGlyGluIleMetLysSer
IleGlyLysPheLeuLysGluAlaLysLysPheGlyLysAlaPheValGlyGluIleMetLysSer
GlyIleGlyLysPheLeuHisSerAlaLysLysPheGlyLysAlaPheValGlyGluIleMet
GlyIleGlyLysPheLeuArgSerAlaLysLysPheGlyLysAlaPheValGlyGluIleMet
GlyIleGlyLysPheLeuLysSerAlaLysLysPheGlyLysAlaPheValGlyGluIleMet
GlyIleGlyLysPheLeuPheSerAlaLysLysPheGlyLysAlaPheValGlyGluIleMet
GlyIleGlyLysPheLeuGluSerAlaLysLysPheGlyLysAlaPheValGlyGluIleMet
GlyIleGlyLysPheLeuAspSerAlaLysLysPheGlyLysAlaPheValGlyGluIluMet
GlyIleGlyLysPheLeuMetSerAlaLysLysPheGlyLysAlaPheValGlyGluIleMet
GlyIleGlyLysPheLeuTyrSerAlaLysLysPheGlyLysAlaPheValGlyGluIleMet -continued GlyIleGlyLysPheLeuAlaSerAlaLysLysPheGlyLysAlaPheValGlyGluIleMet
GlyIleGlyLysPheLeuHisAlaAlaLysLysPheGlyLysAlaPheValGlyGluIleMet
GlyIleGlyLysPheLeuHisGluAlaLysLysPheGlyLysAlaPheValGlyGluIleMet
GlyIleGlyLysPheLeuHisThrAlaLysLysPheGlyLysAlaPheValGlyGluIleMet
GlyIleGlyLysPheLeuHisMetAlaLysLysPheGlyLysAlaPheValGlyGluIleMet
GlyIleGlyLysPheLeuHisTyrAlaLysLysPheGlyLysAlaPheValGlyGluIleMet
GlyIleGlyLysPheLeuHisLysAlaLysLysPheGlyLysAlaPheValGlyGluIleMet
GlyIleGlyLysPheLeuHisArgAlaLysLysPheGlyLysAlaPheValGlyGluIleMet
GlyIleGlyLysPheLeuHisAspAlaLysLysPheGlyLysAlaPheValGlyGluIleMet
GlyIleGlyLysPheLeuHisTrpAlaLysLysPheGlyLysAlaPheValGlyGluIleMet
GlyIleGlyLysPheLeuLysAlaAlaLysLysPheGlyLysAlaPheValGlyGluIleMet
GlyIleGlyLysPheLeuLysGluAlaLysLysPheGlyLysAlaPheValGlyGluIleMet
GlyIleGlyLysPheLeuLysThrAlaLysLysPheGlyLysAlaPheValGlyGluIleMet
GlyIleGlyLysPheLeuLysTrpAlaLysLysPheGlyLysAlaPheValGlyGluIleMet
GlyIleGlyLysPheLeuLysMetAlaLysLysPheGlyLysAlaPheValGlyGluIleMet
GlyIleGlyLysPheLeuArgAlaAlaLysLysPheGlyLysAlaPheValGlyGluIleMet
GlyIleGlyLysPheLeuArgGluAlaLysLysPheGlyLysAlaPheValGlyGluIleMet
GlyIleGlyLysPheLeuArgThrAlaLysLysPheGlyLysAlaPheValGlyGluIleMet
GlyIleGlyLysPheLeuArgTrpAlaLysLysPheGlyLysAlaPheValGlyGluIleMet
GlyIleGlyLysPheLeuArgMetAlaLysLysPheGlyLysAlaPheValGlyGluIleMet
MetGlyIleGlyLysPheLeuHisSerAlaLysLysPheGlyLysAlaPheValGlyGluIleMetLysSer
MetGlyIleGlyLysPheLeuArgSerAlaLysLysPheGlyLysAlaPheValGlyGluIleMetLysSer
MetGlyIleGlyLysPheLeuLysSerAlaLysLysPheGlyLysAlaPheValGlyGluIleMetLysSer
MetGlyIleGlyLysPheLeuPheSerAlaLysLysPheGlyLysAlaPheValGlyGluIleMetLysSer
MetGlyIleGlyLysPheLeuGluSerAlaLysLysPheGlyLysAlaPheValGlyGluIleMetLysSer
MetGlyIleGlyLysPheLeuAspSerAlaLysLysPheGlyLysAlaPheValGlyGluIleMetLysSer
MetGlyIleGlyLysPheLeuMetSerAlaLysLysPheGlyLysAlaPheValGlyGluIleMetLysSer
MetGlyIleGlyLysPheLeuTyrSerAlaLysLysPheGlyLysAlaPheValGlyGluIleMetLysSer
MetGlyIleGlyLysPheLeuAlaSerAlaLysLysPheGlyLysAlaPheValGlyGluIleMetLysSer
MetGlyIleGlyLysPheLeuHisAlaAlaLysLysPheGlyLysAlaPheValGlyGluIleMetLysSer
MetGlyIleGlyLysPheLeuHisGluAlaLysLysPheGlyLysAlaPheValGlyGluIleMetLysSer
MetGlyIleGlyLysPheLeuHisThrAlaLysLysPheGlyLysAlaPheValGlyGluIleMetLysSer
MetGlyIleGlyLysPheLeuArgGluAlaLysLysPheGlyLysAlaPheValGlyGluIleMetLysSer
MetGlyIleGlyLysPheLeuLysGluAlaLysLysPheGlyLysAlaPheValGlyGluIleMetLysSer
MetIleGlyLysPheLeuHisSerAlaLysLysPheGlyLysAlaPheValGlyGluIleMetLysSer
MetIleGlyLysPheLeuArgSerAlaLysLysPheGlyLysAlaPheValGlyGluIleMetLysSer
MetIleGlyLysPheLeuLysSerAlaLysLysPheGlyLysAlaPheValGlyGluIleMetLysSer
MetIleGlyLysPheLeuPheSerAlaLysLysPheGlyLysAlaPheValGlyGluIleMetLysSer
MetIleGlyLysPheLeuGluSerAlaLysLysPheGlyLysAlaPheValGlyGluIleMetLysSer
MetIleGlyLysPheLeuAspSerAlaLysLysPheGlyLysAlaPheValGlyGluIleMetLysSer
MetIleGlyLysPheLeuMetSerAlaLysLysPheGlyLysAlaPheValGlyGluIleMetLysSer
MetIleGlyLysPheLeuTyrSerAlaLysLysPheGlyLysAlaPheValGlyGluIleMetLysSer
MetIleGlyLysPheLeuHisAlaAlaLysLysPheGlyLysAlaPheValGlyGluIleMetLysSer
MetIleGlyLysPheLeuHisAlaAlaLysLysPheIleLysAlaPheValGlyGluIleMetLysSer
MetIleGlyLysPheLeuHisGluAlaLysLysPheGlyLysAlaPheValGlyGluIleMetLysSer
MetIleGlyLysPheLeuHisThrAlaLysLysPheGlyLysAlaPheValGlyGluIleMetLysSer
MetIleGlyLysPheLeuArgGluAlaLysLysPheGlyLysAlaPheValGlyGluIleMetLysSer
MetIleGlyLysPheLeuLysGluAlaLysLysPheGlyLysAlaPheValGlyGluIleMetLysSer
MetGlyIleGlyLysPheLeuHisSerAlaLysLysPheAlaLysAlaPheValGlyGluIleMetLysSer
MetGlyIleGlyLysPheLeuArgSerAlaLysLysPheAlaLysAlaPheValGlyGluIleMetLysSer
MetGlyIleGlyLysPheLeuLysSerAlaLysLysPheAlaLysAlaPheValGlyGluIleMetLysSer
MetGlyIleGlyLysPheLeuPheSerAlaLysLysPheAlaLysAlaPheValGlyGluIleMetLysSer
MetGlyIleGlyLysPheLeuGluSerAlaLysLysPheAlaLysAlaPheValGlyGluIleMetLysSer
MetGlyIleGlyLysPheLeuAspSerAlaLysLysPheAlaLysAlaPheValGlyGluIleMetLysSer
MetGlyIleGlyLysPheLeuMetSerAlaLysLysPheAlaLysAlaPheValGlyGluIleMetLysSer
MetGlyIleGlyLysPheLeuTyrSerAlaLysLysPheAlaLysAlaPheValGlyGluIleMetLysSer
MetGlyIleGlyLysPheLeuAlaSerAlaLysLysPheAlaLysAlaPheValGlyGluIleMetLysSer
MetGlyIleGlyLysPheLeuHisAlaAlaLysLysPheAlaLysAlaPheValGlyGluIleMetLysSer
MetGlyIleGlyLysPheLeuHisGluAlaLysLysPheAlaLysAlaPheValGlyGluIleMetLysSer
MetGlyIleGlyLysPheLeuHisThrAlaLysLysPheAlaLysAlaPheValGlyGluIleMetLysSer
MetGlyIleGlyLysPheLeuArgGluAlaLysLysPheAlaLysAlaPheValGlyGluIleMetLysSer
MetGlyIleGlyLysPheLeuLysGluAlaLysLysPheAlaLysAlaPheValGlyGluIleMetLysSer
MetIleGlyLysPheLeuHisSerAlaLysLysPheAlaLysAlaPheValGlyGluIleMetLysSer
MetIleGlyLysPheLeuArgSerAlaLysLysPheAlaLysAlaPheValGlyGluIleMetLysSer
MetIleGlyLysPheLeuLysSerAlaLysLysPheAlaLysAlaPheValGlyGluIleMetLysSer
MetIleGlyLysPheLeuPheSerAlaLysLysPheAlaLysAlaPheValGlyGluIleMetLysSer
MetIleGlyLysPheLeuGluSerAlaLysLysPheAlaLysAlaPheValGlyGluIleMetLysSer
MetIleGlyLysPheLeuAspSerAlaLysLysPheAlaLysAlaPheValGlyGluIleMetLysSer
MetIleGlyLysPheLeuMetSerAlaLysLysPheAlaLysAlaPheValGlyGluIleMetLysSer
MetIleGlyLysPheLeuTyrSerAlaLysLysPheAlaLysAlaPheValGlyGluIleMetLysSer
MetIleGlyLysPheLeuHisAlaAlaLysLysPheAlaLysAlaPheValGlyGluIleMetLysSer
MetIleGlyLysPheLeuHisAlaAlaLysLysPheIleLysAlaPheValGlyGluIleMetLysSer
MetIleGlyLysPheLeuHisGluAlaLysLysPheAlaLysAlaPheValGlyGluIleMetLysSer
MetIleGlyLysPheLeuHisThrAlaLysLysPheAlaLysAlaPheValGlyGluIleMetLysSer
MetIleGlyLysPheLeuArgGluAlaLysLysPheAlaLysAlaPheValGlyGluIleMetLysSer
MetIleGlyLysPheLeuLysGluAlaLysLysPheAlaLysAlaPheValGlyGluIleMetLysSer
GlyIleGlyLysPheLeuHisSerAlaLysLysPheAlaLysAlaPheValGlyGluIleMetLysSer
GlyIleGlyLysPheLeuArgSerAlaLysLysPheAlaLysAlaPheValGlyGluIleMetLysSer
GlyIleGlyLysPheLeuLysSerAlaLysLysPheAlaLysAlaPheValGlyGluIleMetLysSer
GlyIleGlyLysPheLeuPheSerAlaLysLysPheAlaLysAlaPheValGlyGluIleMetLysSer
GlyIleGlyLysPheLeuGluSerAlaLysLysPheAlaLysAlaPheValGlyGluIleMetLysSer
GlyIleGlyLysPheLeuAspSerAlaLysLysPheAlaLysAlaPheValGlyGluIleMetLysSer
GlyIleGlyLysPheLeuMetSerAlaLysLysPheAlaLysAlaPheValGlyGluIleMetLysSer -continued GlyIleGlyLysPheLeuTyrSerAlaLysLysPheAlaLysAlaPheValGlyGluIleMetLysSer
GlyIleGlyLysPheLeuAlaSerAlaLysLysPheAlaLysAlaPheValGlyGluIleMetLysSer
GlyIleGlyLysPheLeuHisAlaAlaLysLysPheAlaLysAlaPheValGlyGluIleMetLysSer
GlyIleGlyLysPheLeuHisGluAlaLysLysPheAlaLysAlaPheValGlyGluIleMetLysSer
GlyIleGlyLysPheLeuHisThrAlaLysLysPheAlaLysAlaPheValGlyGluIleMetLysSer
GlyIleGlyLysPheLeuArgGluAlaLysLysPheAlaLysAlaPheValGlyGluIleMetLysSer
GlyIleGlyLysPheLeuLysGluAlaLysLysPheAlaLysAlaPheValGlyGluIleMetLysSer
IleGlyLysPheLeuHisSerAlaLysLysPheAlaLysAlaPheValGlyGluIleMetLysSer
IleGlyLysPheLeuArgSerAlaLysLysPheAlaLysAlaPheValGlyGluIleMetLysSer
IleGlyLysPheLeuLysSerAlaLysLysPheAlaLysAlaPheValGlyGluIleMetLysSer
IleGlyLysPheLeuPheSerAlaLysLysPheAlaLysAlaPheValGlyGluIleMetLysSer
IleGlyLysPheLeuGluSerAlaLysLysPheAlaLysAlaPheValGlyGluIleMetLysSer
IleGlyLysPheLeuAspSerAlaLysLysPheAlaLysAlaPheValGlyGluIleMetLysSer
IleGlyLysPheLeuMetSerAlaLysLysPheAlaLysAlaPheValGlyGluIleMetLysSer
IleGlyLysPheLeuTyrSerAlaLysLysPheAlaLysAlaPheValGlyGluIleMetLysSer
IleGlyLysPheLeuHisAlaAlaLysLysPheAlaLysAlaPheValGlyGluIleMetLysSer
IleGlyLysPheLeuHisAlaAlaLysLysPheIleLysAlaPheValGlyGluIleMetLysSer
IleGlyLysPheLeuHisGluAlaLysLysPheAlaLysAlaPheValGlyGluIleMetLysSer
IleGlyLysPheLeuHisGluAlaLysLysPheAlaLysAlaPheValGlyGluIleMetLysSer
IleGlyLysPheLeuArgGluAlaLysLysPheAlaLysAlaPheValGlyGluIleMetLysSer
IleGlyLysPheLeuLysGluAlaLysLysPheAlaLysAlaPheValGlyGluIleMetLysSer
GlyIleGlyLysPheLeuArgSerAlaLysLysPheGlyLysAlaPheValGlyGluIleMetAsnSer
GlyIleGlyLysPheLeuLysSerAlaLysLysPheGlyLysAlaPheValGlyGluIleMetAsnSer
GlyIleGlyLysPheLeuPheSerAlaLysLysPheGlyLysAlaPheValGlyGluIleMetAsnSer
GlyIleGlyLysPheLeuGluSerAlaLysLysPheGlyLysAlaPheValGlyGluIleMetAsnSer
GlyIleGlyLysPheLeuAspSerAlaLysLysPheGlyLysAlaPheValGlyGluIleMetAsnSer
GlyIleGlyLysPheLeuMetSerAlaLysLysPheGlyLysAlaPheValGlyGluIleMetAsnSer
GlyIleGlyLysPheLeuTyrSerAlaLysLysPheGlyLysAlaPheValGlyGluIleMetAsnSer
GlyIleGlyLysPheLeuHisGluAlaLysLysPheGlyLysAlaPheValGlyGluIleMetAsnSer
GlyIleGlyLysPheLeuHisThrAlaLysLysPheGlyLysAlaPheValGlyGluIleMetAsnSer
GlyIleGlyLysPheLeuHisMetAlaLysLysPheGlyLysAlaPheValGlyGluIleMetAsnSer
GlyIleGlyLysPheLeuHisTyrAlaLysLysPheGlyLysAlaPheValGlyGluIleMetAsnSer
GlyIleGlyLysPheLeuHisLysAlaLysLysPheGlyLysAlaPheValGlyGluIleMetAsnSer
GlyIleGlyLysPheLeuHisArgAlaLysLysPheGlyLysAlaPheValGlyGluIleMetAsnSer
GlyIleGlyLysPheLeuHisAspAlaLysLysPheGlyLysAlaPheValGlyGluIleMetAsnSer
GlyIleGlyLysPheLeuHisTrpAlaLysLysPheGlyLysAlaPheValGlyGluIleMetAsnSer
GlyIleGlyLysPheLeuLysAlaAlaLysLysPheGlyLysAlaPheValGlyGluIleMetAsnSer
GlyIleGlyLysPheLeuLysGluAlaLysLysPheGlyLysAlaPheValGlyGluIleMetAsnSer
GlyIleGlyLysPheLeuLysThrAlaLysLysPheGlyLysAlaPheValGlyGluIleMetAsnSer
GlyIleGlyLysPheLeuLysTrpAlaLysLysPheGlyLysAlaPheValGlyGluIleMetAsnSer
GlyIleGlyLysPheLeuLysMetAlaLysLysPheGlyLysAlaPheValGlyGluIleMetAsnSer
GlyIleGlyLysPheLeuArgAlaAlaLysLysPheGlyLysAlaPheValGlyGluIleMetAsnSer
GlyIleGlyLysPheLeuArgGluAlaLysLysPheGlyLysAlaPheValGlyGluIleMetAsnSer
GlyIleGlyLysPheLeuArgThrAlaLysLysPheGlyLysAlaPheValGlyGluIleMetAsnSer
GlyIleGlyLysPheLeuArgTrpAlaLysLysPheGlyLysAlaPheValGlyGluIleMetAsnSer
GlyIleGlyLysPheLeuArgMetAlaLysLysPheGlyLysAlaPheValGlyGluIleMetAsnSer
IleGlyLysPheLeuArgSerAlaLysLysPheGlyLysAlaPheValGlyGluIleMetAsnSer
IleGlyLysPheLeuLysSerAlaLysLysPheGlyLysAlaPheValGlyGluIleMetAsnSer
IleGlyLysPheLeuPheSerAlaLysLysPheGlyLysAlaPheValGlyGluIleMetAsnSer
IleGlyLysPheLeuGluSerAlaLysLysPheGlyLysAlaPheValGlyGluIleMetAsnSer
IleGlyLysPheLeuAspSerAlaLysLysPheGlyLysAlaPheValGlyGluIleMetAsnSer
IleGlyLysPheLeuHisAlaAlaLysLysPheGlyLysAlaPheValGlyGluIleMetAsnSer
IleGlyLysPheLeuHisAlaAlaLysLysPheIleLysAlaPheValGlyGluIleMetAsnSer
IleGlyLysPheLeuHisGluAlaLysLysPheGlyLysAlaPheValGlyGluIleMetAsnSer
IleGlyLysPheLeuHisThrAlaLysLysPheGlyLysAlaPheValGlyGluIleMetAsnSer
IleGlyLysPheLeuArgGluAlaLysLysPheGlyLysAlaPheValGlyGluIleMetAsnSer
IleGlyLysPheLeuLysGluAlaLysLysPheGlyLysAlaPheValGlyGluIleMetAsnSer
MetGlyIleGlyLysPheLeuHisSerAlaLysLysPheGlyLysAlaPheValGlyGluIleMetAsnSer
MetGlyIleGlyLysPheLeuArgSerAlaLysLysPheGlyLysAlaPheValGlyGluIleMetAsnSer
MetGlyIleGlyLysPheLeuLysSerAlaLysLysPheGlyLysAlaPheValGlyGluIleMetAsnSer
MetGlyIleGlyLysPheLeuPheSerAlaLysLysPheGlyLysAlaPheValGlyGluIleMetAsnSer
MetGlyIleGlyLysPheLeuGluSerAlaLysLysPheGlyLysAlaPheValGlyGluIleMetAsnSer
MetGlyIleGlyLysPheLeuAspSerAlaLysLysPheGlyLysAlaPheValGlyGluIleMetAsnSer
MetGlyIleGlyLysPheLeuMetSerAlaLysLysPheGlyLysAlaPheValGlyGluIleMetAsnSer
MetGlyIleGlyLysPheLeuTyrSerAlaLysLysPheGlyLysAlaPheValGlyGluIleMetAsnSer
MetGlyIleGlyLysPheLeuAlaSerAlaLysLysPheGlyLysAlaPheValGlyGluIleMetAsnSer
MetGlyIleGlyLysPheLeuHisAlaAlaLysLysPheGlyLysAlaPheValGlyGluIleMetAsnSer
MetGlyIleGlyLysPheLeuHisGluAlaLysLysPheGlyLysAlaPheValGlyGluIleMetAsnSer
MetGlyIleGlyLysPheLeuHisThrAlaLysLysPheGlyLysAlaPheValGlyGluIleMetAsnSer
MetGlyIleGlyLysPheLeuArgGluAlaLysLysPheGlyLysAlaPheValGlyGluIleMetAsnSer
MetGlyIleGlyLysPheLeuLysGluAlaLysLysPheGlyLysAlaPheValGlyGluIleMetAsnSer
MetIleGlyLysPheLeuHisSerAlaLysLysPheGlyLysAlaPheValGlyGluIleMetAsnSer
MetIleGlyLysPheLeuArgSerAlaLysLysPheGlyLysAlaPheValGlyGluIleMetAsnSer
MetIleGlyLysPheLeuLysSerAlaLysLysPheGlyLysAlaPheValGlyGluIleMetAsnSer
MetIleGlyLysPheLeuPheSerAlaLysLysPheGlyLysAlaPheValGlyGluIleMetAsnSer
MetIleGlyLysPheLeuGluSerAlaLysLysPheGlyLysAlaPheValGlyGluIleMetAsnSer
MetIleGlyLysPheLeuAspSerAlaLysLysPheGlyLysAlaPheValGlyGluIleMetAsnSer
MetIleGlyLysPheLeuMetSerAlaLysLysPheGlyLysAlaPheValGlyGluIleMetAsnSer
MetIleGlyLysPheLeuTyrSerAlaLysLysPheGlyLysAlaPheValGlyGluIleMetAsnSer
MetIleGlyLysPheLeuHisAlaAlaLysLysPheGlyLysAlaPheValGlyGluIleMetAsnSer
MetIleGlyLysPheLeuHisAlaAlaLysLysPheIleLysAlaPheValGlyGluIleMetAsnSer
MetIleGlyLysPheLeuHisGluAlaLysLysPheGlyLysAlaPheValGlyGluIleMetAsnSer
MetIleGlyLysPheLeuHisThrAlaLysLysPheGlyLysAlaPheValGlyGluIleMetAsnSer -continued MetIleGlyLysPheLeuArgGluAlaLysLysPheGlyLysAlaPheValGlyGluIleMetAsnSer
MetIleGlyLysPheLeuLysGluAlaLysLysPheGlyLysAlaPheValGlyGluIleMetAsnSer
MetGlyIleGlyLysPheLeuHisSerAlaLysLysPheAlaLysAlaPheValGlyGluIleMetAsnSer
MetGlyIleGlyLysPheLeuArgSerAlaLysLysPheAlaLysAlaPheValGlyGluIleMetAsnSer
MetGlyIleGlyLysPheLeuLysSerAlaLysLysPheAlaLysAlaPheValGlyGluIleMetAsnSer
MetGlyIleGlyLysPheLeuPheSerAlaLysLysPheAlaLysAlaPheValGlyGluIleMetAsnSer
MetGlyIleGlyLysPheLeuGluSerAlaLysLysPheAlaLysAlaPheValGlyGluIleMetAsnSer
MetGlyIleGlyLysPheLeuAspSerAlaLysLysPheAlaLysAlaPheValGlyGluIleMetAsnSer
MetGlyIleGlyLysMetLeuMetSerAlaLysLysPheAlaLysAlaPheValGlyGluIleMetAsnSer
MetGlyIleGlyLysPheLeuTyrSerAlaLysLysPheAlaLysAlaPheValGlyGluIleMetAsnSer
MetGlyIleGlyLysPheLeuAlaSerAlaLysLysPheAlaLysAlaPheValGlyGluIleMetAsnSer
MetGlyIleGlyLysPheLeuHisAlaAlaLysLysPheAlaLysAlaPheValGlyGluIleMetAsnSer
MetGlyIleGlyLysPheLeuHisGluAlaLysLysPheAlaLysAlaPheValGlyGluIleMetAsnSer
MetGlyIleGlyLysPheLeuHisThrAlaLysLysPheAlaLysAlaPheValGlyGluIleMetAsnSer
MetGlyIleGlyLysPheLeuArgGluAlaLysLysPheAlaLysAlaPheValGlyGluIleMetAsnSer
MetGlyIleGlyLysPheLeuLysGluAlaLysLysPheAlaLysAlaPheValGlyGluIleMetAsnSer
MetIleGlyLysPheLeuHisSerAlaLysLysPheAlaLysAlaPheValGlyGluIleMetAsnSer
MetIleGlyLysPheLeuArgSerAlaLysLysPheAlaLysAlaPheValGlyGluIleMetAsnSer
MetIleGlyLysPheLeuLysSerAlaLysLysPheAlaLysAlaPheValGlyGluIleMetAsnSer
MetIleGlyLysPheLeuPheSerAlaLysLysPheAlaLysAlaPheValGlyGluIleMetAsnSer
MetIleGlyLysPheLeuGluSerAlaLysLysPheAlaLysAlaPheValGlyGluIleMetAsnSer
MetIleGlyLysPheLeuAspSerAlaLysLysPheAlaLysAlaPheValGlyGluIleMetAsnSer
MetIleGlyLysPheLeuMetSerAlaLysLysPheAlaLysAlaPheValGlyGluIleMetAsnSer
IleGlyLysPheLeuHisAlaAlaLysLysPheAlaLysAlaPheValGlyGluIleMetAsnSer
IleGlyLysPheLeuHisAlaAlaLysLysPheIleLysAlaPheValGlyGluIleMetAsnSer
MetIleGlyLysPheLeuHisGluAlaLysLysPheAlaLysAlaPheValGlyGluIleMetAsnSer
MetIleGlyLysPheLeuHisThrAlaLysLysPheAlaLysAlaPheValGlyGluIleMetAsnSer
MetIleGlyLysPheLeuArgGluAlaLysLysPheAlaLysAlaPheValGlyGluIleMetAsnSer
MetIleGlyLysPheLeuLysGluAlaLysLysPheAlaLysAlaPheValGlyGluIleMetAsnSer
GlyIleGlyLysPheLeuArgSerAlaLysLysPheAlaLysAlaPheValGlyGluIleMetAsnSer
GlyIleGlyLysPheLeuLysSerAlaLysLysPheAlaLysAlaPheValGlyGluIleMetAsnSer
GlyIleGlyLysPheLeuPheSerAlaLysLysPheAlaLysAlaPheValGlyGluIleMetAsnSer
GlyIleGlyLysPheLeuGluSerAlaLysLysPheAlaLysAlaPheValGlyGluIleMetAsnSer
GlyIleGlyLysPheLeuAspSerAlaLysLysPheAlaLysAlaPheValGlyGluIleMetAsnSer
GlyIleGlyLysPheLeuMetSerAlaLysLysPheAlaLysAlaPheValGlyGluIleMetAsnSer
GlyIleGlyLysPheLeuTyrSerAlaLysLysPheAlaLysAlaPheValGlyGluIleMetAsnSer
GlyIleGlyLysPheLeuAlaSerAlaLysLysPheAlaLysAlaPheValGlyGluIleMetAsnSer
GlyIleGlyLysPheLeuHisGluAlaLysLysPheAlaLysAlaPheValGlyGluIleMetAsnSer
GlyIleGlyLysPheLeuHisThrAlaLysLysPheAlaLysAlaPheValGlyGluIleMetAsnSer
GlyIleGlyLysPheLeuArgGluAlaLysLysPheAlaLysAlaPheValGlyGluIleMetAsnSer
GlyIleGlyLysPheLeuLysGluAlaLysLysPheAlaLysAlaPheValGlyGluIleMetAsnSer
IleGlyLysPheLeuHisSerAlaLysLysPheAlaLysAlaPheValGlyGluIleMetAsnSer
IleGlyLysPheLeuArgSerAlaLysLysPheAlaLysAlaPheValGlyGluIleMetAsnSer
IleGlyLysPheLeuLysSerAlaLysLysPheAlaLysAlaPheValGlyGluIleMetAsnSer
IleGlyLysPheLeuPheSerAlaLysLysPheAlaLysAlaPheValGlyGluIleMetAsnSer
IleGlyLysPheLeuGluSerAlaLysLysPheAlaLysAlaPheValGlyGluIleMetAsnSer
IleGlyLysPheLeuAspSerAlaLysLysPheAlaLysAlaPheValGlyGluIleMetAsnSer
IleGlyLysPheLeuMetSerAlaLysLysPheAlaLysAlaPheValGlyGluIleMetAsnSer
IleGlyLysPheLeuTyrSerAlaLysLysPheAlaLysAlaPheValGlyGluIleMetAsnSer
IleGlyLysPheLeuHisAlaAlaLysLysPheAlaLysAlaPheValGlyGluIleMetAsnSer
IleGlyLysPheLeuHisAlaAlaLysLysPheIleLysAlaPheValGlyGluIleMetAsnSer
IleGlyLysPheLeuHisGluAlaLysLysPheAlaLysAlaPheValGlyGluIleMetAsnSer
IleGlyLysPheLeuHisThrAlaLysLysPheAlaLysAlaPheValGlyGluIleMetAsnSer
IleGlyLysPheLeuArgGluAlaLysLysPheAlaLysAlaPheValGlyGluIleMetAsnSer
IleGlyLysPheLeuLysGluAlaLysLysPheAlaLysAlaPheValGlyGluIleMetAsnSer
MetGlyIleGlyLysPheLeuHisSerAlaLysLysPheGlyLysAlaPheValGlyGluIleMetAsnSer
GlyIleGlyLysPheLeuHisSerAlaLysProPheGlyLysAlaPheValGlyGluIleMetAsnSer
MetGlyLysPheLeuHisSerAlaLysLysPheGlyLysAlaPheValGlyGluIleMetAsnSer
MetGlyIleGlyLysPheLeuHisSerAlaLysLysPheAlaLysAlaPheValAlaGluIleMetAsnSer
GlyIleGlyLysPheLeuHisSerAlaHisLysPheGlyLysAlaPheValGlyGluIleMetAsnSer
GlyIleGlyLysPheLeuHisSerAlaLysHisPheGlyLysAlaPheValGlyGluIleMetAsnSer
GlyIleGlyLysPheLeuHisSerAlaHisHisPheGlyLysAlaPheValGlyGluIleMetAsnSer
GlyIleGlyLysPheLeuHisThrAlaLysLysPheGlyLysAlaPheValGlyGluIleMetAsnSer
GlyIleGlyLysPheLeuHisAlaAlaLysLysPheGlyLysAlaPheValGlyGluIleMetAsnSer
GlyIleGlyLysPheLeuHisGluAlaLysLysPheGlyLysAlaPheValGlyGluIleMetAsnSer
GlyIleGlyLysPheLeuLysSerAlaLysLysPheGlyLysAlaPheValGlyGluIleMetAsnSer
GlyIleGlyLysPheLeuArgSerAlaLysLysPheGlyLysAlaPheValGlyGluIleMetAsnSer
GlyIleGlyLysPheLeuPheSerAlaLysLysPheGlyLysAlaPheValGlyGluIleMetAsnSer
GlyIleGlyLysPheLeuHisSerAlaLysLysPheGlyLysAlaPheValGlyGluIleMet
GlyIleGlyLysPheLeuHisSerAlaGlyLysPheAlaLysAlaPheValAlaGluIleMetLysSer
MetGlyIleGlyLysPheLeuHisSerAlaGlyLysPheAlaLysAlaPheValAlaGluIleMetLysSer
GlyIleGlyLysPheLeuHisSerAlaGlyLysPheGlyLysAlaPheValAlaGluIleMetLysSer
GlyIleGlyLysPheLeuSerHisAlaGlyLysPheGlyLysAlaPheValGlyGluIleMetLysSer
GlyIleGlyLysPheLeuSerHisAlaLysLysPheGlyLysAlaPheValGlyGluIleMetAsnSer
GlyIleGlyLysPheLeuHisSerAlaLysLysPheGlyLysAlaPheValGlyGluIleMetArgSer
MetGlyIleGlyLysPheLeuHisSerAlaLysLysPheGlyLysAlaPheValGlyGluIleMetHisSer
GlyIleGlyLysPheLeuHisSerAlaLysLysPheGlyLysAlaPheValGlyGluIleMetProSer
GlyIleGlyLysPheLeuHisSerAlaLysLysPheGlyLysAlaPheValGlyGluIleMetLeuSer
GlyIleGlyLysPheLeuHisSerAlaGlyLysPheGlyLysAlaPheValGlyGluIleMetAsnSer
MetGlyIleGlyLysPheLeuHisSerAlaGlyLysPheGlyLysAlaPheValGlyGluIleMetArgSer
GlyIleGlyLysPheLeuHisSerAlaGlyLysPheGlyLysAlaPheValGlyGluIleMetHisSer
GlyIleGlyLysPheLeuHisSerAlaGlyLysPheGlyLysAlaPheValGlyGluIleMetLysPro
GlyIleGlyLysPheLeuHisSerAlaLysLysPheGlyLysAlaPheValGlyGluIleMetAsnPro -continued MetGlyIleGlyLysPheLeuHisSerAlaLysLysPheGlyLysAlaPheValGlyGluIleMetAsnLeu
MetGlyIleGlyLysPheLeuHisSerAlaGlyLysPheGlyLysAlaPheValGlyGluIleMetLysPro
(f)MetGlyIleGlyLysPheLeuArgGluAlaGlyLysPheGlyLysAlaPheValGlyGluIleMetLysSer
(f)MetGlyIleGlyLysPheLeuHisSerAlaGlyLysPheGlyLysAlaPheValGlyGluIleMetLysSer
(f)MetGlyIleGlyLysPheLeuHisSerAlaLysLysPheGlyLysAlaPheValGlyGluIleMetAsnSer
GlyIleGlyLysPheLeuArgGluAlaGlyLysPheGlyLysAlaPheValAlaGluIleMetLysSer
GlyIleGlyLysPheLeuHisSerAlaArgLysPheGlyLysAlaPheValAlaAlaIleMetLysSer
GlyIleGlyLysPheLeuLysGluAlaArgLysPheGlyLysAlaPheValAlaAlaIleMetLysSer
GlyIleGlyLysPheLeuHisSerAlaArgLysPheGlyLysAlaPheValAlaGluIleMetAsnSer
GlyIleGlyLysPheLeuHisSerAlaArgLysPheAlaLysAlaPheValAlaGluIleMetLysSer
GlyIleGlyLysPheLeuLysGluAlaArgLysPheAlaLysAlaPheValAlaGluIleMetAsnSer
GlyIleGlyLysPheLeuHisSerAlaArgLysPheGlyLysAlaPheValGlyGluIleMetArgSer
GlyIleGlyLysPheLeuArgGluAlaArgLysPheGlyLysAlaPheValGlyGluIleMetHisSer
GlyIleGlyLysPheLeuGluGluAlaArgLysPheGlyLysAlaPheValGlyGluIleMetIleSer
GlyIleGlyLysPheIleArgGluAlaGlyLysPheGlyLysAlaPheValGlyGluIleMetLysSer
GlyIleGlyLysPheIleHisGluAlaLysLysPheGlyLysAlaPheValGlyGluIleMetAsnSer
GlyIleGlyLysPheIleHisSerAlaLysLysPheAlaLysAlaPheValAlaGluIleMetLysSer
GlyIleGlyLysPheLeuArgGluAlaHisLysPheAlaLysAlaPheValAlaGluIleMetLysSer
GlyIleGlyLysPheLeuLysSerAlaHisLysPheAlaLysAlaPheValGlyGluIleMetAsnSer
GlyIleGlyLysPheLeuPheGluAlaHisLysPheAlaLysAlaPheValGlyGluIleMetLysPro
GlyIleGlyLysPheLeuSerHisAlaOrnLysPheGlyLysAlaPheValGlyGluIleMetLysSer
GlyIleGlyLysPheLeuArgGluAlaGlyLysPheGlyLysAlaPheValGlyAlaIleMetLysThr
GlyIleGlyLysPheLeuHisGluAlaGlyArgPheGlyLysAlaPheValGlyAlaIleMetAsnSer
GlyIleGlyLysPheLeuArgGluAlaGlyArgPheGlyLysAlaPheValGlyAlaIleMetLysSer
GlyIleGlyLysPheAsnLysGluAlaGlyLysPheGlyLysAlaPheValGlyAlaIleMetLysSer
GlyIleGlyLysPheAsnArgAlaAlaLysLysPheGlyLysAlaPheValGlyAlaIleMetAsnSer
GlyIleGlyLysPheLeuLysGluAlaGlyLysPheGlyLysAlaPheValGlyGluIleAlaLysSer
GlyIleGlyLysPheLeuHisGluAlaLysLysPheGlyLysAlaPheValGlyGluIleThrAsnSer
GlyIleGlyLysPheLeuArgAlaAlaArgArgPheGlyLysAlaPheValGlyGluIleMetArgLeu
GlyIleGlyLysPheIleHisGluAlaGlyLysPheGlyLysAlaPheValGlyGluIleMetLys3HYP
GlyIleGlyLysPheLeuHisSerAlaLysLysPheGlyLysAlaPheValGlyGluIleMet4HYPSer
GlyIleGlyLysPheLeuLysGluAlaGlyLysPheGlyLysAlaPheValGlyGluIleLysSer
GlyIleGlyLysPheLeuHisSerAlaGlyLysPheAlaLysAlaPheValGlyGluIleMetAspSer
GlyIleGlyLysPheLeuHisSerAlaLysLysPheGlyLysAlaPheValGlyGluIleMetAspSer
(f)MetIleGlyLysPheLeuHisGluAlaGlyLysPheGlyLysAlaPheValGlyGluIleMetLysSer
MetGlyIleGlyLysPheLeuLysGluAlaGlyLysPheGlyLysAlaPheValGlyGluMetLysSer
MetGlyIleGlyLysPheLeuLysGluAlaLysLysPheGlyLysAlaPheValGlyIleMetAsnSer
GlyIleGlyLysPheLeuHisGluAlaGlyLysPheGlyLysAlaPheValGlyGluIleMetLysDOPA
GlyIleGlyLysPheLeuLysAlaAlaHisArgPheGlyLysAlaPheValGlyGluIleMetLysSer
GlyIleGlyLysPheLeuHisGluAlaHisArgPheGlyLysAlaPheValGlyGluIleMetLysSer
GlyIleGlyLysPheLeuArgAlaAlaHisArgPheGlyLysAlaPheValGlyGluIleMetAsnSer
GlyIleGlyLysPheLeuLysGluAlaArgArgPheGlyLysAlaPheValGlyGluIleMetLysSer
GlyIleGlyLysPheLeuLysSerAlaArgArgPheGlyLysAlaPheValGlyGluIleMetArgSer
GlyIleGlyLysPheLeuLysGluAlaArgArgPheAlaLysAlaPheValAlaGluIleMetAsnSer
MetGlyIleGlyLysPheLeuArgAspAlaArgHisPheIleLysAlaPheValAlaGluIleMetLysSer
GlyIleGlyLysPheAsnAspGluAlaArgLysPheGlyLysAlaPheValGlyAlaIleMetHisSer
MetGlyIleGlyLysPheLeuHisGluAlaGlyLysPheGlyLysAlaPheValGlyAlaIleAlaHisSer
MetGlyIleGlyLysPheLeuLysGluAlaGlyLysPheGlyLysAlaPheValGlyAlaIleAla
MetGlyIleGlyLysPheLeuAspGluAlaGlyLysPheGlyLysAlaPheValGlyAlaIleMetLysSer
GlyIleGlyLysPheLeuArgGluAlaLysLysPheAlaLysAlaPheValGlyAlaIleMetAsp
MetGlyIleGlyLysPheLeuHisGluAlaGlyLysPheAlaLysAlaPheValAlaGluIleMet
GlyIleGlyLysPheLeuHisGluAlaLysLysPheAlaLysAlaPheValGlyGluIleMetAsnIle
GlyIleGlyLysPheLeuLysAlaAlaLysLysPheAlaLysAlaPheValAlaGluIleMetAsnSer
GlyIleGlyLysPheLeuPheLeuAlaGlyLysPheLeuLysAlaPheValAlaGluIleMetLysSer
MetGlyIleGlyLysPheIleLysGluAlaArgLysPheGlyLysAlaPheValGlyGluIleMet
GlyIleGlyLysPheLeuAlaAspAlaArgHisPheGlyLysAlaPheValGlyAlaIleMetLysSer
GlyIleGlyLysPheLeuPheGluAlaGlyLysPheGlyLysAlaPheValGlyGluIleMetAlaThr
GlyIleGlyLysPheLeuHisGluAlaGlyLysPheValLysAlaPheValGlyGluIleMetLysSer
GlyIleGlyLysPheLeuLysGluAlaLysLysPheValLysAlaPheValGlyGluIleMetAsnSer
GlyIleGlyLysPheLeuAsnHisAlaLysLysPheValLysAlaPheValAlaGluIleMetAsnSer
IleGlyLysPheLeuLysGluAlaLysLysPheGlyLysAlaPheValGlyGluIleMetAsn
IleGlyLysPheLeuArgGluAlaGlyLysPheLeuLysAlaPheValGlyGluIleMetLys
GlyIleGlyLysPheLeuLysGluAlaLysLysPheAlaLysAlaPheValAlaAlaIleMetAsnSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer -continued GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer -continued
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer
GlyIleGlyLysPheLeuSerHisAlaGlyLysPheGlyLysAlaPheValGlyGluIleMetLysSer -continued GlyIleGlyLysPheLeuSerHisAlaGlyLysPheGlyLysAlaPheValGlyGluIleMetLysSer The salts of the free acid forms of these AMPPPs and the C-terminal amide forms thereof are also the subject of this present invention, as are other and/or additional substitutions or deletions.

There are various post-synthesis modifications of AMPPPs which could improve their effectiveness against one or more plant pathogens. One such postsynthesis modification is amidation of the carboxyl termini of natural magainins and the AMPPPs of the present invention. See, for example, Cuervo et al., "The Magainins: Sequence Factors Relevant To Increased Antimicrobial Activity and Decreased Hemolytic Activity," *Peptide Res.* 1, (1988), 81-86. Amidation of AMPPPs is known to generally improve their antimicrobial activity. Other post-synthesis modifications of AMPPPs which may prove beneficial with respect to antimicrobial activity, resistance to proteolytic degradation, and/or low phytotoxicity, including those modifications which may result from post-translational modifications of AMPPPs prepared by biological expression from a DNA sequence encoding one or more AMPPPs, include, but are not limited to acetylation, glycosylation, farnesylation, amidation, tyrosine sulfonation, oxidations by chemical or enzymatic means such as by oxidation of methionine residues, proline or tyrosine hydroxylation, proline isomerization, and/or phosphorylation.

These modifications may be combined with substitutions, deletions, and/or extensions to provide a peptide which is not only resistant to plant proteolysis, but also one with increased activity against one or more plant pathogens, selected activity against specific plant pathogens, and/or low phytotoxicity. The fact that Arg and Lys have a substantial effect on proteolysis is unexpected because of the similarity in charge and/or structure between these compounds and the amino acid that they replace in naturally occurring Magainin 1, Magainin 2, and other AMPPPs in accordance with the present invention, i.e., His.

The foregoing will be better understood with reference to the following examples. These examples are for the purpose of illustration. They are not to be considered limiting as to scope and nature of the present invention.

EXAMPLE 1—PREPARATION OF [Met]Mag 2-OH (AMPPP #3)

t-Boc-[Met]Mag 2-$OCH_2PAM$ resin was prepared using an ABI Model 430A peptide synthesizer employing t-Boc protection, DCC-promoted symmetrical anhydride formation in DMF/DCM and Glu(OBzl), His(Z), Lys(Cl-Z) and Ser(Bzl) as side-chain protecting groups. The synthesis was started from 0.5 mmol (0.78 g) of t-Boc-Ser(Bzl)-$OCH_2PAM$ resin, which was subjected to repetitive deprotection, neutralization, and coupling steps following the standard DMF/t-Boc chemistry cycles used by the instrument. Before coupling of the N-terminal methionine, half of the resin was removed in order to prepare Mag 2-OH, so the last coupling was performed on only half of the resin.

The obtained t-Boc and side-chain protected resin (dry weight=0.6 g) was stirred for 50 minutes at $-5°$ C. with a solution of 6 mL of anhydrous HF, 0.6 mL of anisole, 0.23 mL of DMS and 0.18 mL of 1,2-ethanedithiol. After evaporation of the HF and DMS, the peptide/resin/scavenger mixture was washed with $3\times10$ mL of cold 99:1 ether/BME to remove scavengers and other by-products. The peptide was then extracted with $2\times6$ mL of 6M guanidine hydrochloride/1% BME. The extracts were combined, and the desired peptide was isolated directly from the guanidine hydrochloride solution by HPLC chromatography on a $2.2\times25$ cm, 10 micron, 330 angstrom, Vydac C-18 column using the following elution conditions at ambient temperature: flow rate of 4 mL/min; lineal gradient from 0% to 100% B in A over 60 min.; solvent A: 0.1% aqueous TFA; solvent B: 0.087% TFA, 10% water, 20% isopropanol, 70% acetonitrile; monitoring: UV absorbance at 229 nm. The main peak eluting at 47.6 minutes was collected to provide [Met]Mag 2-OH, presumably as its hexatrifluoroacetate salt. The peptide was shown to be greater than 95% pure by HPLC analysis. [Met]Mag 2-OH has also been prepared by the method described in Example 3.

EXAMPLE 2—PREPARATION OF [$Pro^{11}$]Mag 2-OH (AMPPP #5)

t-Boc-[$pro^{11}$]Mag 2-$OCH_2PAM$ resin was prepared according to the method given in Example 1, except that amino acids 1-14 were double coupled in DMF/DCM and His(Bom) was used instead of His(Z). Deprotection and cleavage was performed by stirring 1.0 g of the peptide-resin with a solution of 12 mL of anhydrous HF, 1.0 mL of anisole, 0.4 mL of DMS and 0.2 mL of 1,2-ethanedithiol for 30 minutes at $-10°$ C. and then for 30 minutes at 0° C. After evaporation of the HF and DMS, the residue was stirred with 5 mL of BME and then extracted with $3\times10$ mL of 15% acetic acid/2% BME. The extracts were combined and, in turn, extracted with $2\times20$ mL of diethyl ether. The acetic acid layer was then lyophilized to provide 217 mg of crude peptide, which was dissolved in about 4 mL of 1N acetic acid containing 1% BME and passed through a $2.6\times10$ cm Bio-Rad AG 1X-8 ion exchange column (acetate form) in 1N acetic acid. The peptide fractions, detected by ninhydrin monitoring (Sarin et al., supra), were combined and lyophilized to give 0.26 g of peptide, presumably now present as its pentaacetate salt. A solution of the peptide in 10% acetic acid/1% BME was further purified by eluting it through a $2.6\times70$ cm, Sephadex G-25 column at a flow rate of 1 mL/min and collecting the peptide fractions, which were detected by monitoring the effluent at 254 nm. The peptide fractions were combined and lyophilized to give 250 mg of peptide, which was shown to be greater than 90% pure by HPLC analysis and its composition was confirmed by amine acid analysis. Further purification by preparative HPLC using the method described in Example 3 provided AMPPP #5, presumably as its hexatrifluoroacetate, in greater than 98% purity (retention time=25.3 minutes).

EXAMPLE 3—PREPARATION OF [$His^{10}$]Mag 2-OH (AMPPP #12)

t-Boc-[$His^{10}$]Mag 2-$OCH^2PAM$ resin was prepared using an ABI Model 430A peptide synthesizer employing t-Boc protection, DCC/HOBT produced HOBT active esters in NMP and Glu(OBzl), His(Bom), Lys(Cl-Z) and Ser(Bzl) as side-chain protecting groups. The synthesis was started from 0.5 mmol (0.693 g) of t-Boc-Ser(Bzl)-$OCH_2PAM$ resin (substitution level=0.73 mmol/g), which was subjected to repetitive deprotection, neutralization and coupling steps following the standard NMP/t-Boc chemistry cycles used by the instrument. After drying to constant weight, 1.82 g (78%) of peptide-resin was obtained.

Deprotection and cleavage of 0.95 g of peptide-resin, using the method described in Example 2 afforded 432 mg (82%) of crude peptide. This was converted to its acetate form, using the method described in Example 2 to provide 400 mg of presumably the hexaacetate salt. The latter was dissolved in 50 mL of 10% ammonium bicarbonate and the solution was stirred under a nitrogen atmosphere for 20 hours at room temperature. Lyophilization of this solution yielded 0.38 g of peptide with an improved product profile. Final purification was accomplished by preparative, reversed phase HPLC using repetitive injections of peptide (15–30 mg) into a 2.2×25 cm, 10 micron, 300 angstrom, Vydac C-4 column and elution with the following linear gradient: 22% to 42% B in A over 40 minutes; flow rate: 6.0 mL/min; solvent A: 0.1% aq TFA; solvent B: 0.08% TFA in acetonitrile; monitoring: UV absorbance at 235 nm. The main peak eluting at 28.1 minutes, presumably the hexatrifluoroacetate form of the peptide, was collected and shown to be greater than 98% pure by HPLC.

EXAMPLE 4—PREPARATION OF [Des $Gly^1$, $Met^2$]Mag 2-OH (AMPPP #9)

t-Boc-[Des $Gly^1$, $Met^2$]Mag 2-$OCH_2PAM$ resin was prepared using the procedure given in Example 3, except that $Lys^4$ was double coupled. The composition of the peptide on the resin was confirmed by amino acid analysis (Westall et al., supra).

The peptide-resin was deprotected and cleaved using the method described in Example 2 (1.65 g of peptide-resin provided 824 mg (95%) of crude peptide). The peptide was purified by the method described in Example 3, except that after anion exchange chromatography, it was not treated with ammonium bicarbonate. Using the HPLC conditions described in Example 3, the main peak eluting at 23.8 minutes was collected to provide the desired peptide, presumably as its hexatrifluoroacetate salt, which by HPLC analysis was greater than 97% pure.

EXAMPLE 5—PREPARATION OF Met [$Ala^{13}$, $Ala^{18}$]Mag 2-OH (AMPPP #11)

t-Boc-Met [$Ala^{13}$, $Ala^{18}$]Mag 2-$OCH_2PAM$ resin was prepared, deprotected and cleaved using the procedures given in Example 3, and the peptide in its acetate form was isolated using the method described in Example 4. HPLC purification was performed as described in Example 3, except that a linear gradient from 28% to 48% B in A was instead used. The main peak eluting at 35.7 minutes, presumably the hexatrifluoroacetate form of the peptide, was collected and shown to be greater than 97% pure by HPLC.

EXAMPLE 6—PREPARATION OF [$His^{11}$]Mag 2-OH (AMPPP #13) AND [$His^{10}$, $His^{11}$]Mag 2-OH (AMPPP #14)

Using the method described in Example 3, the common segment of the two peptides, $His^{11}$-$Ser^{23}$ of Magainin 2, was assembled on a PAM resin. The resin was then split in half and the synthesis was continued in two separate vessels with the only difference being that the next amino acid coupled was a histidine in one case and a lysine in the other. Each synthesis was then completed independently using the methods described in Example 3. For the case of [$His^{11}$]Mag 2, 889 mg of peptide-resin was deprotected and cleaved in the usual manner to provide 385 mg of crude peptide, while for the case of [$His^{10}$, $His^{11}$]Mag 2, 804 mg of peptide-resin provided 320 mg (71%) of crude peptide. The peptides were purified and converted to their acetate forms using the method of Example 4, and each underwent final purification by HPLC using the method described in Example 3. The main peak eluting at 27.9 minutes for [$His^{11}$]-Mag 2-OH and 25.1 minute for [$His^{10}$, $His^{11}$]Mag 2-OH, presumably the hexatrifluoracetic forms of the peptides, were isolated and shown by HPLC to be greater than 95% pure in each case.

EXAMPLE 7—PREPARATION OF [$Arg^7$]Mag 2-OH (AMPPP #19), [$Lys^7$]Mag 2-OH (AMPPP #18) and [$Phe^7$]Mag 2-OH (AMPPP #20)

Using the method described in Example 3, the common segment of the three peptides, $Ala^9$-$Ser^{23}$ of Mag 2, was assembled on a PAM resin. Starting from 0.600 mmol of t-Boc-Ser(Bzl)-$OCH_2PAM$ resin, 1.76 g of the side-chain protected, t-Boc-$Ala^9$-$Ser^{23}$ segment of Magainin 2 on PAM resin was obtained. Half of this, 0.88 g (0.244 mmol), was put aside for use in Example 8, while the other half was coupled with t-Boc-Ser(Bzl) to produce t-Boc-$Ser^8$-$Ser^{23}$-Mag2-$OCH_2PAM$ resin. Then, using a method similar to that described by Tjoeng et al., supra, an equimolar mixture (0.667 mmol of each) of t-Boc-Arg(MTS), t-Boc-Lys(Cl-Z) and t-Boc-Phe was coupled to the resin using the t-Boc-Lys(Cl-Z)/NMP single couple cycle of the peptide synthesizer. Ninhydrin monitoring (Sarin et al., supra) indicated 99.1% coupling efficiency for this step. The peptide-resin mixture was then capped by acetylation, and appendage of the remaining common segment using the standard HOBT/NMP coupling cycles of the peptide synthesizer was completed. Ninhydrin monitoring (Sarin et al., supra) showed that coupling efficiencies ranged from 98.5 to 99.6%.

The N-terminal t-Boc group was removed by the peptide synthesizer using TFA, and the peptide mixture was then deprotected and cleaved from the resin using the following low/high HF procedure: 1.03 g of the peptide-PAM resin mixture was stirred for two hours at 0° C. with a solution of 2.5 mL of anhydrous HF, 6.5 mL of DMS and 1.0 mL of p-cresol. After evaporation of the HF and DMS, the peptide-resin mixture was stirred with a fresh solution of 12 mL of anhydrous HF, 1.0 mL of anisole, 0.4 mL of DMS, 0.2 mL of 1,2-ethanedithiol and 3.0 mg of 2-mercaptopyridine. After evaporation of the HF and other volatiles, the resin was swollen with chloroform and the mixture was washed with 3×10 mL of ether, stirred for 30 minutes with 5 mL of BME and extracted with 3×6 mL of 1:1 15% acetic acid/BME, and once with 30 mL of 50% aq. acetonitrile containing 0.1% TFA. The aqueous extracts were combined, extracted with 3×15 mL of ether and lyophilized to provide 398 mg (about 70%) of a peptide mixture, which was converted to the acetate forms using the method described in Example 4.

The peptides were separated and isolated using the HPLC procedure described in Example 3, except that the gradient used was 22% to 28% B in A for 60 minutes followed by 28% to 39% B in A for 10 minutes. The peptides, presumably as their trifluoroacetates (hexa, for $Arg^7$ and $Lys^7$; penta, for $Phe^7$) were analyzed by HPLC and FAB-MS and found to have the following characteristics (prep. HPLC RT in min, % purity by HPLC, expected $(M+H)^+$ in amu and actual $(M+H)^+$ in amu): [$Arg^7$]Mag 2 (49.8, >96, 2458.4, 2458.7); [$Lys^7$]Mag 2 (48.2, >96, 2458.4, 2458.7); and [$Phe^7$]Mag 2 (64.0,>98, 2477.3, 2477.9).

EXAMPLE 8—PREPARATION OF [$Glu^8$]May 2-OH (AMPPP #17) and [$Thr^8$]Mag 2-OH (AMPPP #15)

The PAM resin containing the segment $Ala^9$-$Ser^{23}$ of Magainin 2 in Example 7 (0.88 g, 0.244 mmol) was coupled with an equimolar mixture (0.667 mmol of each) of t-Boc-Ala, t-Boc-Glu(OBzl) and t-Boc-Thr(Bzl). The peptide-resin mixture was capped by acetylation and the remaining common segment was appended using the methods described in Example 7. Ninhydrin monitoring (Sarin et al., supra) showed that coupling efficiencies were greater than 98.5% in all cases. The peptide-resin mixture (0.940 mg) was deprotected and cleaved using the method described in Example 7 to give 352 mg (68%) of the peptide mixture, which was converted to the acetate forms using the method described in Example 4.

The peptides were separated and isolated using the HPLC procedure described in Example 3, except that the gradient used was 23% to 30% B in A for 70 minutes followed by five minutes at 30% B. The peptides, presumably as their hexatrifluoroacetates were analyzed by HPLC and FAB-MS and found to have the following characteristics (prep. HPLC RT in min, % purity by HPLC, expected $(M+H)^+$ in amu and observed $(M+H)^+$ amu): [$Ala^8$]Mag 2-OH (AMPPP #16, made for reference purposes) (67.4, >95, 2451.3, 2451.4); [$Glu^8$]Mag 2-OH (70.5,>90, 2509.3, 2509.6; and [$Thr^8$]Mag 2-OH (56.2, >95, 2481.4, 2481.7).

EXAMPLE 9—PREPARATION OF [Des $Asn^{22}$, Des $Ser^{23}$]Mag 2-OH (AMPPP #22)

Using the method described in Example 3, the common segment of the two peptides, $Gly^1$-$Ile^{20}$ of Magainin 2, was appended onto a mixture of 0.20 mmol of t-Boc-Met-$OCH_2PAM$ and 0.30 mmol of t-Boc-Met-Asn-$OCH_2PAM$ (prepared using the method of Example 3 starting from t-Boc-Asn-$OCH_2PAM$). In this synthesis, however, the segment from $Gly^1$ to $Lys^{11}$ was assembled using double couples for each amino acid. The peptide-resin mixture (1.15 g) was deprotected and cleaved using the method described in Example 7 to give 419 mg (65%) of a peptide mixture, which was converted to the acetate forms using the method described in Example 4.

The peptides were separated and isolated using the HPLC procedure described in Example 3, except that the gradient used was 20% to 23% B in A over 60 minutes followed by 23% to 25% B in A over 20 minutes. The peptides, presumably as their hexatrifluoroacetates, were analyzed by HPLC and FAB-MS and found to have the following characteristics (prep. HPLC RT in min, purity by HPLC, expected $(M+H)^+$ in amu and observed $(M+H)^+$ amu): [Des $Asn^{22}$, Des $Ser^{23}$)]Mag 2 (65.6 >94, 2266.3, 2266.4; [Des $Ser^{23}$]Mag 2 (AMPPP #21, made for reference purposes) (62.2, >92, 2380.3, 2380.6).

EXAMPLE 10—PREPARATION OF [Des $Gly^1$, Des $Ile^2$]Mag 1-OH (AMPPP #23) and [Met]Mag1-OH (AMPPP #25)

Using the method described in Example 3, except that $Gly^3$ and $Lys^4$ were double coupled, t-Boc-[Des $Gly^1$, Des $Ile^2$]Mag 1-$OCH_2PAM$ resin was synthesized starting from 0.602 mmol of t-Boc-Ser(Bzl)-$OCH_2PAM$ resin. About one-third of this peptide-resin (830 mg, dry weight) was removed and set aside. Using a single couple, an isoleucine was coupled to the remaining resin to produce t-Boc-[Des $Gly^1$]Mag 1-$OCH_2PAM$ resin and, again, about half of this (792 mg, dry weight) was removed and set aside. A glycine and a methionine were coupled to the remaining resin to produce, after drying, 661 mg of [Met]Mag 1-$OCH_2PAM$ resin. Each resin was then independently deprotected and cleaved using the procedure described in Example 3, except that 3 mg of 2-mercaptopyridine was also added as a scavenger during the HF cleavage, to give 430 mg (92%), 350 mg (84%) and 250 mg (69%), respectively, of [Des $Gly^1$, Des $Ile^2$)]Mag 1-OH, [Des $Gly^1$]Mag 1-OH (AMPPP #24, made for reference purposes) and [Met]Mag 1-OH as their hydrofluoride salts. The peptides were purified and converted to their acetate forms, presumably the hexaacetates, using the method of Example 4. HPLC analysis indicated that they were about 78%, 48% and 66% pure, respectively. The peptide [Des $Gly^1$, Des $Ile^2$]Mag 1-OH was purified by HPLC using the method described in Example 3, except that the gradient used was 18% to 38% B in A for 40 minutes. The peptide, presumably as its hexatrifluoroacetate, had a retention time of 26.0 minutes and a purity >98%.

EXAMPLE 11—PREPARATION OF [$Ala^{13}$, $Ala^{18}$]Mag 1-OH (AMPPP #26), Met [$Ala^{13}$, $Ala^{18}$]Mag 1-OH (AMPPP #27), and [$Ala^{18}$]Mag 1-OH (AMPPP #28)

Using the method described in Example 3, the sequent, $Lys^{14}$ to $Ser^{23}$ of [$Ala^{18}$]Mag 1, was synthesized on PAM resin starting from 0.601 mmol of t-Boc-Ser(Bzl). About one-third of this peptide-resin was removed and placed into another reaction vessel, and coupling was continued to produce 832 mg (dry weight) of [$Ala^{18}$]Mag 1-$OCH_2PAM$ resin. The resin remaining in the vessel was coupled until the segment, t-Boc-[$Ala^{13}$, $Ala^{18}$]Mag 1-$OCH_2PAM$ resin was produced. About half of this resin was removed (683 mg, dry weight) and a methionine was coupled to the remaining resin to produce 542 mg (dry weight) of Met [$Ala^{13}$, $Ala^{18}$]Mag 1-$OCH_2PAM$ resin. Each of the three resins was then independently deprotected and cleaved using the procedure described in Example 10 to give 285 mg (66%), 259 mg (72%) and 104 mg (37%), respectively, of [$Ala^{18}$]Mag 1-OH, [$Ala^{13}$, $Ala^{18}$]Mag 1-OH and Met [$Ala^{13}$, $Ala^{18}$]Mag 1-OH as their hydrofluoride salts. The peptides were purified and converted to their acetate forms, presumably the hexaacetates, using the method of Example 4. HPLC analysis indicated that they were about 73%, 65% and 67% pure, respectively. The peptide [$Ala^{13}$, $Ala^{18}$]Mag 1-OH was purified by HPLC using the method described in Example 3, except that the gradient used was 30% to 50% B in A for 40 minutes. The peptide, presumably as its hexatrifluoroacetate, had a retention time of 28.0 minutes and a purity >98%.

EXAMPLE 12—ANTIBACTERIAL BIOASSAYS

*Erwinia carotovora carotovora* strain SR319 (Ecc SR319) (a gift of Dr. C. H. Liao, USDA-ARS, Philadelphia, Pa.) was streaked on a plate of LB agar and grown overnight at 28° C. After 24 hours, a loopful of Ecc SR319 was picked from the agar plate and was added to 3 mL of Luria broth (10 g Bacto-tryptone, 5 g Bacto-yeast extract, and 10 g sodium chloride per liter of solution; autoclaved sterile) in a capped, sterile 10 mL test tube. This culture was grown overnight before its optical density at 630 nm was recorded using a Dynatech MR600 microplate reader (Dynatech Laboratories, Inc., Alexandria, Va.). A portion of the overnight culture was adjusted with Luria broth to obtain a culture with an optical density at 630 nm of 0.2. About 250 microliters of this culture was added to 2250 microliters of Luria broth in a capped, sterile 10 mL test tube before this diluted culture was grown for 3 hours at 28° C. in a shaking incubator. The optical density at 630 nm of the freshly grown culture was recorded and a portion of this mid-logarithmic growth phase culture was diluted 1000-fold with Luria broth to an approximate concentration of about $10^5$ colony forming units per mL of culture. About 85 microliters of this diluted culture was added to 12 wells in a 96 well microtiter plate for each AMPPP to be tested, with 1–4 replicate sets of 12 wells prepared for each AMPPP within a single experiment. Stock solutions of each AMPPP were prepared at a concentration of 1 mg/mL and 0–15 microliters of each peptide stock solution were added to a single well in the microtiter plate followed by a sufficient volume of water to bring the total well volume to 100 microliters. Typical peptide volumes assayed were 0, 1, 2, 3, 4, 5, 6, 7, 8, 9, 10 and 15 microliters, which corresponds to a final peptide concentration in the range of 0–150 micrograms/mL. The microtiter plates were sealed with parafilm and incubated on a shaking platform at 28° C. for 44 hours. The optical density of each Ecc SR319 culture well was recorded at 20 hours and then at 44 hours. A minimum complete inhibitory concentration (MCIC) was then determined for each replicate set of varying peptide concentrations for each AMPPP whereby the MCIC is defined as the lowest peptide concentration at which no bacterial growth was observed. Table I lists mean MCIC values computed after 20 hours of treatment from at least three replicate experiments with each AMPPP. "Met(S)(O)" and "Met(R-)(O)" refer to the diastereomeric forms of a methionine sulfoxide residue.

Although most of the AMPPP compounds listed in Table I were greater than 95% homogeneous following reverse phase HPLC purification, AMPPPs #24–26 and #28 were only 50–80% pure following partial purification and salt exchange by ion exchange chromatography.

TABLE I

| AMPPP # | PEPTIDE SEQUENCE | MEAN MCIC VALUE |
|---|---|---|
| *1 (Magainin 2) | GlyIleGlyLysPheLeuHisSerAlaLys-LysPheGlyLysAlaPheValGly-GluIleMetAsnSer-OH | 40 |
| *2 (Magainin 1) | GlyIleGlyLysPheLeuHisSerAlaGly-LysPheGlyLysAlaPheValGly-GluIleMetLysSer-OH | 125 |
| 3 | MetGlyIleGlyLysPheLeuHisSerAla-LysLysPheGlyLysAlaPheVal-GlyGluIleMetAsnSer-OH | 70 |

TABLE I-continued

| AMPPP # | PEPTIDE SEQUENCE | MEAN MCIC VALUE |
|---|---|---|
| *4 | GlyIleGlyLysPheLeuHisSerAlaPro-LysPheGlyLysAlaPheValGly-GluIleMetAsnSer-OH | >150 |
| 5 | GlyIleGlyLysPheLeuHisSerAlaLys-ProPheGlyLysAlaPheValGly-GluIleMetAsnSer-OH | >150 |
| *6 | GlyIleGlyLysPheLeuHisSerAlaLys-LysPheGlyLysAlaPheValGly-GluIleMet(S)(O)AsnSer-OH | >150 |
| *7 | GlyIleGlyLysPheLeuHisSerAlaLys-LysPheGlyLysAlaPheValGly-GluIleMet(R)(O)AsnSer-OH | >150 |
| *8 | GlyIleGlyLysPheLeuHisSerAlaGly-LysPheGlyLysAlaPheValGly-GluIleLysSer-OH | >150 |
| 9 | MetGlyLysPheLeuHisSerAlaLysLys-PheGlyLysAlaPheValGlyGlu-IleMetAsnSer-OH | 150 |
| *10 | GlyIleGlyLysPheLeuHisSerAlaLys-LysPheAlaLysAlaPheValAla-GluIleMetAsnSer-OH | 5 |
| 11 | MetGlyIleGlyLysPheLeuHisSerAla-LysLysPheAlaLysAlaPheVal-AlaGluIleMetAsnSer-OH | 25 |
| 12 | GlyIleGlyLysPheLeuHisSerAlaHis-LysPheGlyLysAlaPheValGly-GluIleMetAsnSer-OH | >150 |
| 13 | GlyIleGlyLysPheLsuHisSerAlaLys-HisPheGlyLysAlaPheValGly-GluIleMetAsnSer-OH | >150 |
| 14 | GlyIleGlyLysPheLeuHisSerAlaHis-HisPheGlyLysAlaPheValGly-GluIleMetAsnSer-OH | >150 |
| 15 | GlyIleGlyLysPheLeuHisThrAlaLys-LysPheGlyLysAlaPheValGly-GluIleMetAsnSer-OH | >150 |
| *16 | GlyIleGlyLysPheLeuHisAlaAlaLys-LysPheGlyLysAlaPheValGly-GluIleMetAsnSer-OH | 70 |
| 17 | GlyIleGlyLysPheLeuHisGluAlaLys-LysPheGlyLysAlaPheValGly-GluIleMetAsnSer-OH | >150 |
| 18 | GlyIleGlyLysPheLeuLysSerAlaLys-LysPheGlyLysAlaPheValGly-GluIleMetAsnSer-OH | 35 |
| 19 | GlyIleGlyLysPheLeuArgSerAlaLys-LysPheGlyLysAlaPheValGly-GluIleMetAsnSer-OH | 30<br>30 |
| 20 | GlyIleGlyLysPheLeuPheSerAlaLys-LysPheGlyLysAlaPheValGly-GluIleMetAsnSer-OH | 140 |
| *21 | GlyIleGlyLysPheLeuHisSerAlaLys-LysPheGlyLysAlaPheValGly-GluIleMetAsn-OH | 50 |
| 22 | GlyIleGlyLysPheLeuHisSerAlaLys-LysPheGlyLysAlaPheValGly-GluIleMet-OH | >150 |
| 23 | GlyLysPheLeuHisSerAlaGlyLysPhe-GlyLysAlaPheValGlyGluIle-MetLysSer-OH | >150 |
| *24 | IleGlyLysPheLeuHisSerAlaGlyLys-PheGlyLysAlaPheValGlyGlu-IleMetLysSer-OH | 70 |
| 25 | MetGlyIleGlyLysPheLeuHisSerAla-GlyLysPheGlyLysAlaPheVal-GlyGluIlemetLysSer-OH | 55 |
| 26 | GlyIleGlyLysPheloeuHisSerAlaGly-LysPheAlaLysAlaPheValAla-GluIlemetLysSer-OH | 15 |
| 27 | MetGlyIleGlyLysPheLeuHisSerAla-GlyLysPheAlaLysAlaPheVal-AlaGluIlemetLysSer-OH | 25 |
| 28 | GlyIleGlyLysPheLeuHisSerAlaGly-LysPheGlyLysAlaPheValAla-GluIleMetLysSer-OH- | 20 |
| *29 (Magainin 2- | GlyIleGlyLysPheLeuHisSerAlaLys-LysPheGlyLysAlaPheValGly- | 20 |

TABLE I-continued

| AMPPP # | PEPTIDE SEQUENCE | MEAN MCIC VALUE |
|---|---|---|
| amide) | GluIleMetAsnSer-$NH_2$ | |

*For comparison purposes

Most of the AMPPPs tested were effective in controlling the growth of Ecc SR319. However, many of the AMPPPs, such as Nos. 4, 5, 6, 7, 8, 12, 13, 14, 15, 22, and 23, were not active against Ecc SR319 even at concentrations higher than 150 micrograms AMPPP/mL.

EXAMPLE 13—ANTIFUNGAL BIOASSAY

Fungi are grown on an appropriate medium, in this case a potato dextrose agar plate, for several weeks. At the end of that period, the plate was flooded with about 5 mL of sterile distilled water to harvest spores. The spore concentration was determined by use of a hemocytometer and the spore suspension was stored in a sterile tube at 4° C. until it was needed. Then 82 microliters of potato dextrose broth and 3 microliters of spore suspension (ranging from $10^5$ to $10^7$ spores total) was then added to 12 wells in a 96 well microtiter plate for each AMPPP to be tested, with 1–4 replicate sets of 12 wells prepared for each AMPPP within a single experiment. In several instances, more than one spore concentration was used in order to determine the efficacy of certain AMPPPs as a function of the number of target spores. Stock solutions of each AMPPP were prepared at a concentration of 1 mg/mL and 0–15 microliters of each peptide stock solution were added to a single well in the microtiter plate followed by a sufficient volume of water to bring the total well volume to 100 microliters. Typical peptide volumes assayed were 0, 1, 2, 3, 4, 5, 6, 7, 8, 9, 10, and 15 microliters, which corresponds to a final peptide concentration in the range of 0–150 micrograms/mL. The microtiter plates were sealed with parafilm and incubated at room temperature for 48 hours. The fungal growth was observed after 24 and 48 hours by microscope using a 4× and/or a 10× objective lens. The amount of spore germination and fungal growth was recorded as a qualitative measurement at each observation time using a system of pluses and minuses: [−] meant no germination having occurred, [+] meant swollen spores with an extended germ tube, [++] meant the beginnings of mycelial growth with the overall appearance of a loose lattice, and [+++] meant a dense mycelial growth with the overall appearance of a thick opaque meshwork. The MCIC value for each AMPPP tested was then recorded, where the MCIC value is defined as the lowest peptide concentration at which no spore germination occurred (rating=[−]). Table II lists mean MCIC values computed after 24 hours of treatment from at least three replicates with each AMPPP for each of two or three plant pathogenic fungi tested: *Alternaria alternata* (a gift of Dr. Harvey Spurr, Jr., USDA-ARS, Oxford, N.C.), P3 Fusarium (field isolate), and *Trichoderma reesei* (a gift of Dr. John Ellis, USDA-ARS, Peoria, Ill.). The identity of AMPPPs in Table II is the same as detailed in Table I.

TABLE II

| | Mean MCIC Values against: | | |
|---|---|---|---|
| AMPPP # | *Alternaria alternata* ($10^6$ spores) | P3 Fusarium ($10^7$ spores) | *Trichoderma reesei* ($10^6$ spores) |
| *1 (Mag 2) | 85 | 43 | 55 |
| *2 (Mag 1) | NT | 40 | 30 |
| 3 | 110 | 40 | 50 |
| *4 | NT | >150 | >150 |
| 5 | NT | >150 | 90 |
| *6 | NT | 40 | 75 |
| *7 | NT | 50 | 75 |
| *8 | NT | 75 | 75 |
| 9 | 150 | 75 | 75 |
| *10 | 120 | 100 | 90 |
| 11 | 140 | 100 | 110 |
| 12 | 100 | 40 | 30 |
| 13 | 95 | 65 | 40 |
| 14 | 130 | 70 | 50 |
| 15 | NT | 40 | NT |
| *16 | NT | 20 | NT |
| 17 | NT | 40 | NT |
| 18 | NT | 30 | 50 |
| 19 | NT | 30 | 65 |
| 20 | NT | 50 | 70 |
| *21 | NT | 40 | 50 |
| 22 | NT | 60 | 60 |
| 23 | NT | 35 | 150 |
| *24 | NT | 55 | >150 |
| 25 | NT | 25 | 80 |
| 26 | NT | 20 | 55 |
| 27 | NT | 35 | 55 |
| 28 | NT | 40 | 60 |
| *29 (Mag 2-$NH_2$) | NT | 20 | 40 |

*For comparison purposes
NT = not tested

There is some variability in response among the three fungal plant pathogens tested, but in general almost all of the AMPPPs tested were active against all fungi tested at some treatment dose in the range 0–150 micrograms AMPPP/mL. The exceptions to the AMPPPs active against fungi were AMPPP 4 for both P3 *Fusarium* and *Trichoderma reesei* and AMPPP 5 for P3 *Fusarium*. Many of the AMPPP compounds were approximately as active against plant pathogenic fungi as against bacterium Ecc SR319 (for example, AMPPPs 1, 16, 18, 19, 21, and 27), while certain AMPPP compounds were much more effective against plant pathogenic fungi than against bacterium Ecc SR319. The latter category includes, but is not limited to, AMPPPs 2, 6–9, 12–15, 17, and 26. These latter compounds are of great importance in conjunction with protecting plants from plant pathogens because the biospecificity allows for protection against fungi without threat to certain beneficial bacteria in the soil or environment.

Note that some variability occurred between experiments and is attributable to differences in the biological test material. This variability is implicit in the mean values calculated for Table II.

EXAMPLE 14—MEASURE OF RESISTANCE TO PROTEOLYTIC DEGRADATION

To determine the sensitivity of AMPPPs to extracellular proteases, and to determine the site of processing by these proteases, a system was designed to obtain extracellular fluid from leaves of maize, tobacco, and potato and to use these to test the stability of AMPPPs.

Extracellular fluid (ECF) was obtained in accordance with Z. Klement, "Method Of Obtaining Fluid From the Intercellular Space of Foliage and the Fluid's Merit As Substrate For Phytobacterial Pathogens," supra by cutting interveinal pieces from tobacco leaf after they were rinsed in deionized water. The segments were submerged in water in a vacuum desiccator and vacuum was applied for five to 10 minutes. The vacuum was released slowly, the leaves were blotted dry and four to five pieces were rolled and placed in a 50 mL disposable syringe barrel cut down so as to be able to fit in a swinging bucket centrifuge rotor. The syringe barrel was placed in a 50 mL screw cap conical centrifuge tube and centrifuged in a swinging bucket rotor at 500×g for 30 minutes. The liquid was recovered and centrifuged in a microfuge for 10 minutes. The supernatant was stored at −80° C. and used in subsequent experiments.

To test the stability of the magainin analogs to extracellular plant proteases, 20 micrograms of the magainin peptide analog (1 mg/mL) was incubated with 0, 1, 2.5, 5, and 10% extracellular fluid in 50 mM Tris, pH 7.4. After incubation at 37° C. for one hour the proteases were inactivated by the addition of TFA to 1% final volume.

Peptides were analyzed by reverse phase chromatography on a 4.6 mm×250 mm Vydac C-4 protein column (Nest Group, Southboro, Mass.) using a 0% to 60% acetonitrile gradient in 0.1% TFA in 30 minutes on a Hewlett-Packard HP1090 high pressure liquid chromatograph (Hewlett-Packard, Avondale, Pa.). When the amount of ECF was increased it was observed that two early eluting peaks were generated from the parent peak. These peptides were purified and analyzed by FAB-MS and amino acid analysis. The results indicated among other things that the earliest eluting peptide fragment was residues $Gly^1$ to $Xaa^7$. The values shown in Table III represent the percent of the area in the parent peak and the $Gly^1$–$Xaa^7$ peak obtained after incubation of the indicated AMPPP with 2.5% (v/v) ECF, relative to area of the AMPPP parent peak with no added ECF. The results indicate that modification of AMPPPs by substitution of Arg, Lys or Phe at position 7 and Glu at position 8 provide significant resistance to proteolysis at the $Xaa^7$–$Xaa^8$ peptide bond.

TABLE III

| | Total Area Under Chromatogram Peaks | |
|---|---|---|
| AMPPP # | Parent AMPPP | Fragment $Gly^1Xaa^7$ |
| *1 | 54.4 | 15.2 |
| 15 | 55.6 | 11.1 |
| *16 | 58.9 | 13.9 |
| 17 | 95.9 | 0.7 |
| 18 | 68.5 | 6.1 |
| 19 | 63.9 | 7.0 |
| 20 | 62.5 | 3.9 |

*For comparison purposes

EXAMPLE 15—THE EFFECT OF ECF ON ANTIFUNGAL ACTIVITIES OF AMPPPs

It is critical to understand the effect of plant proteolytic enzymes on AMPPP activity because any AMPPP applied to crop plants will be in contact with plant tissues and any associated plant proteases. It is important to assess the bioactivity of an AMPPP which may be cleaved by one or more plant proteases as well as to recognize that such an event has occurred. An extract of extracellular fluid (ECF) as described in Example 14 is a useful reagent in determining such loss of antimicrobial activity of AMPPPs due to exposure to plant proteases in the extracellular compartment of plant tissues. Bioassay experiments were conducted with 300–1000 pregerminated P3 Fusarium spores essentially as described in Example 13 for various AMPPPs exposed to ECF from several crop species, or exposed to spent media collected as a supernatant from centrifuged three-day-old P3 Fusarium cultures grown in potato dextrose broth (PDB), corn stalk medium (CSM), or water as detailed below. The only major difference in the bioassay method used from that described in Example 13 was that the bioassay was conducted in a total culture volume of 10 microliters rather than 100 microliters. ECF was present in these bioassays at a final concentration of 10% (v/v) and was added concurrently with an AMPPP to the Fusarium spores at various AMPPP concentrations. The bioassay results from these tests were interpreted as described in Example 13, and an approximate percent reduction in antifungal activity for any AMPPP was obtained from the comparison of the minimal complete inhibitory concentration (MCIC) with and without addition of ECF. Table IV summarizes the results of these tests with various AMPPP compounds. In general, the activity of all AMPPPs was inhibited by the presence of ECF. The likelihood that the inhibition was due to the proteolytic activity present in the ECF samples was supported by the observation that treatment of the ECF with 2% phenylmethylsulfonylfluoride, a known protease inhibitor, or heating of the ECF in a boiling water bath for 10 minutes, eliminated the capacity of the ECF to inhibit AMPPP antifungal activity.

TABLE IV

| ECF Source | AMPPP # | Approximate % Reduction in Antifungal Activity by ECF |
|---|---|---|
| Tobacco Leaf | *1 | 75 |
| | *2 | 50 |
| | 3 | 75 |
| | *4 | 50 |
| | 5 | 50 |
| | *6 | 50 |
| | 8 | 50 |
| | 9 | 85 |
| | *10 | 85 |
| | 11 | 85 |
| | 12 | 75 |
| | 13 | 85 |
| | 14 | 50 |
| Potato Leaf | 5 | 75 |
| | *10 | 85 |
| | 11 | 50 |
| | 12 | 75 |
| | 13 | 75 |
| | 14 | 75 |
| Corn Leaf | 5 | 50 |
| | *10 | 75 |
| | 11 | 50 |
| | 12 | 75 |
| | 13 | 75 |
| Corn (B73) upper stalk | *1 | 85 |
| Corn (B73) lower stalk | *1 | 85 |
| P3 Fusarium spent media: | | |
| PDB | *1 | 75 |
| CSM | *1 | 75 |
| water | *1 | 50–75 |

*For comparison purposes

EXAMPLE 16—ANALYSIS OF PROTEASES SECRETED FROM PLANT FUNGAL CELLS

Extracellular proteases may also be produced in spent tissue culture media and fungal culture media and used as in Example 14 for the determination of resistance to proteolytic degradation. There are several advantages to using proteases collected from spent tissue culture media. Specifically, the concentration and contents of successive batches tend to be more consistent, and the method in accordance with the present invention allows for collection of proteases from a greater variety of plants and plant pathogens. It is therefore possible to consider the proteolytic resistance of an AMPPP to both host organism proteases and plant pathogenic proteases.

These protease-containing reagents were obtained by removing the cells from media by centrifugation and adjusting the supernatant to 50 mM Tris pH 7.4 by 20-fold dilution of a 1M Tris, pH 7.4, stock solution.

EXAMPLE 17—OXYGEN EVOLUTION BIOASSAY FOR PHYTOTOXICITY

The following procedure for the preparation of chloroplasts to use in an oxygen electrode is similar to that of Gupta et al., "Development and Use of Chlorotetracycline Fluorescence As a Measurement Assay of chloroplast Envelope-Bound $Mg^{2+}$, " *Plant Physiol* 89, (1989) 753-761. Spinach (*Spinacia oleracea* L. var. 'Melody') was grown in 1:1 peat/vermiculite potting mix in a growth chamber with a 10 hour light period. The chamber temperature was maintained at 21° C. (day) and 16° C. (night) during the growth period. All plants were used for chloroplast isolation after 6-8 weeks of growth.

In order to obtain an enriched chloroplast fraction, about 12 g of deribbed spinach leaves were thoroughly washed and surface dried. The leaves were then cut into small pieces, each about ½ inch square, and were placed in a small blender jar containing 50 mL of chilled homogenization medium (0.33M sorbitol, 50 mM Hepes-NaOH, pH 6.8, 2 mM $Na_2EDTA$, 1 mM $MnCl_2$, 1 mM $MgCl_2$). The tissue was blended twice for three second intervals on high speed in a blender. The resulting homogenate was filtered through four layers of cheesecloth and two layers of miracloth (Behring Diagnostics, La Jolla, Calif. ) into two chilled 30 mL glass centrifuge tubes. The filtered solution was centrifuged for 1.0 minute at 750 g (2,200 RPM) in a JS 13.1 swinging bucket rotor in a Beckman J2-21M centrifuge (Beckman Instruments, Inc., Somerset, N.J.). The supernatant-was then decanted and the pellet was gently resuspended by swirling at 0° C. About 15 mL of homogenization medium was added to each tube of chloroplasts before the chloroplasts were layered onto a 40% Percoll gradient (6 mL Percoll, 9 mL homogenization medium, and 0.03 g bovine serum albumin) in a 30 mL glass centrifuge tube. These tubes were centrifuged for 4.0 minutes at 2500 g (4000 RPM) in a JS 13.1 swinging bucket rotor in a Beckman J2-21M centrifuge. The resulting pellet was resuspended in a small amount of homogenization medium (about 500 microliters).

Plastid concentration was generally expressed on a chlorophyll basis. Chlorophyll is determined by the method of Arnon "Copper Enzymes In Isolated Chloroplasts, Polyphenol Oxidase is Beta Vulgaris," *Plant Physiol.* 24, (1949) 1-15. About 50 microliters of chloroplast stock suspension was added to 10 mL of 80% acetone and this solution was incubated 5.0 minutes in the dark and then centrifuged for 5.0 minutes at 500 g (1630 RPM) in a Beckman GP centrifuge. The absorbance of the acetone-chloroplast solution was monitored at 645 nm, at 663 nm and at 730 nm. The chlorophyll concentration was then calculated as $10\times$[(absorbance at 645 nm$\times$20.2)+(absorbance at nm$\times$8.02)−background at 730 nm]. This gave the amount of chlorophyll in micrograms for the original 50 microliters of chloroplasts. The concentration of chloroplasts was then adjusted with homogenization medium so that 50 microliters of suspension contains 26 micrograms of chlorophyll. These chloroplasts were only active for 1½ to 2 hours and were therefore used immediately.

An oxygen electrode (Hansatech Instruments Ltd., Kings Lynn, Norfolk, England) was used to measure oxygen evolution from isolated chloroplasts. For a detailed discussion of the method see, D. Walker, "The Use Of the Oxygen Electrode and Fluorescence Probes In Simple Measurements Of Photosynthesis," supra . A saturated KCl solution was placed in the electrode well and a 1 inch square of rolling paper or lens paper was placed into the electrode well so that it soaked up KCl and formed an ionic bridge. A one-inch square of teflon membrane was then prepared, being careful not to touch its surface, and was placed over the soaked paper. Using the membrane applicator, an O ring was placed over the head of the electrode, thereby securing paper and membrane across the electrode. The CB-1D control box was turned on and the system was allowed to warm up approximately one hour before calibration. The system was then calibrated using air-saturated water (vigorously shaking a wash bottle of deionized water). Using the gain switch, the output was subsequently set so that the pen on the chart recorder was at the maximum chart height. To remove all air from the water in the cuvette and to zero the chart recorder, about 2-3 mg of sodium dithionite was added and the plotter pen was observed to move to the bottom of the graph. If the slope of the line were unstable, the membrane and paper were removed and the setting up of the oxygen electrode was restarted.

In order to carry out a phytotoxicity bioassay with the oxygen electrode, the following components were added to the oxygen electrode cuvette: 855 microliters assay medium (homogenization medium adjusted to pH 7.6 plus 25 mM $NaH_2PO_4$), 50 microliters of 0.1M fresh $NaHCO_3$, 20 microliters catalase (a total of 49.6 units/-microliter), and 50 microliters chloroplast suspension (added last). The light source to the electrode then was turned on. An initial lag phase was seen as the chloroplast system equilibriated. If the initial lag phase was greater than one minute, then the plants used for chloroplast isolation were judged to be inadequate. In productive experiments, a steady rate of oxygen evolution was established for 2-3 minutes, then 25 microliters of solution containing peptide were added using a Hamilton syringe. The oxygen evolution rate was monitored for 4 minutes after peptide addition. The reduction in rate of oxygen evolution in these experiments after the addition of a peptide was determined by comparing the slope of the chart recorder output line before the addition of the peptide to the slope of the line at a set time point after addition of the peptide. The results were normalized for chlorophyll content since there was some variability between experiments in chloroplast concentration. The final result was expressed as percent inhibition of oxygen evolution derived by dividing the rate of oxygen evolution after addition of the peptide by the initial control rate of oxygen evolution and multiplying that number by 100.

Table V summarizes observations on several AMPPPs for chloroplasts exposed to peptides at a final concentration of 16 uM unless otherwise noted. Mean values and standard deviations were calculated from 3–15 replicate assays with each AMPPP. Control oxygen evolution rates were in the range of 72–283 umoles $O_2$/hour/mg chlorophyll. Multiple peptides were studied in each experiment to minimize day-to-day variability in the results. The identity of individual AMPPPs as listed corresponds to the peptides listed in Table I of Example 12.

TABLE V

| AMPP # | Percent Inhibition of Oxygen Evolution (Mean +/− S.D.) |
|---|---|
| *1 (Magainin 2) | 71 +/− 13 |
| **1 | 67 +/− 10 |
| *2 (Magainin 1) | 24 +/− 16 |
| **2 | 2 +/− 4 |
| 3 | 70 +/− 7 |
| 4 | 8 +/− 12 |
| 5 | 62 +/− 14 |
| 6 | 39 +/− 14 |
| 8 | 5 +/− 9 |
| 9 | 42 +/− 11 |
| *10 | 100 +/− 0 |
| 11 | 100 +/− 0 |
| 12 | 58 +/− 16 |
| 13 | 66 +/− 16 |
| 14 | 64 +/− 8 |
| **15 | 27 +/− 16 |
| *, **16 | 90 +/− 10 |
| **17 | 38 +/− 21 |
| **18 | 56 +/− 35 |
| **19 | 84 +/− 17 |
| **20 | 41 +/− 20 |
| *, **21 | 2 +/− 3 |
| **22 | 11 +/− 14 |
| *, **29 | 57 +/− 23 |

*For comparison purposes
**Final peptide concentration was 8 micromolar

EXAMPLE 18—CONSTRUCTION OF SYNTHETIC AMPPP Met-Magainin 2 GENE AND ESTABLISHMENT OF THE SYNTHETIC *GENE IN ESCHERICHIA COLI.*

A synthetic Met-Magainin 2 gene was designed on the basis of the universal genetic code and a bacterial codon usage table (see H. A. DeBoer and R. A. Kastelein, "Biased codon usage: an exploration of its role in optimization of translation", in *Maximizing Gene Expression* (W. S. Reznikoff and L. Gold, Eds.; Butterworths, Boston, 1986), pp. 225–285, and J. Brosius, "Expression vectors employing lambda-, lac- and lpp-derived promoters", in Vectors: a Survey of Molecular Cloning Vectors and Their Uses (R. L. Rodriguez and D. T. Denhardt, Eds.; Butterworths, Boston, 1988), pp. 205–225) and with flanking non-equal EcoR1 and HindIII restriction endonuclease recognition sequences for convenient directed insertion into the polylinker region of the commercially available bacterial plasmid pKK223-3 (LKB/Pharmacia Inc., Piscataway, N.J.) capable of regulated expression. Regulated expression of the synthetic gene is desirable to avoid deleterious effects on the growth of the host cells due to toxic activity of Met-Magainin 2. The synthetic gene incorporates ATG as the first codon appended to a DNA sequence encoding Magainin 2 in order to allow for expression of this peptide in the genetically well-defined bacterium *Escherichia coli.* The synthetic gene would be assembled from two oligonucleotides prepared on an Applied Biosystems Model 391 PCR-Mate oligonucleotide synthesizer using beta-cyanoethyl phosphoramidite chemistry. The sequence of the two synthetic oligonucleotides assembled to prepare the synthetic gene would be 5'-AAT TCA TAT ATG GGA ATT GGT AAA TTT (I)
TTG CAC TCA GCA AAA AAA TTT GGA AAA GCT
TTT GTG GGA GAG ATA ATG AAT TCA TAA GTC
A-3';

5'-AGC TTG ACT TAT GAA TTC ATT ATC TCT (II)
CCC ACA AAA GCT TTT CCA AAT TTT TTT GCT
GA TGC AAA AAT TTA CCA ATT CCC ATA TAT
G-3'.

1–3 micrograms of each of the above oligonucleotides would be combined in 15 microliters of sterile distilled water to which would be added 2 microliters of 10× linker kinase buffer (see T. Maniatis et al., *Molecular Cloning, p.* 125; Cold Spring Harbor Laboratory, Cold Spring Harbor, N.Y., 1982) and 2 microliters of 4 mM ATP. This solution would be heated to 65°–70° C. for 2–3 minutes and cooled slowly to room temperature over a period of at least 45 minutes to allow the oligonucleotides to anneal to one another. One microliter of T4 polynucleotide kinase (GIBCO BRL, Gaithersburg, Md.; at least 10 U/microliters (U=units)) would be added to the cooled mixture and the solution would be incubated for 60 minutes at 37° C. The reaction mixture would then be heated to 65° C. for five minutes to inactivate the kinase enzyme.

Five micrograms of the plasmid pKK223-3 would be digested to completion in a total volume of 15 microliters with the restriction enzymes EcoR1 and HindIII (New England Biolabs, Inc., Beverly, Mass.) according to the manufacturer's specifications or known methods. See T. Maniatis et al. in *Molecular Cloning,* supra, at pp. 98–106. Successively, 29 microliters of water, 5 microliters of 10× T4 DNA ligase buffer (International Biotechnologies, Inc., New Haven, Conn.) and 1 microliter of calf intestinal alkaline phosphatase (Boehringer Mannheim, Indianapolis, Ind.; 1 U/microliter) then would be added to the restriction digest mixture. This phosphatase reaction mixture would be incubated at 37° C. for 30 minutes and then for 15 minutes at 65° C. before the phosphatase reaction mixture would be extracted twice with 50 microliters phenol:chloroform (1:1) equilibrated against 10 mM Tris-HCl , pH 7.5, 1 mM $Na_2EDTA$. Eight microliters of 5M ammonium acetate and 150 microliters of (−20° C.) 100% ethanol then would be added to the aqueous reaction mixture and the sample would be stored 10 minutes at −20° C. before it would be centrifuged in an Eppendorf microfuge at 4° C. for 30 minutes. The supernatant would be discarded and the pellet would be dried under vacuum for 3–5 minutes. The dried pellet then would be resuspended in 10 microliters sterile distilled water and the entire sample electrophoresed in an 0.8% agarose gel containing 1 microgram/mL ethidium bromide in 1× TBE buffer (89 mM Tris-OH, 89 mM boric acid, pH 8.3, 2.5 mM $Na_2EDTA$). Full-length linear pKK223-3 plasmid DNA would be visualized under long-wavelength ultraviolet light and the linear DNA band would be excised from the gel with a razor blade. Purified linear plasmid DNA would be obtained from this sample using Gene-Clean (Bio 101, La Jolla, Calif.) according to the manufacturer's specifications or similar procedures such as size exclusion chromatography. See Maniatis et al., supra, pp. 464–467.

Linear phosphtased pKK223-3 DNA and annealed oligonucleotides would be mixed in a molar ratio of 1:10 using at least 0.5 micrograms of pKK223-3 DNA in a solution containing 16 microliters of DNA in water. Then 2 microliters of 10× ligase buffer (International Biotechnolgoies Inc.) and 2 microliters of T4 DNA ligase (New England Biolabs; 400,000 U/microliters) would be added. This ligation reaction mixture would be incubated overnight at 14°–15° C.

Competent *Escherichia coli* strain IG109 cells (I. Goldberg et al., "Cloning and expression of a collagen-analog-encoding synthetic gene in *Escherichia coli*, Gene 80, (1989), 305–314) would be prepared by conventional means (see T. Maniatis et al., op. cit., p. 250). Two microliters of the ligation reaction mixture would be mixed on ice with 100 microliters of competent cells and the mixture left on ice for 30–60 minutes. The transformation mixture would then be heated at 42° C. for 60 seconds, chilled on ice for two additional minutes and then 500 microliters LB broth (T. Maniatis et al., op. cit., p. 440) would be added. This cell mixture would be incubated at 37° C. for 45 minutes, the cells would be spun briefly and the supernatant would be replaced with 200 microliters of fresh LB broth. Portions of the resuspended cell pellet then would be plated on LB/ampicillin agar selective plates and the plates would be incubated overnight at 37° C. Bacterial colonies found on the selective plates the next day would be screened to confirm the presence of the recombinant plasmid by preparing plasmid mini-preps (T. Maniatis et al., op. cit., pp. 368–369), digesting a portion of each plasmid miniprep with EcoR1 and HindIII restriction enzymes and analyzing the digestion products on an 0.8% analytical agarose gel in 1× TBE buffer.

Regulated expression of the synthetic [(f)Met]-Magainin 2 gene would be achieved by fermenting a recombinant bacterial clone at 37° C. and increasing the temperature of the culture to 42° C. for 2–60 minutes. The temperature of the culture could then be reduced to 37° C. for 30–90 minutes before the cells would be harvested. The bacterial cell paste could then be passed through a French press and the Met-Magainin 2 purified by conventional means. See, for example, Chapter 16 of *Current Protocols in Molecular Biology*, F. M. Ausubel et al., Eds.; Wiley Interscience, 1988.

EXAMPLE 19—PREPARATION OF AMPPPs, FOR COMPARISON

A number of peptides related to the AMPPP compounds described in this invention were required for comparison purposes. Magainin 2-OH (AMPPP #1) and Magainin 1-OH (AMPPP #2) were purchased from Applied Biosystems, Inc., Foster City, Calif. or were made using the procedures described in Examples 1 and 3. [$Pro^{10}$]Mag 2-OH (AMPPP #4) was synthesized by the method given in Example 4, but was purified by preparative HPLC using conditions similar to those given in Example 3. The diastereomeric sulfoxides, [$Met^{21}$(S)(O)Mag 2-OH and [$Met^{21}$(R)(O)]Mag 2-OH (AMPPPs #6 and #7, sterochemistry arbitrarily assigned) were isolated by preparative HPLC as by-products from the synthesis of Magainin 2. [Des $Met^{21}$]Mag 1-OH (AMPPP #8) was prepared in the same manner as AMPPP #4. [$Ala^{13}$, $Ala^{18}$]Mag 2-OH (AMPPP #10) was prepared by the method of Example 5. [$Ala^{18}$]Mag2-OH (AMPPP #16) was prepared in Example 8. [Des $Ser^{23}$]Mag 2-OH (AMPPP #21) was prepared in Example 9. [Des $Gly^{1}$]Mag 1-OH (AMPPP #24) was prepared in Example 10. Mag 2—$NH_2$ (AMPPP #29) was purchased from Applied Biosystems, Inc., Foster City, Calif. Since all of these peptides were purified by HPLC using water/acetonitrile containing 0.1% TFA, it is assumed that they were all present as their trifluoroacetate salts. All of the peptides were analyzed by HPLC and found to be at least 94% pure.

The principles, preferred embodiments, and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention. For example, derivatives of the AMPPPs in accordance with the present invention which are equivalent in structure and/or function are encompassed within the scope of this disclosure.

We claim:

1. An AMPPP which is a Magainin 2 derivative having increased resistance to proteolytic degradation when compared to naturally occurring Magainin 2 having an amino acid sequence of GlyIleGlyLysPheLeuHisSerAlaLys LysPheGlyLysAlaPheValGlyGluIleMetAsnSer, said increased resistance to proteolytic degradation being imparted by a substitution for at least one of the amino acids His, Met, Asn, and the non-C terminal Ser which are natural occurring in Magainin 2.

2. The AMPPP of claim 1 wherein said amino acid His is substituted with an amino acid selected from the group consisting of Phe, Ala, Glu, Asp, Lys, Ser and Arg.

3. The AMPPP of claim 2 wherein said amino acid His is substituted with an amino acid selected from the group consisting of Arg, Lys and Phe.

4. The AMPPP of claim 1 wherein said amino acid Ser is substituted with an amino acid selected from the group consisting of Thr, Asp, Ala, His and Glu.

5. The AMPPP of claim 4 wherein said amino acid Ser is substituted with the amino acid Glu.

6. The AMPPP of claim 1 wherein said amino acid Met is substituted with an amino acid selected from the group consisting of Arg, Lys, His, Gln, Trp, Tyr, Thr, Val, Ala, Leu, Ile, Glu, Asp and Phe.

7. The AMPPP of claim 6 wherein said amino acid Met is substituted with an amino acid selected from the group consisting of Thr, Val, Leu, Ile and Phe.

8. The AMPPP of claim 1 wherein said amino acid Asn is substituted with an amino acid selected from the group consisting of Arg, His, Glu, Trp, Tyr, Thr, Val, Ala, Leu, Ile, Gly, Asp, Phe, Pro, 3Hyp, 4Hyp, and Met.

9. The AMPPP of claim 8 wherein said amino acid Asn is substituted with an amino acid selected from the group consisting of Arg, His, Ala, Gly and Pro.

10. The AMPPP of claim 1 wherein said Magainin 2 derivative lacks a naturally occurring His.

11. The AMPPP of claim 1 wherein said Magainin 2 derivative lacks a Ser immediately C terminal a naturally occurring His.

12. The AMPPP of claim 1 wherein said Magainin 2 derivative lacks a naturally occurring Met.

13. The AMPPP of claim 1 wherein said Magainin 2 derivative lacks a naturally occurring Asn.

14. An AMPPP which is a Magainin derivative having increased resistance to proteolytic degradation when compared to naturally occurring Magainin 1 having an amino acid sequence of GlyIleGlyLysPheLeuHisSerAla GlyLysPheGlyLysAlaPheValGlyGluIleMetLysSer, said increased resistance too proteolytic degradation being imparted by a substitution for at least one of the amino acids His, Met, Asn, and the non-C terminal Ser which are naturally occurring in Magainin 1.

15. The AMPPP of claim 14 wherein said amino acid His is substituted with an amino acid selected from the group consisting of Phe, Ala, Glu, Asp, Lys, Set and Arg.

16. The AMPPP of claim 15 wherein said amino acid His is substituted with an amino acid selected from the group consisting of Arg, Lys and Phe.

17. The AMPPP of claim 14 wherein said amino acid Ser is substituted with an amino acid selected from the group consisting of Thr, Asp, Ala, His and Glu.

18. The AMPPP of claim 17 wherein said amino acid Ser is substituted with the amino acid Glu.

19. The AMPPP of claim 14 wherein said Magainin 1 lacks a naturally occurring His.

20. The AMPPP of claim 14 wherein said Magainin 1 lacks a Ser immediately C terminal a naturally occurring His.

21. An AMPPP which is a Magainin derivative having increased resistance to proteolytic degradation relative to a naturally occurring Magainin 1or 2 and which is substituted in at least one of amino acid position seven or eight.

22. The AMPPP of claim 21 which an amino acid selected from the group consisting of Phe, Ala, Glu, Asp, Lys, Ser and Arg is substituted at position seven.

23. The AMPPP of claim 22 wherein an amino acid selected from the group consisting of Thr, Asp, Ala, His and Glu is substituted at position eight.

24. The protein having the amino acid sequence Gly IleGlyLysPheLeuHisGluAlaLysLysPheGlyLysAlaPheValGlyGluIleMetAsn Ser-OH.

25. The protein having the amino acid sequence Gly IleGlyLysPheLeuLysSerAlaLysLysPheGlyLysAlaPheValGlyGluIleMetAsn Ser-OH.

26. The protein having the amino acid sequence Gly IleGlyLysPheLeuArgSerAlaLysLysPheGlyLysAlaPheValGlyGluIleMetAsn Ser-OH.

27. The protein having the amino acid sequence Gly IleGlyLysPheLeuPheSerAlaLysLysPheGlyLysAlaPheValGlyGluIleMetAsnSer-OH. Ser-Oh.

* * * * *

UNITED STATES PATENT AND TRADEMARK OFFICE

CERTIFICATE OF CORRECTION

PATENT NO. : 5,424,395 Page 1 of 3

DATED : June 13, 1995

INVENTOR(S) : Bascomb et al.

It is certified that error appears in the above-identified patent and that said Letters Patent is hereby corrected as shown below:

Column 3, line 53, after the word "Analogs" Strength change "." to --,--.
Column 4, line 28, "7" should read --17--.
Column 5, line 4, "79" should read --179--.
Column 8, line 8, "Xaa19," should read --$Xaa^{19}$,--.
Column 9, line 42, "Ash" should read --Asn--.
Column 10, line 67, "Xaa19," should read --$Xaa^{19}$,--
Column 11, line 52, "AMPPPS" should read --AMPPPs--.
Column 14, line 53, after "Leu, Lys," insert --Met, Phe, Pro, Ser, Thr, Trp, Tyr, and Val, and wherein--.
Column 16, line 20, before "Gly," cancel the word --Glu,--.
Column 17, line 40, "Lys" should read --Xaa--.
Column 19, line 2, "AMPPs" should read --AMPPPs--.
Column 28, line 31 "trifluoracetic" should read --trifluoroacetic--.
Column 28, line 36, "trifluoracetic" should read --trifluoroacetic--.
Column 33, line 68, "his" should read --*his*--.
Column 37, line 10 "*-Xaa11*" should read -- -$Xaa^{11}$--.
Column 37, line 38, "and/Or" should read --and/or--.
Column 37, line 40, "Thr Asp Ala His or Glu at $Xaa^{8}$ Arg," should read --Thr, Asp, Ala, His or Glu at $Xaa^{8}$, Arg,--.
Column 41, line 45, "Xaa 19" should read --$Xaa^{19}$--.
Column 42, line 18, "AMPPs" should read --AMPPPs--.
Column 43, line 34, "Xaa13," should read --$Xaa^{13}$,--.
Column 47, line 78, after "AlaPheVal" "Oly" should read --Gly--.
Column 49, line 4, after "PheValGly" "oluIleX&t" should read --GluIleMet--.
Column 49, line 47, after "LysAlaPheVal" "ely" should read --Gly--.
Column 51, line 55, "Hat" should read --Met--.
Column 51, line 59, "Hat" should read --Met--.

UNITED STATES PATENT AND TRADEMARK OFFICE

CERTIFICATE OF CORRECTION

PATENT NO. : 5,424,395
Page 2 of 3
DATED : June 13, 1995
INVENTOR(S) : Bascomb et al.

It is certified that error appears in the above-identified patent and that said Letters Patent is hereby corrected as shown below:

Column 59, line 9, after "IleGlyLys" "Met" should read --Phe--.
Column 68, line 26, "t-Boc-[$pro^{11}$]" should read --t-Boc-[$Pro^{11}$]--.
Column 68, line 63, "2-$OCH^2$PAM" should read --2-$OCH_2$PAM--.
Column 70, line 13, "minute" should read --minutes--.
Column 71, line 66, "(65.6>94," should read --(65.62>94,--.
Column 74, line 28, after "GlyLysPhe" "Lsu" should read --Leu--.
Column 74, line 44, cancel the number "30".
Column 74, line 59, after "GlyGluIle" "met" should read --Met--.
Column 74, line 60, after "GlyLysPhe" "loeu" should read --Leu--.
Column 74, line 62, after "GluIle" "met" should read --Met--.
Column 79, lines 19-20, "chlo-roplast" should read --Chlo-roplast--.
Column 80, line 67, "uM" should read --μM--.
Column 83, line 3, "phosphtased" should read --phosphatased--.
Column 84, line 27, "HisSerAlaLys LysPheGlyLysAlaPheValGly-" should read --HisSerAlaLysLysPheGlyLysAlaPheValGly---.
Column 84, line 31, "natural" should read --naturally--.

UNITED STATES PATENT AND TRADEMARK OFFICE
CERTIFICATE OF CORRECTION

PATENT NO. : 5,424,395

DATED : June 13, 1995

INVENTOR(S) : Bascomb et al.

It is certified that error appears in the above-identified patent and that said Letters Patent is hereby corrected as shown below:

Column 85, line 1, "Magainin" should read --Magainin 1--.
Column 85, line 5, "PheLeuHisSerAla GlyLysPheGlyLysAlaPheValGly-" should read --PheLeuHisSerAlaGlyLysPheGlyLysAlaPheValGly---.
Column 85, line 6, "too" should read --to--.
Column 85, line 12, after "Glu, Asp, Lys," "Set" should read --Ser--.
Column 86, line 17, "PheValGlyGluIleMetAsn Ser-OH." should read --PheValGlyGluIleMetAsnSer-OH.--
Column 86, line 20, "PheValGlyGluIleMetAsn Ser-OH." should read --PheValGlyGluIleMetAsnSer-OH.--
Column 86, line 23, "PheValGlyGluIleMetAsn Ser-OH." should read --PheValGlyGluIleMetAsnSer-OH.--
Column 86, line 26, cancel "Ser-Oh."

Signed and Sealed this

Ninth Day of July, 1996

Attest:

BRUCE LEHMAN

*Attesting Officer* *Commissioner of Patents and Trademarks*